(12) United States Patent
Dixon et al.

(10) Patent No.: US 11,672,870 B2
(45) Date of Patent: *Jun. 13, 2023

(54) TRANSDUCTION

(71) Applicant: The University of Nottingham, Nottinghamshire (GB)

(72) Inventors: James Dixon, Nottinghamshire (GB); Kevin Shakesheff, Nottinghamshire (GB); Chris Denning, Nottinghamshire (GB)

(73) Assignee: UNIVERSITY OF NOTTINGHAM, Nottinghamshire (GB)

( * ) Notice: Subject to any disclaimer, the term of this patent is extended or adjusted under 35 U.S.C. 154(b) by 446 days.

This patent is subject to a terminal disclaimer.

(21) Appl. No.: 16/266,535

(22) Filed: Feb. 4, 2019

(65) Prior Publication Data

US 2019/0216941 A1 Jul. 18, 2019

Related U.S. Application Data

(63) Continuation of application No. 15/105,030, filed as application No. PCT/GB2014/053764 on Dec. 18, 2014, now Pat. No. 10,226,537.

(30) Foreign Application Priority Data

Dec. 18, 2013 (GB) ..................................... 1322396

(51) Int. Cl.
| | |
|---|---|
| *A61K 31/726* | (2006.01) |
| *A61K 31/727* | (2006.01) |
| *A61K 38/17* | (2006.01) |
| *A61K 39/395* | (2006.01) |
| *A61K 47/64* | (2017.01) |
| *C07K 14/705* | (2006.01) |
| *C07K 16/18* | (2006.01) |
| *C07K 19/00* | (2006.01) |
| *C12N 15/63* | (2006.01) |
| *C07K 14/475* | (2006.01) |
| *A61K 39/00* | (2006.01) |

(52) U.S. Cl.
CPC .......... *A61K 47/645* (2017.08); *A61K 31/726* (2013.01); *A61K 31/727* (2013.01); *A61K 38/177* (2013.01); *A61K 39/3955* (2013.01); *C07K 14/475* (2013.01); *C07K 14/705* (2013.01); *C07K 16/18* (2013.01); *C07K 19/00* (2013.01); *C12N 15/63* (2013.01); *A61K 2039/505* (2013.01); *C07K 2319/01* (2013.01); *C07K 2319/10* (2013.01); *C07K 2319/20* (2013.01); *C07K 2319/33* (2013.01)

(58) Field of Classification Search
CPC ............ A61K 38/177; A61K 2039/505; A61K 39/3955; A61K 31/726; A61K 31/727; C07K 14/705; C07K 16/18; C07K 19/00; C07K 2319/33; C07K 2319/01; C07K 2319/10; C07K 2319/20; C12N 15/63
See application file for complete search history.

(56) References Cited

U.S. PATENT DOCUMENTS

| | | | |
|---|---|---|---|
| 6,858,578 | B2 | 2/2005 | Heartlein et al. |
| 6,881,825 | B1 | 4/2005 | Robbins et al. |
| 7,049,286 | B2 | 5/2006 | Tchelingerian |
| 7,067,487 | B2 | 6/2006 | Langedijk |
| 7,329,638 | B2 | 2/2008 | Yang et al. |
| 8,133,733 | B2 | 3/2012 | Khan |
| 8,273,867 | B2 | 9/2012 | Dowdy et al. |
| 8,410,045 | B2 | 4/2013 | Michel et al. |
| 8,529,928 | B2 | 9/2013 | Wang et al. |
| 8,703,906 | B2 | 4/2014 | Baumhof et al. |
| 8,778,886 | B2 | 7/2014 | Kumar-Singh et al. |
| 9,180,161 | B2 | 11/2015 | Komatsu et al. |
| 2002/0151004 | A1 | 10/2002 | Craig |
| 2002/0193395 | A1 | 12/2002 | Kisilevsky et al. |
| 2003/0104622 | A1 | 6/2003 | Robbins et al. |
| 2003/0190364 | A1 | 10/2003 | Panitch et al. |
| 2007/0071677 | A1 | 3/2007 | Park et al. |
| 2007/0197430 | A1 | 8/2007 | Baell et al. |
| 2008/0027025 | A1 | 1/2008 | Dowdy et al. |

(Continued)

FOREIGN PATENT DOCUMENTS

| | | |
|---|---|---|
| EP | 1 867 661 A1 | 12/2007 |
| EP | 2044125 B1 | 9/2010 |

(Continued)

OTHER PUBLICATIONS

Abu-Awwad et al. Controlled release of GAG-binding enhanced transduction (GET) peptides for sustained and highly efficient intracellular delivery. Acta Biomaterialia 57: 225-237, 2017.*

(Continued)

*Primary Examiner* — Bridget E Bunner
(74) *Attorney, Agent, or Firm* — Thomas|Horstemeyer, LLP

(57) ABSTRACT

This invention relates to transduction of cargo molecules into living cells, such as protein transduction, in particular a delivery molecule for transduction of a cargo into a cell comprising: a cargo-binding molecule and/or a cargo; a glycosaminoglycan (GAG) binding element, which is capable of binding to GAG on the surface of the cell; and a protein transduction domain. Methods of transduction, methods of producing or modifying cargo for transduction, delivery molecules for transduction and methods of treatment using transduction, or using transduced cells are also provided.

15 Claims, 60 Drawing Sheets

Figure 1:
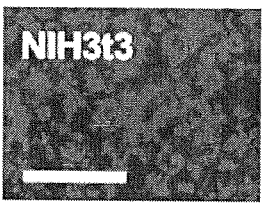
Figure 1:
Figure 1:
Figure 1:
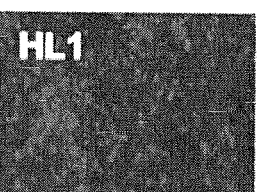
Figure 1:
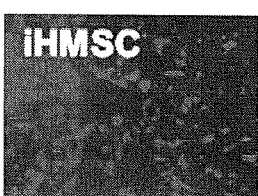
Figure 1:
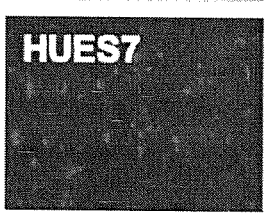
Figure 1:
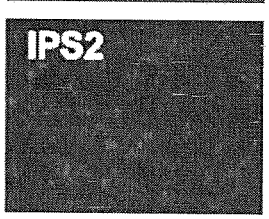
Figure 1:
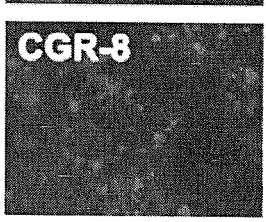
Figure 1:
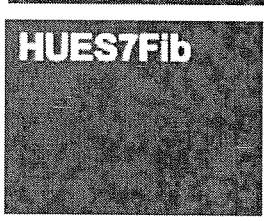
Figure 1:
Figure 1:
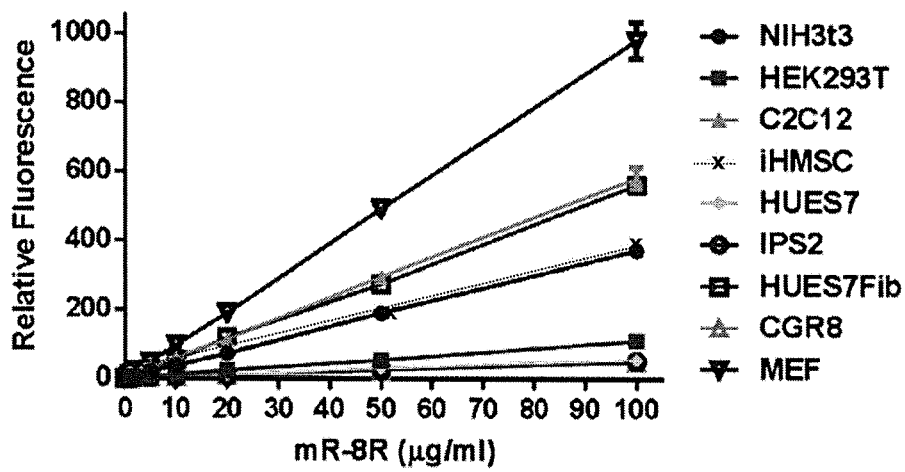
Figure 1:
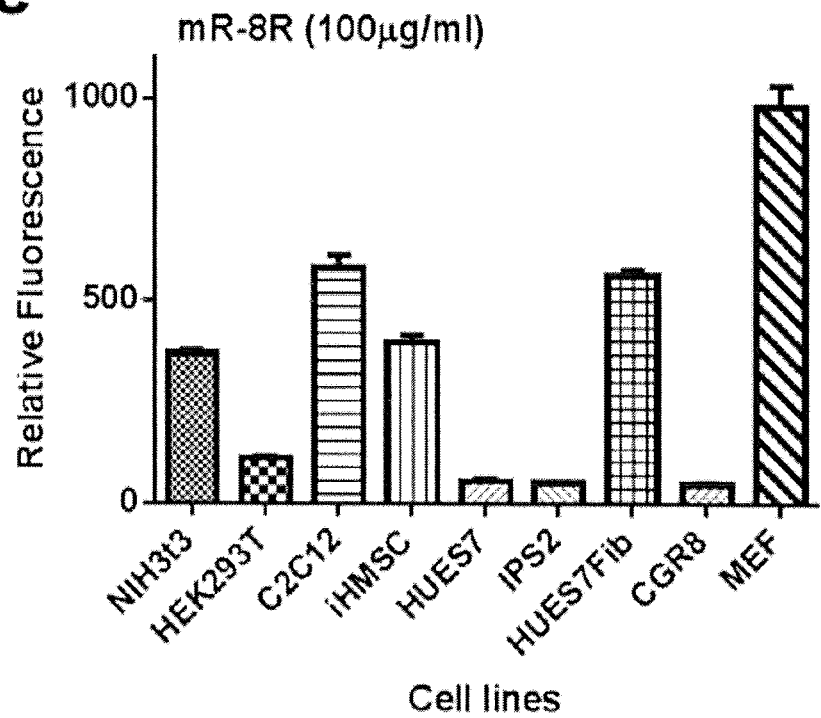

Specification includes a Sequence Listing.

(56) References Cited

U.S. PATENT DOCUMENTS

| | | | |
|---|---|---|---|
| 2009/0098049 | A1 | 4/2009 | Dowdy et al. |
| 2010/0221235 | A1 | 9/2010 | Arranz |
| 2011/0054236 | A1 | 3/2011 | Yang et al. |
| 2011/0117026 | A1 | 5/2011 | Tseng et al. |
| 2012/0190107 | A1 | 7/2012 | Bisgrove et al. |
| 2014/0073557 | A1 | 3/2014 | Kungl et al. |
| 2015/0064783 | A1 | 3/2015 | Park et al. |
| 2015/0165060 | A1 | 6/2015 | Park et al. |
| 2016/0031985 | A1 | 2/2016 | Bowdish et al. |

FOREIGN PATENT DOCUMENTS

| | | |
|---|---|---|
| EP | 2354155 A2 | 8/2011 |
| EP | 3082871 | 10/2016 |
| JP | 2003528596 A | 9/2003 |
| JP | 2009525744 A | 7/2009 |
| WO | 2003084481 A1 | 10/2003 |
| WO | 2007091159 A2 | 8/2007 |
| WO | 2010010112 A2 | 1/2010 |
| WO | 2013114363 A2 | 8/2013 |
| WO | 2014004465 A1 | 1/2014 |

OTHER PUBLICATIONS

Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Clark et al. Mapping the differential distribution of glycosaminoglycans in the adult human retina, choroid, and sclera. Invest Ophthalmol Vis Sci 52(9): 6511-6521, 2011.*
Cronican et al. A class of human proteins that deliver functional proteins in mammalian cells in vitro and in vivo. Chem Biol 18: 833-838, 2011 (with supplement).*
Delgado-Roche et al. The treatment with an anti-glycosaminoglycan antibody reduces aortic oxidative stress in a rabbit model of atherosclerosis. Free Radical Res 47(4): 309-315, 2013.*
Dixon et al. Highly efficient delivery of functional cargoes by the synergistic effect of GAG binding motifs and cell-penetrating peptides. Proc Natl Acad Sci USA 113: E291-E299, 2016.*
Doerks et al. Protein annotation: detective work for function prediction. Trends in Genetics 14:248-250, 1998.*
Favretto et al. Glycosaminoglycans in the cellular uptake of drug delivery vectors—bystanders or active players? J Controlled Rel 180: 81-90, 2014.*
Guo et al. Protein tolerance to random amino acid change. Proc Natl Acad Sci USA 101(25): 9205-9210, 2004.*
Higashiyama et al. A heparin-binding growth factor secreted by macrophage-like cells that is related to EGF. Science 251: 936-939, 1991.*
Lee et al. The cell-penetrating peptide domain from human heparin-binding epidermal growth factor-like growth factor (HB-EGF) has anti-inflammatory activity in vitro and in vivo. Biochem Biophys Res Comm 419: 597-604, 2012.*
Luo et al. The heparin-binding domain of HB-EGF as an efficient cell-penetrating peptide for drug delivery. J Peptide Sci 22: 689-699, 2016.*
Ngo et al. "Computational complexity, protein structure prediction, and the Levinthal paradox" in The Protein Folding Problem and Tertiary Structure Prediction, pp. 492-495, 1994.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Sorrell et al. A monoclonal antibody which recognizes a glycosaminoglycan epitope in both dermatan sulfate and chondroitin sulfate proteoglycans of human skin. Histochem J 31: 549-558, 1999.*
Thompson et al. Characterization of sequences within heparin-binding EGF-like growth factor that mediate interaction with heparin. J Biol Chem 269(4): 2541-2549, 1994.*
Wells, J.A. Additivity of mutational effects in proteins. Biochemistry 29(37): 8509-8517, 1990.*
Wittrup et al. ScFv antibody-induced translocation of cell-surface heparan sulfate proteoglycan to endocytic vesicles. J Biol Chem 284(47): 32959-32967, 2009.*
Sakuma et al. CD9 antigen interacts with heparin-binding EGF-like growth factor through its heparin-binding domain. J Biochem 122: 474-480, 1997.*
International Search Report and Written Opinion of Application No. PCT/GB2014/053764 dated Jun. 25, 2015.
International Preliminary Report on Patentability of Application No. PCT/GB2014/053764 dated Jun. 30, 2016.
James E Dixon et al: "Get: glycosaminoglycan (gag)-binding enhanced transduction of functional proteins", European Cells and Materials, Jan. 1, 2014 (Jan. 1, 2014), pp. 63, XP055177030, Retrieved from the Internet <URL:http://www.ecmjournal.org/journal/supplements/vol028supp04/pdf/Vol028Supp04a063.pdf> [retrieved on Mar. 17, 2015].
Li Hua et al: "Highly efficient delivery of siRNA to a heart transplant model by a novel cell penetrating peptide-dsRNA binding domain", International Journal of Pharmaceutics, vol. 469, No. 1, Apr. 23, 2014 (Apr. 23, 2014), pp. 206-213, XP029029887, ISSN: 0378-5173, DOI: 10.1016/J.IJPHARM.2014.04.050.
Rudolph C et al: "Oligomers of the arginine-rich motif of the HIV-1 TAT protein are capable of transferring plasmid DNA into cells", Journal of Biological Chemistry, American Society for Biochemistry and Molecular Biology, US, vol. 278, No. 13, Jan. 8, 2003 (Jan. 8, 2003), pp. 11411-11418, XP002403121, ISSN: 0021-9258, DOI: 10.1074/JBC.M211891200.
Alfredo M. Angeles-Boza et al: "Generation of Endosomolytic Reagents by Branching of Cell-Penetrating Peptides: Tools for the Delivery of Bioactive Compounds to Live Cells in Cis or Trans", Bioconjugate Chemistry, vol. 21, No. 12, Dec. 15, 2010 (Dec. 15, 2010), pp. 2164-2167, XP055178326, ISSN: 1043-1802, DOI: 10.1021/bc100130r.
James E Dixon et al: "Directed Differentiation of Human Embryonic Stem Cells to Interrogate the Cardiac Gene Regulatory Network", Molecular Therapy, vol. 19, No. 9, Jun. 21, 2011 (Jun. 21, 2011), pp. 1695-1703, XP055176812, ISSN: 1525-0016, DOI: 10.1038/mt.2011.125.
Chen Chien-Jung et al: "In Vitro Characterization and in Vivo Application of a Dual Functional Peptide", 2013 Seventh International Conference on Complex, Intelligent, and Software Intensive Systems, IEEE, Jul. 3, 2013 (Jul. 3, 2013), pp. 576-581, XP032485643, DOI: 10.1109/CISIS.2013.104.
Huang Yongzhuo et al: "Curb challenges of the Trojan Horse approach: Smart strategies in achieving effective yet safe cell-penetrating peptide-based drug", Advanced Drug Delivery Reviews, vol. 65, No. 10, Jan. 28, 2013 (Jan. 28, 2013), pp. 1299-1315, XP028737355, ISSN: 0169-409X, DOI: 10.1016/J.ADDR.2012.11.007.
Arjen Van Den Berg et al: "Protein transduction domain delivery of therapeutic macromolecules", Current Opinion in Biotechnology, vol. 22, No. 6, Apr. 12, 2011 (Apr. 12, 2011), pp. 888-893, XP028397478, ISSN: 0958-1669, DOI: 10.1016/J.COPBIO.2011.03.008.
Farkhani Samad Mussa et al: "Cell penetrating peptides: Efficient vectors for delivery of nanoparticles, nanocarriers, therapeutic and diagnostic molecules", Peptides, vol. 57, Apr. 30, 2014 (Apr. 30, 2014), pp. 78-94, XP028854855, ISSN: 0196-9781, DOI: 10.1016/J.PEPTIDES.2014.04.015.
Dietz G P H et al: "Delivery of bioactive molecules into the cell: the Trojan horse approach", Molecular and Cellular Neurosciences, San Diego, US, vol. 27, No. 2, Oct. 1, 2004 (Oct. 1, 2004), pp. 85-131, XP004599335, ISSN: 1044-7431, DOI: 10.1016/J.MCN.2004.03.005.
Francesca Milletti: "Cell-penetrating peptides: classes, origin, and current landscape", Drug Discovery Today, vol. 17, No. 15-16, Aug. 1, 2012 (Aug. 1, 2012), pp. 850-860, XP055102101, ISSN: 1359-6446, DOI: 10.1016/j.drudis.2012.03.002.

(56) References Cited

OTHER PUBLICATIONS

Ja-Hyun Koo et al: "Cell membrane penetrating function of the nuclear localization sequence in human cytokine IL-1[alpha]", Molecular Biology Reports, vol. 41, No. 12, Sep. 10, 2014 (Sep. 10, 2014), pp. 8117-8126, XP055178433, ISSN: 0301-4851, DOI: 10.1007/s11033-014-3711-7.
Catherine De Coupade et al., "Novel human-derived cell-penetrating peptides for specific subcellular delivery of therapeutic biomolecules", Biochem, J., 2005, vol. 390, pp. 407-418.
Florence Meyer-Losie, et al., "Improved Therapeutic Efficacy of Doxorubicin through Conjugation with a Novel Peptide Drug Delivery Technology (Vectocell)", J. Med. Chem., 2006, vol. 390, pp. 6908-6916.
Wang et al 2001. J. Biol Chem. 276:49213-49220.
Tokuriki et al. 2009. Current Opin. In Struct. Biol. 19:596-604.
Bhattacharya et al 2017. Plos One. 12(3):e0171355:1-22.
Poon et al. 2007. Biochem Soc Trans. 35:788-793.

\* cited by examiner a mR    [ mRFP ]

mR-8R    [ mRFP | 8R ]

b

NIH3t3 (100µg/ml, 12h)

mR    mR-8R c

NIH3t3   HEK293T   C2C12   HL1
iHMSC   HUES7   IPS2   CGR-8
HUES7Fib   MEF mR-8R (100µg/ml, 12h)

20μg/ml Transduction

TRANSDUCTION

CROSS-REFERENCE TO RELATED APPLICATIONS

This application is a continuation of U.S. patent application Ser. No. 15/105,030, filed Nov. 28, 2016, which is the National Stage of International Application No. PCT/GB2014/053764, filed 18 Dec. 2014, having the title "TRANSDUCTION" which claims the benefit of and priority to GB Application No. 1322396.1, filed on 18 Dec. 2013, the contents of all of which are incorporated by reference as if fully set forth herein.

SEQUENCE LISTING

This application contains a sequence listing filed in electronic form as an ASCII.txt file entitled "SEQUENCE LISTING_ST25_221230.txt", created on Dec. 30, 2022 and having a size of 18 kb. The content of the sequence listing is incorporated herein in its entirety.

This invention relates to transduction of cargo molecules into living cells, such as protein transduction, in particular methods of transduction, methods of producing or modifying cargo for transduction, delivery molecules for transduction and methods of treatment using transduction, or using transduced cells.

With complete tools for the human genome and a defined transcriptome, research is now focused on functionally annotating the proteome to allow intelligent selection of therapeutic targets for clinical translation {Zografos, 2013 #86}. Protein interaction and how this modifies function will further complicate target choice and protein functionality will need to be determined and validated in normal and diseased models {Natrajan, 2013 #89}. DNA and RNA-based approaches such as DNA transgenesis and small-interfering/antisense oligonucleotides which mediate gene up-regulation or knockdown are invaluable tools {Yamaguchi, 2009 #87}. However these approaches may not be clinically relevant due to genetic modification or may not accurately correspond to protein activity due to lack of correlation between transcript and protein levels {Peng, 2011 #88}. Delivery of proteins directly rather than DNA constructs or RNA molecules has various advantages; the most notable being that the active agent is being directly administered rather than relying on a system to generate this by intracellular machinery {Gump, 2007 #39}.

Altering protein function in cells has in practice been limited historically to genetically transforming cells with DNA that are built into a vector construct, such as a lentiviral vector. This means that the cells carry exogenous genetic material including the desired extra genes and also vector DNA that is required for the modification of the cells and expression of the exogenous gene constructs. This heterologous DNA can potentially cause issues with genetic inheritance, for example in human cell therapeutics. As an example, the generation of induced pluripotent stem cells (iPS cells) can be achieved by genetic transduction of specific reprogramming-associated genes using retroviral or lentiviral vectors. However, an obstacle to the therapeutic use of this technology is the production of insertional mutagenic lesions that are potentially tumorigenic. One possible strategy to entirely replace gene delivery is protein transduction.

Other potential protein transduction therapies could include myogenic differentiation of human adult stem cells (hASCs), for example, for treatment of muscle disorders.

The aim of the invention is to be able to bypass the use of DNA constructs and instead transduce cells directly with protein without the need for DNA constructs.

Transducing cells with protein without the use of DNA constructs is known and there are an ever increasing number of potent delivery molecules known to promote the transduction of large molecular cargos such as proteins, peptides, oligonucleotides and nanoparticles into a wide variety of cells {El-Andaloussi, 2005 #36}. Cationic peptide protein transduction domain (PTD)-mediated cellular transduction represents a cell entry approach with enormous potential for the delivery of therapeutic macromolecules. The human immunodeficiency virus (HIV-1) TAT protein basic domain (RKKRRQRRR (SEQ ID NO: 20) and longer variants) and other PTDs {El-Andaloussi, 2005 #36} such as poly-Arginine (e.g. 8R; RRRRRRRR (SEQ ID NO: 19)) or Lysine, have been used to deliver a wide variety of bioactive cargos into cells in culture and preclinical models in vivo {El-Andaloussi, 2005 #36; Goun, 2006 #38; Meade, 2007 #37}. Efficient delivery of peptide, nucleic acid and large molecule cargoes by PTDs has been demonstrated by many groups and several clinical trials are currently on-going using PTD-mediated delivery. Many mechanistic studies on PTD-uptake have been undertaken with the precise mechanism still poorly defined {Fischer, 2005 #41; Gump, 2007 #39; Nakase, 2008 #40; Heitz, 2009 #42; Gump, 2010 #2}.

It is understood that PTD-fused cargos are translocated through the cell membrane and their extracellular concentration dictates the efficiency of delivery. Recent studies have demonstrated that PTD-mediated protein delivery is mediated by endocytotic pathways, such as lipid raft-dependant macropinocytosis {Gump, 2010 #2}. After internalization by macropinocytosis protein cargos are contained within macropinocytomes and not free within cytosol; restricting correct localization and activity. Macropinocytotic vesicles are considered leaky endosomes compared to other types and progressively lose membrane integrity due to acidification. This means that any escape of PTD-tagged proteins is likely to be due to these properties {Norbury, 1995 #21; Meier, 2002 #20}. Importantly macropinocytic vesicles do not fuse into lysosomes to degrade their contents {Conner, 2003 #22}. However the delivery requires vast excesses of proteins extracellularly to drive translocation. Furthermore significant amounts need to be delivered for an effective amount to escape endosomal retention and be biologically functional. Various techniques have been developed to stimulate the release of cargo from these vesicles including ultrasound, co-treatment with endosome-disruptive peptides or chemical treatments, such as chloroquine, against the endosomal pathways {Gump, 2007 #39}. Co-delivery of endosomal-disruptors is attractive as these peptides could be directly delivered with cargos {Wadia, 2004 #25}, however the efficiency of this process still leaves the vast majority of protein trapped away from cytosol {Skehel, 2001 #34; Han, 2001 #35}. Therefore, being able to directly transduce the cell with sufficient quantities of protein, for example to have physiological or metabolic expression effects on the cells, has not been a practical option hitherto.

An aim of the present invention is to provide an improved method of transduction of cargo for providing physiological or metabolic effects on the cell.

According to a first aspect of the invention, there is provided a delivery molecule for transduction of a cargo into a cell comprising:
- a cargo;
- a glycosaminoglvcan (GAG) binding element, which is capable of binding to GAG on the surface of the cell; and
- a protein transduction domain.

According to another aspect of the invention, there is provided a delivery molecule for transduction of a cargo into a cell comprising:
- a cargo-binding molecule for binding to a cargo, and optionally wherein the cargo is bound to the cargo-binding molecule;
- a glycosaminoglycan (GAG) binding element, which is capable of binding to GAG on the surface of the cell; and
- a protein transduction domain.

Advantageously, the provision of the delivery molecule of the present invention can increase the efficiency of transduction of a cargo into cells, such as stem cells. In some examples a >100-fold improvement in delivery amount compared to any existing known system has been shown. The GAG binding element, such as HS-GAG binding element P21 (from a growth factor), in combination with a protein transduction domain, such as 8mer arginine peptide, and a cargo, greatly facilitates the uptake of very large quantities of the cargo into cells, such as mammalian cells. Not only do the cells take up the delivery molecule (by macro-pinocytosis) but the delivery molecules have been shown to traverse the cellular matrix and be delivered to the nucleus. This procedure is more effective than DNA-based delivery of proteins and the cargo is delivered to sites where activity is desired (including the nucleus). Cell specific responses are also achievable.

This technology provides a step-change not only in what has hitherto been limited to transgenic experiments but also sets the stage for therapeutic use of iPSCs (induced pluripotent stem cells), where the iPSCs no longer need to be modified with DNA constructs.

Advantageously, providing a cargo-binding molecule provides a molecule that is functionalised to attach to, and transport a diverse range of cargos across the cell membrane.

The inventive molecule delivery system herein may be referred to as GET (GAG-binding enhanced transduction) or otherwise Heparan-sulfate enhanced transduction domain (HETD)-mediated delivery. These terms may be used interchangeably.

The GAG binding element may be a heparan sulphate glycosaminoglycan (HS-GAG) binding element, which is capable of binding to HS-GAG on the surface of the cell.

Heparan sulfate glycosaminoglycan (HS-GAG) is a proteoglycan in which two or three HS chains are attached in close proximity to cell surface or extracellular matrix proteins. It is in this form that HS binds to a variety of protein ligands and regulates a wide variety of biological activities, including developmental processes, angiogenesis, blood coagulation and tumour metastasis. Heparan sulfate is a member of the glycosaminoglycan family of carbohydrates and is very closely related in structure to heparin. Both consist of a variably sulfated repeating disaccharide unit. The most common disaccharide unit within heparan sulfate is composed of a glucuronic acid (GlcA) linked to N-acetylglucosamine (GlcNAc) typically making up around 50% of the total disaccharide units.

The GAG binding element may have specific affinity for GAG. The HS-GAG binding element may have specific affinity for HS-GAG. The HS-GAG binding element may comprise a heparin binding domain (HBD), or a variant thereof. The heparin binding domain variant may comprise a truncated heparin binding domain, or an extended heparin binding domain. The GAG binding element may comprise any protein, peptide or molecule that specifically or preferentially binds to GAG. The HS-GAG binding element may comprise any protein, peptide or molecule that specifically or preferentially binds to HS-GAG.

The HS-GAG binding element may comprise at least part of the heparin binding domain of Heparin-Binding EGF-like Growth Factor (HB-EGF). The heparin binding domain may comprise P21 of HB-EGF. The heparin binding domain may comprise a truncated, extended, or functional variant of P21.

The HS-GAG binding element may comprise a heparin binding domain of a fibroblast growth factor, or a functional part or variant thereof.

The HS-GAG binding element may be selected from any of the group comprising FGF, antithrombin, such as ATIII, VEGF, BMPs, Wnts, Shh EGFs, and PDGF; or variants thereof. The HS-GAG binding element may comprise any of FGF2, FGF7, or PDGF. The HS-GAG binding element may comprise one or more of the heparan binding sulphate domains of any FGF protein (e.g. domains A, B or C). The HS-GAG binding element may comprise FGF4. The HS-GAG binding element may comprise FGF1 HBD A (heparan sulphate binding domain A (the first HBD domain of FGF1)), FGF2 HBD A (heparan sulphate binding domain A), FGF4 HBD A (heparan sulphate binding domain A), FGF1 HBD C (heparan sulphate binding domain C), FGF2 HBD B (heparan sulphate binding domain B), FGF2 HBD C (heparan sulphate binding domain C), FGF4 HBD C (heparan sulphate binding domain C), FGF7 HBD B (heparan sulphate binding domain B), FGF7 IIBD C (heparan sulphate binding domain C), antithrombin, such as ATIII, VEGF, or PDGF, or variants thereof.

The HS-GAG binding element may be selected from any of the group comprising Hepatocyte Growth Factor, Interleukin, morphogens, HS-GAG binding enzymes, Wnt/Wingless. Endostatin, viral protein, such as foot and mouth disease virus protein, annexin V, lipoprotein lipase; or HS-GAG binding fragments thereof. The HS-GAG binding element may comprise any protein, peptide or molecule capable of specifically binding HS-GAG.

A "variant" may be understood by the skilled person to include a functional variant, wherein there may be some sequence differences from the known, reported, disclosed or claimed sequence, but the variant may still bind to HS-GAG. Conservative amino acid substitutions are also envisaged within the meaning of "variant".

The HS-GAG binding element may comprise the amino acid sequence KRKKKGKGLGKKRDPCLRKYK (P21) SEQ ID NO. 1). The HS-GAG binding element may comprise a sequence having at least 80% identity to SEQ ID NO. 1. The HS-GAG binding element may comprise a sequence having at least 90% identity to SEQ ID NO. 1. The HS-GAG binding element may comprise a sequence having at least 95% identity to SEQ ID NO. 1. The HS-GAG binding element may comprise a sequence having at least 98% identity to SEQ ID NO. 1. The HS-GAG binding element may comprise a sequence having at least 99% identity to SEQ ID NO. 1.

The HS-GAG binding element may comprise the amino acid sequence G R P R E S G K K R K R K R L K P T (PDGF, SEQ ID NO. 3). The HS-GAG binding element may comprise a sequence having at least 80% identity to SEQ ID NO. 3. The HS-GAG binding element may comprise a sequence having at least 90% identity to SEQ ID NO. 3. The HS-GAG binding element may comprise a sequence having at least 95% identity to SEQ ID NO. 3. The HS-GAG binding element may comprise a sequence having at least 98% identity to SEQ ID NO. 3. The HS-GAG binding element may, comprise a sequence having at least 99% identity to SEQ ID NO. 3.

The HS-GAG binding element may comprise the amino acid sequence T Y A S A K W T H N G G E M F V A L N Q ((FGF7, IIBD B) SEQ ID NO. 5). The HS-GAG binding element may comprise a sequence having at least 80% identity to SEQ ID NO. 5. The IIS-GAG binding element may comprise a sequence having at least 90% identity to SEQ ID NO. 5. The HS-GAG binding element may comprise a sequence having at least 95% identity to SEQ ID NO. 5. The HS-GAG binding element may comprise a sequence having at least 98% identity to SEQ ID NO. 5. The HS-GAG binding element may comprise a sequence having at least 99% identity to SEQ ID NO. 5.

The HS-GAG binding element may comprise the amino acid sequence T Y R S R K Y T S W Y V A L K R (FGF2 HBD B SEQ ID NO. 7). The HS-GAG binding element may comprise a sequence having at least 80% identity to SEQ ID NO. 7. The HS-GAG binding element may comprise a sequence having at least 90% identity to SEQ ID NO. 7. The HS-GAG binding element may comprise a sequence having at least 95% identity to SEQ ID NO. 7. The HS-GAG binding element may comprise a sequence having at least 98% identity to SEQ ID NO. 7. The HS-GAG binding element may comprise a sequence having at least 99% identity to SEQ ID NO. 7.

Sequence identity may be determined by standard BLAST alignment parameters (provided by www.ncbi.nlm.nih.gov).

The GAG binding element may comprise a GAG binding antibody, or a variant or fragment thereof. The HS-GAG binding element may comprise a HS-GAG binding antibody, or a variant or fragment thereof. The antibody fragment may be an antibody variable domain, an scFv, a diabody, a FAb, a Dab, a F(ab)'2, a heavy-light chain dimer, or a single chain structure. The antibody variant may comprise a protein scaffold comprising CDRs, an antibody mimetic, or a DARPin.

The GAG or HS-GAG binding element may comprise a nanobody (single-domain antigen-binding fragments derived from heavy-chain antibodies that are devoid of light chains and occur naturally in Camelidae).

The single-domain antibody may comprise a $V_HH$ fragment comprising a CDR1, CDR2 and CDR3 wherein
CDR1 may comprise or consists of the amino acid sequence of GFTVSSNE (SEQ ID NO: 21) or GFAFSSYA (SEQ ID NO: 22);
CDR2 may comprise or consists of the amino acid sequence of ISGGST (SEQ ID NO: 23) or IGTGGDT (SEQ ID NO: 24); and
CDR3 may comprise or consists of the amino acid sequence of GRRLKD (SEQ ID NO: 25) or SLRMNGWRAHQ (SEQ ID NO: 26).

The single-domain antibody may comprise a $V_HH$ fragment comprising a CDR1, CDR2 and CDR3 wherein
CDR1 may comprise or consists of the amino acid sequence of GFTVSSNE (SEQ ID NO: 21);
CDR2 may comprise or consists of the amino acid sequence of ISGGST (SEQ ID NO: 23); and
CDR3 may comprise or consists of the amino acid sequence of GRRLKD (SEQ ID NO: 25).

Alternatively, the CDR3 may comprise the amino acid sequence GMRPRL (SEQ ID NO: 27), HAPLRNTRTNT (SEQ ID NO: 28), GSRSSR (SEQ ID NO: 29), GRTVGRN (SEQ ID NO: 30). GKVKLPN (SEQ ID NO: 31), SGRKGRMR (SEQ ID NO: 32), SLRMNGWRAHQ (SEQ ID NO: 26), or RRYALDY (SEQ ID NO: 33).

The single-domain antibody may comprise a $V_HH$ fragment comprising a CDR1, CDR2 and CDR3 wherein
CDR1 may comprise or consists of the amino acid sequence of GFAFSSYA (SEQ ID NO: 22);
CDR2 may comprise or consists of the amino acid sequence of IGTGGDT (SEQ ID NO: 24); and
CDR3 may comprise or consists of the amino acid sequence of SLRMNGWRAHQ (SEQ ID NO: 26).

Alternatively, the CDR3 may comprise the amino acid sequence LKQQGIS (SEQ ID NO: 34). AMTQKKPRKLSL (SEQ ID NO: 35), HAPLRNTRTNT (SEQ ID NO: 28), GMRPRL (SEQ ID NO: 27), RRYALDY (SEQ ID NO: 33), or SGRKYFRARDMN (SEQ ID NO: 36).

The HS-GAG binding element may comprise anti-HS scFv antibodies AO4B08, AO4B05, AO4F12, RB4CB9, RB4CD12, RB4EA12, or R134EG12 (as described in Jenniskens et al (2000, *The Journal of Neuroscience*, 20(11): 4099-4111) and Smits, et al (2006. *METHODS IN ENZYMOLOGY*, VOL. 416, pp. 61-87) incorporated herein by reference); or fragments thereof. The HS-GAG binding element may comprise AO4B08. The HS-GAG binding element may comprise CDR1. CDR2 and CDR3 of AO4B08, AO4B05, AO4F12, RB4CB9, RB4CD12, RB4EA12, or RB4EG12. The HS-GAG binding element may comprise CDR1. CDR2 and CDR3 of AO41308.

The HS-GAG binding element may comprise HS3A8, LKIV69, EW3D10, EW4G2, NS4F5, RB4EA 12, HS4E4 or HS4C3 (as described in Wijnhoven et al (2008) *Glycoconj J* 25:177-185) and Smits, et al (2006. *METHODS IN ENZYMOLOGY*, VOL. 416, pp. 61-87) incorporated herein by reference). The HS-GAG binding element may comprise HS4E4 or HS4C3. The HS-GAG binding element may comprise CDR1, CDR2 and CDR3 of HS3A8, LKIV69, EW3D10, EW4G2, NS4F5, RB4EA12, HS4E4 or HS4C3. The HS-GAG binding element may comprise CDR1, CDR2 and CDR3 of HS4E4 or HS4C3.

The HS-GAG binding element may comprise SEQ ID NO: 15 or 17 (AO4B08). The HS-GAG binding element may comprise SEQ ID NO: 11 or 13 (HS4C3). The HS-GAG binding element may comprise an antibody, or antibody fragment, heavy chain and/or light chain. The HS-GAG binding element may comprise an antibody, or antibody fragment, heavy chain, comprising HCDR1, HCDR2 and HCDR3 chains and/or light chain, comprising LCDR1, LCDR2 and LCDR3.

The protein transduction domain may be hydrophilic or amphiphilic. The protein transduction domain may comprise a majority of hydrophilic amino acid residues. The protein transduction domain may comprise a majority of arginine and/or lysine amino acid residues. The protein transduction domain may comprise a periodic sequence, having a repeated amino acid sequence motif. The protein transduction domain may comprise penetratin, TAT such as HIV derived TAT, MAP, or transportan, pVec, or pep-1.

Where reference is made to a "majority" of residue, this may be understood by the skilled person to include greater than 50% of the residues. A majority may be 55%, 60%, 70%, 80%, 90% or 95% of the residues.

The protein transduction domain may be selected from any of the group comprising

```
Penetratin or Antenapedia PTD
                                    (SEQ ID NO: 37)
RQIKWFQNRRMKWKK;

TAT
                                    (SEQ ID NO: 38)
YGRKKRRQRRR;

SynB1
                                    (SEQ ID NO: 39)
RGGRLSYSRRRFSTSTGR;

SynB3
                                    (SEQ ID NO: 40)
RRLSYSRRRF;

PTD-4
                                    (SEQ ID NO: 41)
PIRRRKKLRRLK;

PTD-5
                                    (SEQ ID NO: 42)
RRQRRTSKLMKR;

FHV Coat-(35-49)
                                    (SEQ ID NO: 43)
RRRRNRTRRNRRRVR;

BMV Gag-(7-25)
                                    (SEQ ID NO: 44)
KMTRAQRRAAARRNRWTAR;

HTLV-II Rex-(4-16)
                                    (SEQ ID NO: 45)
TRRQRTRRARRNR;

D-Tat
                                    (SEQ ID NO: 46)
GRKKRRQRRRPPQ;

R9-Tat
                                    (SEQ ID NO: 47)
GRRRRRRRRRPPQ;

Transportan
                                    (SEQ ID NO: 48)
GWTLNSAGYLLGKINLKALAALAKKIL chimera;

MAP
                                    (SEQ ID NO: 49)
KLALKLALKLALALKLA;

SBP
                                    (SEQ ID NO: 50)
MGLGLHLLVLAAALQGAWSQPKKKRKV;

FBP
                                    (SEQ ID NO: 51)
GALFLGWLGAAGSTMGAWSQPKKKRKV;

MPG
                                    (SEQ ID NO: 52)
ac-GALFLGFLGAAGSTMGAWSQPKKKRKV-cya;

MPG(?NLS)
                                    (SEQ ID NO: 53)
ac-GALFLGFLGAAGSTMGAWSQPKSKRKV-cya;

Pep-1
                                    (SEQ ID NO: 54)
ac-KETWWETWWTEWSQPKKKRKV-cya;
and Pep-2
                                    (SEQ ID NO: 55)
ac-KETWFETWFTEWSQPKKKRKV-cya.
```

The protein transduction domain may comprise polyarginines, such as RxN (4<N<17) chimera, polylysines, such as KxN (4<N<17) chimera, (RAca)6R, (RAbu)6R, (RG)6R, (RM)6R, (RT)6R. (RS)6R, R10, (RA)6R, R7, or R8.

The protein transduction domain may comprise polyarginine or polylysine. The protein transduction domain may comprise an arginine and lysine repeat sequence. The protein transduction domain may comprise arginine residues, such as consecutive arginine residues. The protein transduction domain may consist essentially of arginine residues. The protein transduction domain may comprise arginine repeats, such as 4-20 arginine residues. The protein transduction domain may comprise 8 arginine residues. The protein transduction domain may comprise between about 6 and about 12 arginine residues. The protein transduction domain may comprise between about 7 and about 9 arginine residues.

The protein transduction domain may comprise between about 4 and about 12 amino acid residues. The protein transduction domain may comprise between about 6 and about 12 amino acid residues. The protein transduction domain may comprise between about 7 and about 9 amino acid residues. The protein transduction domain may comprise at least about 4 amino acid residues. The protein transduction domain may comprise at least about 6 amino acid residues.

The protein transduction domain may comprise lysine residues, such as consecutive lysine residues. The protein transduction domain may consist essentially of lysine residues. The protein transduction domain may comprise lysine repeats, such as 4-20 lysine residues. The protein transduction domain may comprise 8 lysine residues. The protein transduction domain may comprise between about 4 and about 12 lysine residues. The protein transduction domain may comprise between about 6 and about 12 lysine residues. The protein transduction domain may comprise between about 7 and about 9 lysine residues.

The protein transduction domain may comprise Q and R residues, such as consecutive QR repeat residues. The protein transduction domain may consist essentially of Q and R residues. The protein transduction domain may comprise QR repeats, such as 4-20 QR repeat residues. The protein transduction domain may comprise 8 QR repeat residues. The protein transduction domain may comprise between about 6 and about 12 QR repeat residues. The protein transduction domain may comprise between about 7 and about 9 QR repeat residues.

The cargo may be a molecular cargo. The cargo may comprise a protein. The cargo may comprise a peptide. The cargo may comprise a non-small molecule. The cargo may comprise a nanoparticle, such as a metal nanoparticle or polymer nanoparticle. The nanoparticle may be a rod, such as a metal rod. The nano-particle may be porous. The cargo may comprise a nano-structure. The cargo may comprise a superparamagnetic iron oxide nanoparticle (SPION). The cargo may comprise nucleic acid, such as a nucleic acid vector. The cargo may comprise oligonucleotide. The cargo may comprise any of siRNA, modified messenger RNAs (mRNAs), micro RNAs. DNA, PNA, LNA or constructs thereof.

The cargo may comprise a physiologically or metabolically relevant protein. The cargo may comprise an intracellular protein. The cargo may comprise a signal protein, which is a protein involved in a signal pathway. The cargo may comprise a protein involved with regulation of expression or metabolism of a cell. The cargo may comprise a protein involved with cell division. The cargo may comprise a protein involved with cell differentiation, such as stem cell differentiation. The cargo may comprise a protein required for induction of pluripotent stem cells. The cargo may comprise a protein involved with cardiac cell differentiation. The cargo may comprise a marker, such as a protein marker. The cargo may comprise a bacterial, or bacterially derived protein. The cargo may comprise a mammalian, or mammalian derived protein. The cargo may be any peptide, polypeptide or protein. The cargo may comprise research, diagnostic or therapeutic molecules. The cargo may comprise a transcription modulator, a member of signal production. The cargo may comprise an enzyme or substrate thereof, a protease, an enzyme activity modulator, a perturbimer and peptide aptamer, an antibody, a modulator of protein-protein interaction, a growth factor, or a differentiation factor.

The cargo may be a pre-protein. For example, excision domains may be provided in the delivery molecule, which is arranged to be cleaved upon entry or after entry into the cell. The cargo may be a protein arranged to be post-translationally modified within the cell. The cargo may be arranged to be functional once inside the cell. For example, the cargo may not be functional until after transduction into the cell.

The cargo may comprise any intracellular molecule. The cargo may comprise any protein or molecule having an intracellular function (mode of action), intracellular receptor, intracellular ligand, or intracellular substrate. The cargo may comprise a protein or molecule that is naturally/normally internalised into a cell. The cargo may comprise a protein intended for delivery or display in the cell surface, such as a cell surface receptor. The cargo may be selected from any of the group comprising a therapeutic molecule; a drug; a pro-drug; a functional protein or peptide, such as an enzyme or a transcription factor; a microbial protein or peptide; and a toxin; or nucleic acid encoding thereof.

The cargo may be selected from any of the group comprising NANOG, NEO, MYOD, Cre, GATA4, TBX5, BAF60c and NKX2.5. The cargo may comprise RFP. The cargo may comprise Cre. The cargo may comprise a member of the cardiac gene regulatory network. The cargo may comprise GATA4. The cargo may comprise TBX5. The cargo may comprise NKX2.5. The cargo may comprise BAF60c. The cargo may comprise Oct-3/4 (Pou5f1), Sox2, Lin28, Klf4, Nanog, Glis1 or c-Myc; or combinations thereof.

The cargo may be selected from any of the group comprising toxin, hormone transcription factors, such as jun, fos, max, mad, serum response factor (SRF), AP-1, AP2, myb, MyoD, myogenin, ETS-box containing proteins, TFE3, E2F, ATF1, ATF2, ATF3, ATF4, ZF5, NFAT, CREB, HNF4, C/EBP, SP1, CCAAT-box binding proteins, interferon regulation factor (IRF-1), Wilms tumor protein, ETS-binding protein, STAT, GATA-box binding proteins, e.g., GATA-3, transcription factor, such as HIF1a and RUNT, the forkhead family of winged helix proteins, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, isovaleryl-coA dehydrogenase, propionyl CoA carboxylase, methyl malonyl CoA mutase, glutaryl CoA dehydrogenase, beta-glucosidase, pyruvate carboxylate, hepatic phosphorylase, phosphorylase kinase, glycine decarboxylase, H-protein, T-protein, a cystic fibrosis transmembrane regulator (CFTR) sequence, a dystrophin cDNA sequence, Oct-3/4 (Pou5f1), Sox2, c-Myc, Klf4, RPE65 Nanog. and SoxB 1; or fragments thereof, and/or combinations thereof.

The cargo may comprise non-covalently bound complexes such as protein-protein complexes, protein-mRNA, protein-non-coding RNA, protein-lipid and protein-small molecule complexes. Examples of such complexes are RISCs and spliceosomes.

The cargo may have a molecular weight of at least 1 KDa. The cargo may have a molecular weight of at least 5 KDa. The cargo may have a molecular weight of at least 10 KDa. The cargo may have a molecular weight of at least 20 KDa. The cargo may have a molecular weight of 400 KDa or less. The cargo may have a molecular weight of 300 KDa or less. The cargo may have a molecular weight of between about 0.5 KDa and about 400 kDa. The cargo may have a molecular weight of between about 1 KDa and about 400 kDa. The cargo may have a molecular weight of between about 0.5 KDa and about 200 kDa. The cargo may have a molecular weight of between about 1 KDa and about 200 kDa. The cargo may have a molecular weight of between about 2 KDa and about 300 kDa. The cargo may have a molecular weight of between about 20 KDa and about 300 kDa. The cargo may have a molecular weight of between about 20 KDa and about 100 kDa.

Where the cargo comprises amino acids, the cargo may be between about 20 and about 30,000 amino acids in length. The cargo may be between about 20 and about 10,000 amino acids in length. The cargo may be between about 20 and about 5,000 amino acids in length. The cargo may be between about 20 and about 1000 amino acids in length. The cargo may be at least about 20 amino acids in length. The cargo may be at least about 100 amino acids in length.

The cargo may be capable of binding, such as ionic or covalent binding, to the cargo-binding molecule. The cargo may be capable of binding, such as ionic or covalent binding, to the protein transduction domain and/or GAG binding element.

The cargo may comprise an element for binding to the cargo-binding molecule. The cargo may comprise biotin, or alternatively streptavidin. The cargo may be biotinylated. The cargo may comprise an affinity tag capable of binding to a complementary affinity tag on the cargo-binding molecule.

In one embodiment the cargo is bound to the cargo-binding molecule. The cargo may be bound to the cargo-binding molecule during manufacture of the delivery molecule, post-manufacture, prior to use, or during use.

The cargo-binding molecule may be a carrier for the cargo molecule. A single cargo-binding molecule may bind and carry multiple cargo molecules. The cargo-binding molecule may protect the cargo prior to internalisation into a cell. The cargo-binding molecule may be capable of binding to biotin on a biotinylated cargo. The cargo-binding molecule may be capable of binding to nucleic acid-based cargo. The cargo-binding molecule may be capable of binding to a peptide-based cargo. The cargo-binding molecule may be capable of binding to an antibody cargo, or fragment or mimetic thereof. The cargo-binding molecule may be capable of binding to a nanoparticle cargo, such as a metal or polymer nanoparticle. The cargo-binding molecule may be functionally inactive in a cell, but can carry or bind to an active cargo. The cargo-binding molecule may comprise a chemical linker molecule. The cargo-binding molecule may comprise an affinity tag. The cargo-binding molecule may comprise a peptide or protein. The cargo-binding molecule may comprise mSA2 (monomeric streptavidin 2). The cargo-binding molecule may comprise a nucleic acid interacting peptide, such as LK15. The cargo-binding molecule may comprise an antibody binding molecule, such as an IgG binding protein. The IgG binding protein may comprise *S. aureus* IgG binding protein SpAB. The skilled person will understand that any suitable pairs or groups of molecules may be used for the cargo and cargo-binding molecule provided that they have sufficient binding or affinity between them.

The bond or interaction between the cargo and the cargo-binding molecule may be reversible, or degradeable, for example in the intracellular environment.

The GAG binding element and protein transduction domain may be bound to the cargo and/or cargo-binding molecule by direct chemical conjugation or through a linker molecule. The GAG binding element and protein transduction domain may be bound to the cargo by direct chemical conjugation or through a linker molecule. The GAG binding element and protein transduction domain may be bound to the cargo-binding molecule by direct chemical conjugation or through a linker molecule. The GAG binding element, protein transduction domain and cargo may be a single fusion molecule (e.g. it may be encoded and transcribed as a single peptide molecule). The GAG binding element, protein transduction domain and cargo-binding molecule may be a single fusion molecule (e.g. it may be encoded and transcribed as a single peptide molecule). The protein transduction domain and GAG binding element may flank the cargo-binding molecule and/or cargo.

The delivery molecule may be between about 10 and about 30,000 amino acids in length. The delivery molecule may be between about 20 and about 30,000 amino acids in length. The delivery molecule may be between about 30 and about 30,000 amino acids in length. The delivery molecule may be between about 40 and about 30,000 amino acids in length. The delivery molecule may be between about 10 and about 10,000 amino acids in length. The delivery molecule may be between about 20 and about 10,000 amino acids in length. The delivery molecule may be between about 40 and about 10,000 amino acids in length. The delivery molecule may be between about 10 and about 3,000 amino acids in length. The delivery molecule may be between about 20 and about 3,000 amino acids in length. The delivery molecule may be between about 40 and about 3,000 amino acids in length. The delivery molecule may be between about 10 and about 1000 amino acids in length. The delivery molecule may be between about 20 and about 1000 amino acids in length. The delivery molecule may be between about 40 and about 1000 amino acids in length. The delivery molecule may be between about 40 and about 500 amino acids in length. The delivery molecule may be between about 10 and about 500 amino acids in length. The delivery molecule may be between about 20 and about 500 amino acids in length. The delivery molecule may be between about 100 and about 3,000 amino acids in length. The delivery molecule may be at least about 100 amino acids in length.

The delivery molecule may be a single fusion molecule. The cargo, HS-GAG binding element, and protein transduction domain may be fused together. The HS-GAG binding element and protein transduction domain may flank the cargo. The cargo, HS-GAG binding element, and protein transduction domain may be linked together by one or more linker molecules.

The delivery molecule may have a molecular weight of at least 1 KDa. The delivery molecule may have a molecular weight of at least 5 KDa. The delivery molecule may have a molecular weight of at least 10 KDa. The delivery molecule may have a molecular weight of at least 20 KDa. The delivery molecule may have a molecular weight of 400 KDa or less. The delivery molecule may have a molecular weight of 300 KDa or less. The delivery molecule may have a molecular weight of between about 0.5 KDa and about 400 kDa. The delivery molecule may have a molecular weight of between about 1 KDa and about 400 kDa. The delivery molecule may have a molecular weight of between about 0.5 KDa and about 200 kDa. The delivery molecule may have a molecular weight of between about 1 KDa and about 200 kDa. The delivery molecule may have a molecular weight of between about 2 KDa and about 300 kDa. The delivery molecule may have a molecular weight of between about 20 KDa and about 300 kDa. The delivery molecule may have a molecular weight of between about 20 KDa and about 100 kDa.

The cell may be a mammalian cell, such as a human cell. The cell may be a cancerous cell. The cell may be a stem cell. The cell may be a mutant cell. The cell may comprise a population of cells. The population of cells may be a mixed population of cell types. The cell may be a mesenchymal stem cell. The cell may be an embryonic stem cell. The cell may be a pluripotent stem cell. The cell may be a cell requiring functional restoration. The cell may be a cardiac stem cell. The cell may be selected from any of the group comprising NIH3t3, CGR8, and HUES7.

The delivery molecule may comprise a marker for identifying and/or tracking the location of the delivery molecule. The marker may comprise a fluorescence marker, or a radioisotope. The marker may comprise mRFP1 (monomeric red fluorescent protein). The marker may comprise mNectarine, such as pH-sensitive mNectarine. mNectarine, is appropriate to measure physiological pH changes in mammalian cells, because it has a pKa' of 6.9. The marker may comprise a red fluorescent protein (RFP) homologue of avGFP. The marker may comprise a fluorescent protein selected from the mFruit series RFPs, derived from tetrameric Discosoma RFP. The marker may comprise any of mTangerine, mOrange, mCherry, mStrawberry, yellow FP Citrine. mApple and TagRFP-T. The marker may be pH-sensitive. The marker may be used to confirm delivery of the delivery molecule into the cell or tissue. The marker may be cell-type specific, for example the marker may only be activated or fluoresce in specific cell types.

The delivery molecule may comprise a tag to aid in purification, isolation, detection and/or determination of location. The tag may be an affinity tag. The tag may be a peptide. The tag may be a FLAG-tag/FLAG octapeptide.

The delivery molecule may be encoded by a nucleotide sequence comprising SEQ ID NO: 10.

According to another aspect of the invention, there is provided a method of producing a delivery molecule for transduction comprising the steps of:
(i) fusing a cargo with a GAG binding element, which is capable of binding to GAG on the surface of the cell; and
a protein transduction domain; or
(ii) combining nucleic acid encoding a cargo with nucleic acid encoding a GAG binding element and a protein transduction domain, and expressing the delivery molecule from the nucleic acid; or
(iii) synthesising in vitro a cargo with a GAG binding element, which is capable of binding to GAG on the surface of the cell; and
a protein transduction domain.

The nucleic acid encoding the GAG binding element and the protein transduction domain may be DNA. The synthesis in vitro may comprise liquid or solid phase synthesis of peptide. The GAG binding element may be a HS-GAG binding element.

According to another aspect of the invention, there is provided a method of transducing a cargo into a cell comprising:
providing a delivery molecule according to the invention; and
contacting the cell with the delivery molecule.

The transduction may be for at least about 1 second. The transduction may be for at least about 1 minute. The transduction may be for at least about 2 minutes. The transduction may be for at least about 10 minutes. The transduction may be for at least about 30 minutes. The transduction may be for at least about 1 hour. The transduction may be for 12 hours or less, such as 8 hours or less. The transduction may be for about 6 hours or less. The transduction may be for between about 1 hour and 6 hours. The transduction may be for less than about 1 hour. The transduction may be for less than about 30 minutes. The transduction may be for less than about 10 minutes. The transduction may be for less than about 1 minute.

According to another aspect of the present invention, there is provided a cell transduced, or induced, by the method of the invention, or by the delivery molecule of the invention.

According to another aspect of the present invention, there is provided a cell comprising or encoding the delivery molecule in accordance with the invention.

The cell may be an induced pluripotent stem cell.

According to another aspect of the present invention, there is provided a nucleic acid encoding the delivery molecule according to the invention.

The nucleic acid may be DNA. The nucleic acid may be a vector.

According to another aspect of the present invention, there is provided a vector for expression of a protein for transduction comprising
a sequence encoding a GAG binding element, such as a HS-GAG binding element; and
a sequence encoding protein transduction domain.

The vector may comprise a nucleic acid sequence encoding a molecule. The vector may comprise a bacterial replication element, such as OriP. The vector may comprise a multiple restriction/cloning site. The vector may comprise a strong promoter. The vector may comprise a marker, such as an antibiotic resistance marker.

According to another aspect of the present invention, there is provided a cell comprising: the nucleic acid according to the invention; or a vector according to the invention.

According to another aspect of the present invention, there is provided a process for the production of a delivery molecule for transduction comprising:
expressing the delivery molecule from the cell according to the invention; and substantially or partially isolating or purifying the delivery molecule.

The isolation or purification of the delivery molecule may be from the cell(s), or from the cell supernatant. The isolation or purification of the delivery molecule may be from the host cell protein (HCP). The skilled person may isolate or purify the delivery molecule from the cell by any standard purification method.

The delivery molecule may be produced in a cell, such as a mammalian, insect, yeast or bacterial cell. The delivery molecule may be produced in a mammalian cell. The cell may be HeLa, CHO, or HEK293T.

According to another aspect of the invention, there is provided a method of modifying a cargo for enhancing the cargo's transduction into a cell, comprising the provision of a HS-GAG binding element and a protein transduction domain bound to the cargo.

The HS-GAG binding element, protein transduction domain and cargo may be provided by protein expression as a single fusion molecule. The HS-GAG binding element, protein transduction domain and cargo may be provided by chemically bonding them together.

The chemical bonding may be covalent bonding The HS-GAG binding element, protein transduction domain and cargo may be provided by fusing them together, for example using SNAP-tag. Halo tag (Promega), or CLIP-tag technologies (New England Biolabs).

According to another aspect of the present invention, there is provided the use of a HS-GAG binding element and a protein transduction domain for chaperoning a cargo into a cell by transduction.

According to another aspect of the present invention, there is provided a method of treatment or prevention of a disease comprising administering a composition comprising a delivery molecule in accordance with the invention.

According to another aspect of the present invention, there is provided a method of treatment or prevention of a disease comprising administering a cell in accordance with the invention.

According to another aspect of the present invention, there is provided a delivery molecule according to the invention for use in the treatment or prevention of a disease.

The disease may be any disease characterised by a protein deficiency in one or more cells. The disease may comprise a cardiac condition, such as a heart disorder. The disease may comprise a disease treatable or preventable by the administration of differentiated stem cells. The disease may comprise a disease treatable or preventable by the administration of induced pluripotent stem cells. The disease may comprise a disease treatable or preventable by protein transduction. The treatment may comprise regeneration of heart tissue, or restoration of heart tissue function. The disease may comprise cancer or muscular dystrophy.

The delivery molecule may be used for (a) inhibiting smooth muscle cell proliferation and/or migration; (b) promoting smooth muscle relaxation; (c) increasing the contractile rate in heart muscle; (d) increasing the rate of heart muscle relaxation; (e) promoting wound healing; (f) reducing scar formation; (g) disrupting focal adhesions; (h) regulating actin polymerization; or (i) treating, preventing or inhibiting one or more of intimal hyperplasia, stenosis, restenosis, atherosclerosis, smooth muscle cell tumors, smooth muscle spasm, angina, Prinzmetal's angina (coronary vasospasm), ischemia, stroke, bradycardia, hypertension, pulmonary (lung) hypertension, asthma (bronchospasm), toxemia of pregnancy, pre-term labor, pre-eclampsia/eclampsia, Raynaud's disease or phenomenon, hemolytic-uremia, non-occlusive mesenteric ischemia, anal fissure, achalasia, impotence, female sexual arousal disorder (FSAD), migraine, ischemic muscle injury associated with smooth muscle spasm, vasculopathy, such as transplant vasculopathy, bradyarrythmia, bradycardia, congestive heart failure, stunned myocardium, pulmonary hypertension, muscular dystrophy, channelopathy and diastolic dysfunction.

According to another aspect of the present invention, there is provided a method of modifying cellular function in a subject or a cell culture comprising administering a composition comprising a delivery molecule in accordance with the invention.

The cell culture may be in vitro.

According to another aspect of the present invention, there is provided a method of inducing differentiation of a cell by transduction of a delivery molecule according to the invention into a stem cell.

The stem cell may comprise a cardiac stem cell. The delivery molecule may comprise GATA4 or TBX5.

According to another aspect of the present invention, there is provided a method of inducing a pluripotent stem cell by transduction of a delivery molecule according to the invention into a non-pluripotent cell. The delivery molecule may comprise Oct-3/4 (Pou5f1), Sox2, Lin28, Klf4, Nanog, Glis1 or c-Myc; or combinations thereof.

According to another aspect of the present invention, there is provided a method of inducing cardiac differentiation by transduction of a first delivery molecule according to the invention into a cardiac stem cell, and transduction of a second delivery molecule according to the invention into the cardiac stem cell, wherein the first delivery molecule comprises GATA4 and the second delivery molecule comprises TBX5.

The method of inducing cardiac differentiation of a stem cell may further comprises transduction of one or more fusion proteins comprising a cargo selected from any of the group comprising GATA4, TBX5. NKX2.5, and BAF60c. The method of inducing cardiac differentiation of a stem cell may further comprises transduction of one or more fusion proteins comprising a protein of the cardiac gene regulatory network. The transduction into the cardiac stem cell may be concurrent or sequential.

According to another aspect of the present invention, there is provided a pharmaceutical composition comprising a delivery molecule according to the invention, and a pharmaceutically acceptable excipient.

The delivery molecule may be transduced in the presence of, or co-administered with a vesicle release agent for promoting release of the delivery molecule from micropinocytic vesicles. The vesicle release agent may comprise chloroquine. The chloroquine concentration may be between about 1 µM and about 100 µM.

According to another aspect of the present invention, there is provided a method of cell imaging comprising the delivery of the delivery molecule according to the invention into a cell, wherein the cargo comprises a nanoparticle.

The nanoparticle may comprise metal or polymer. The nanoparticle may be a rod.

According to another aspect of the present invention, there is provided a method of gene therapy comprising the delivery of the delivery molecule according to the invention into a cell, wherein the cargo comprises nucleic acid.

Advantageously, the transduction may be monitored, or capable of being monitored in real time.

The delivery molecule may be arranged to target (i.e. deliver cargo to) specific cell types.

An appropriate GAG binding element may be chosen to target a specific population of cells having the corresponding GAG type on the cell surface.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1 Inefficient Protein Delivery in Pluripotent Cells. (a) Schematic of the proteins created to determine the efficiency of protein delivery. mR is mRFP only as a poorly transducing control protein representing background transduction. mR-8R is mRFP with a C-terminal fusion of eight Arginine residues (8R) to promote transduction. (b) mR-8R transduces efficiently into NIH3t3 cells. Fluorescence microscopy images of NIH3t3 cells treated with mR or mR-8R (100 µg/ml) for twelve hours in standard media conditions. Scale bar, 100 µm. (c) mR-8R transduces inefficiently into human and mouse embryonic stem cells (HUES7 and CGR-8, respectively), human induced pluripotent stem cells (IPS2) and mouse cardiomyocyte cell line HL1. Fluorescence microscopy images of multiple cell lines treated with mR-8R (100 µg/ml) for twelve hours in cell-type specific media conditions. Scale bar, 100 µm. (d) Flow cytometry analyses of the multiple cell lines treated with different dosages of mR-8R (0, 1, 5, 10, 20, 50 and 100 µg/ml) for twenty-four hours. (e) Flow cytometry analyses of the 100 µg/ml dose for twenty-four hours. Graphs show relative fluorescence units (R.F.U.). Error bars indicate s.d.

Figure 2:
Figure 2:
Figure 2:
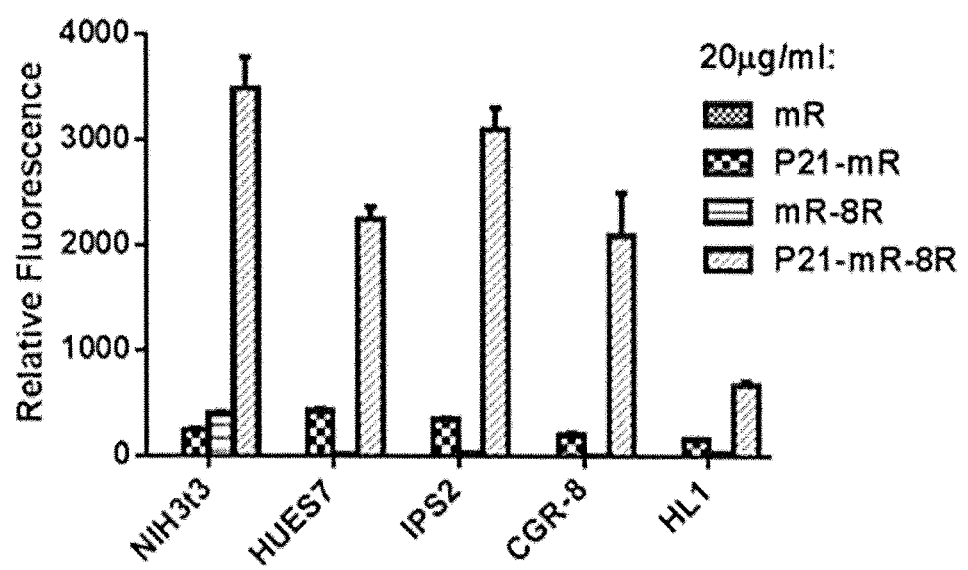
Figure 2:
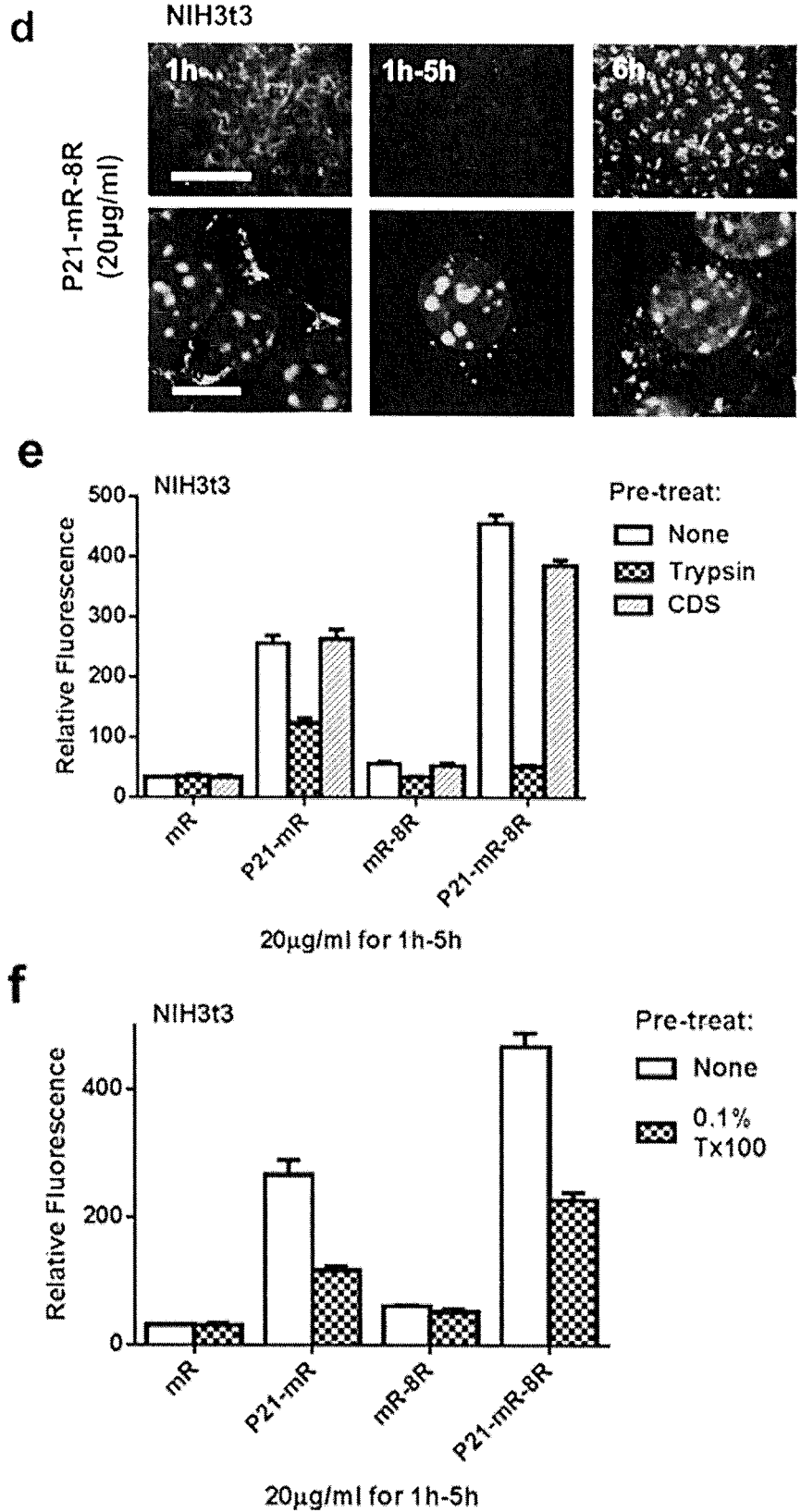

FIG. 2 P21 improves PTD-mediated transduction. (a) Schematic of the proteins created after screening domains which improve efficiency of protein delivery to cells. mR and mR-8R are described in FIG. 1. P21-mR is mRFP with an N-terminal fusion of the P21 domain of heparin-binding EGF (HB-EGF). P21-mR-8R is mRFP with N-terminal fusion of P21 and C-terminal fusion of 8R. (b) Fusion of P21 to mR-8R significantly improves transduction into NIH3t3 cells. Fluorescence microscopy images of NIH3t3 cells treated with proteins (20 µg/ml) for twelve hours in standard media conditions. Scale bar, 100 µm. (c) P21-mR-8R transduces efficiently into human and mouse embryonic stem cells (HUES7 and CGR-8, respectively) and human induced pluripotent stem cells (IPS2) and mouse cardiomyocyte cell line HL1. Flow cytometry analyses of the mR-8R-inefficiently transduced cell lines treated with proteins mR-8R (20 µg/ml) for twelve hours. (d) P21-mR-8R initially strongly interacts with cell membranes and progressively transduces be localised peri-nuclearly. Fluorescence (top) and confocal laser scanning microscopy (bottom) images of NIH3t3 cells treated with P21-mR-8R (20 µg/ml) for either 1 hour, 1 hour with washes and a further 5 hours incubation (in serum-free media) or 6 hours treatment. Cells were pre-incubated for 1 hour in serum-free media, transduced for the desired time in serum-free media. Scale bars, 50 µm (top) and 10 µm (bottom). (e) Enhancement of transduction mediated by P21 and 8R are affected by Trypsin proteolysis. Flow cytometry analyses NIH3t3 cells treated with proteins (20 µg/ml) for 1 hour and a further 5 hour incubation (in serum-free media), with or without 10 min pre-digestion with Trypsin or treatment with non-proteolytic cell dissociation solution (CDS). Cells were pre-incubated for 1 hour in serum-free media, treated with Trypsin and transduced for 1 hour in serum-free media. (f) Cell surface interaction of P21-containing proteins is disrupted by Tritonx100 treatment. Flow cytometry analyses NIH3t3 cells treated with proteins (20 g/ml) for 1 hour and a further 5 hour incubation (in serum-free media) with 10 min pre-treatment of PBS or PBS containing 0.1% (v/v) Tritonx100 (Tx100). Cells were pre-incubated for 1 hour in serum-free media, treated with PBS or PBS with Tx100 and transduced for 1 hour in serum-free media. Error bars indicate s.d.

Figure 3:
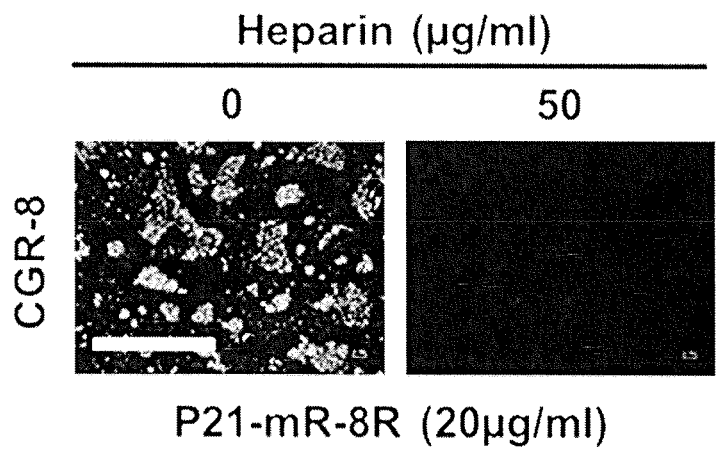
Figure 3:
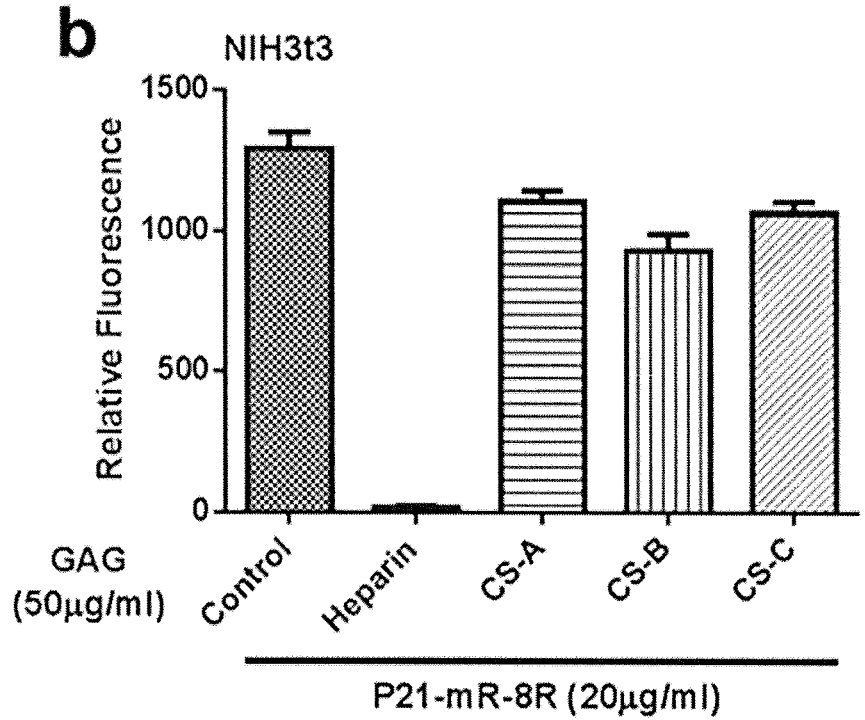
Figure 3:
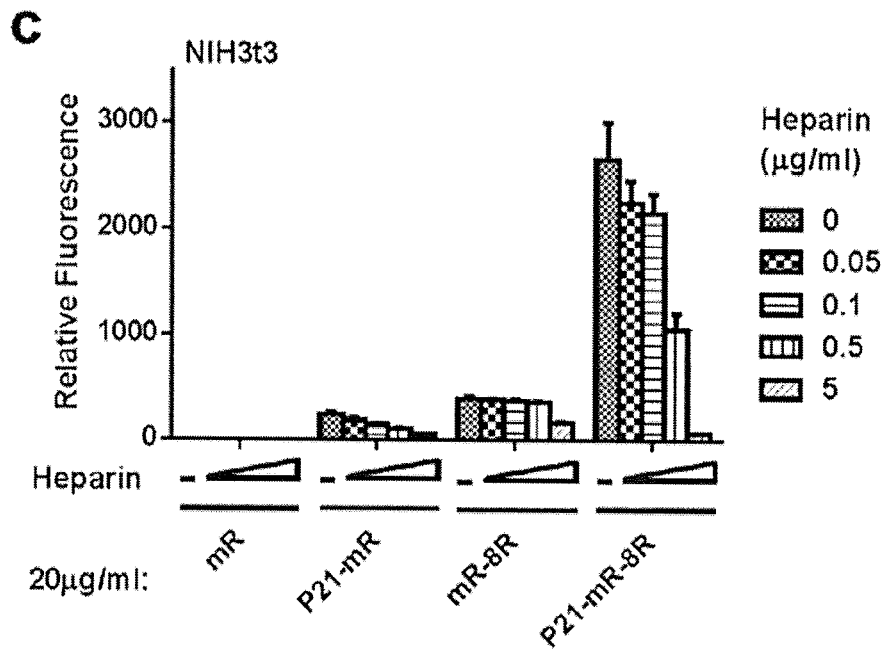
Figure 3:
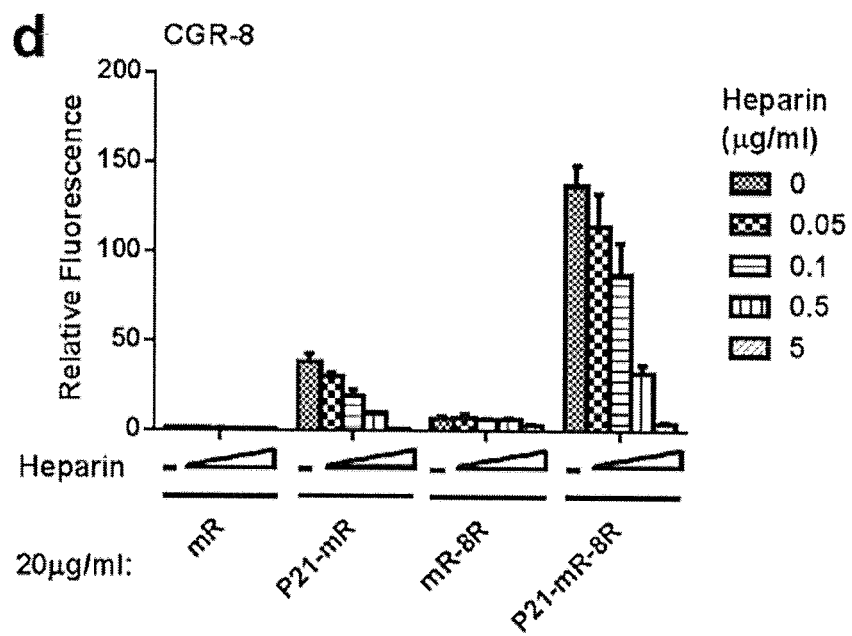
Figure 3:
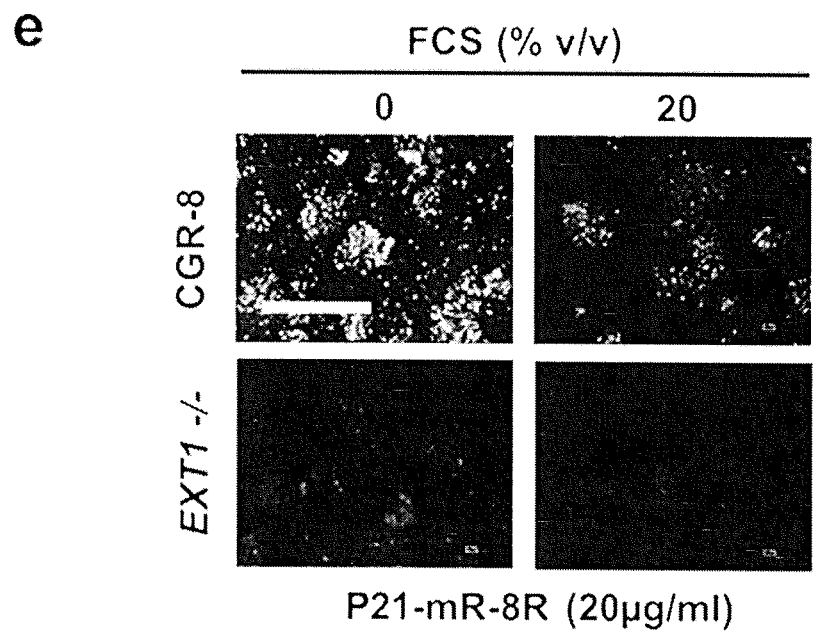
Figure 3:
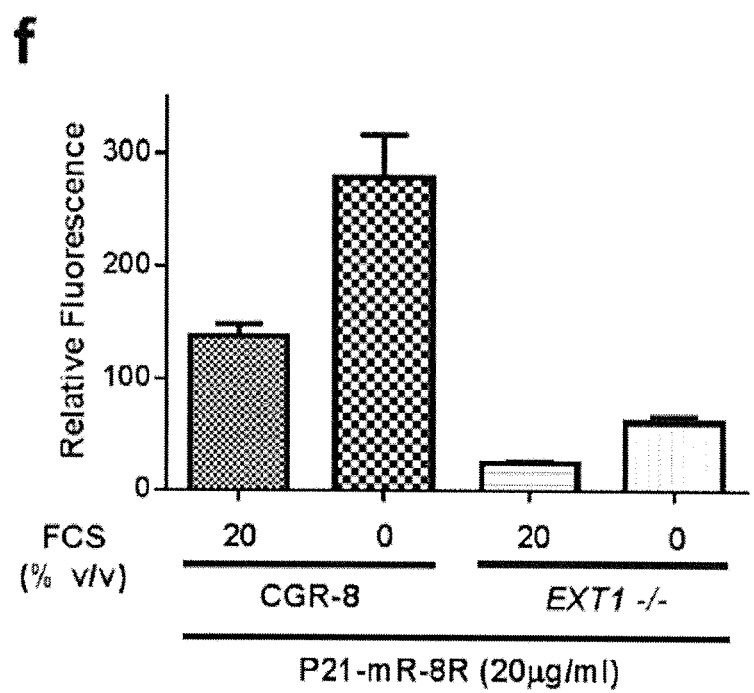

FIG. 3 P21 binds directly to Heparin and cell surface HS-GAG. (a) Soluble Heparin in media during transduction inhibits cell membrane interaction and transduction of P21-containing proteins. Fluorescence microscopy images of CGR-8 cells treated with P21-mR-8R (20 μg/ml) for 6 hours in serum-free media containing 0 or 50 μg/ml Heparin. Scale bar, 100 μm. (b) Flow cytometry analyses NIH3t3 cells treated with P21-mR-8R (20 μg/ml) for 6 hours with or without a variety of GAGs (50 μg/ml) in serum-free medium. CS is Chondroitin sulphate. Cells were pre-incubated for 1 hour in serum-free media and transduced for 6 hours in serum-free media with or without GAGs. (c-d) Only high-doses of Heparin inhibit 8R activity whereas P21 activity is inhibited dose-dependently by Heparin in (c) NIH3t3 cells and (d) CGR-8 cells. (e) and (f) Cell surface Heparan sulphate is required for efficient P21-mediated protein delivery. Heparan sulphates/Heparin-containing FCS inhibits P21-mediated transduction but can also replace cell surface GAGs and mediate P21-transduction in cells deficient for Heparan sulphate. Fluorescence microscopy images of CGR-8 cells and EXT1−/− mESCs treated with P21-mR-8R (20 μg/ml) for 6 hours in media containing 0 or 20% FCS. Scale bar, 100 m. Error bars indicate s.d.

Figure 4:
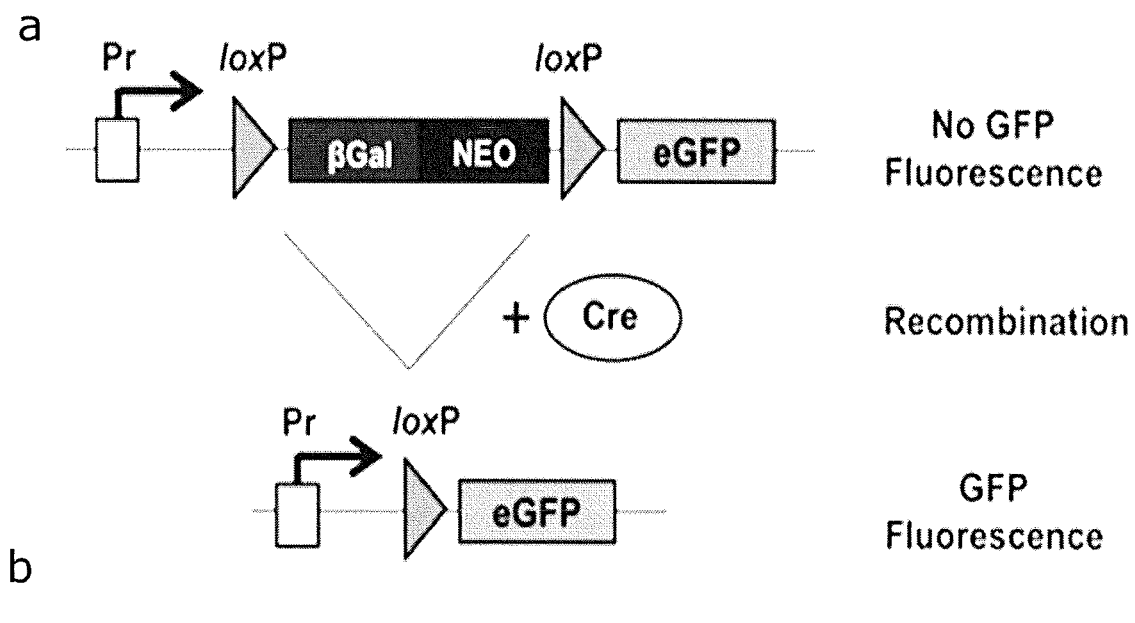
Figure 4:
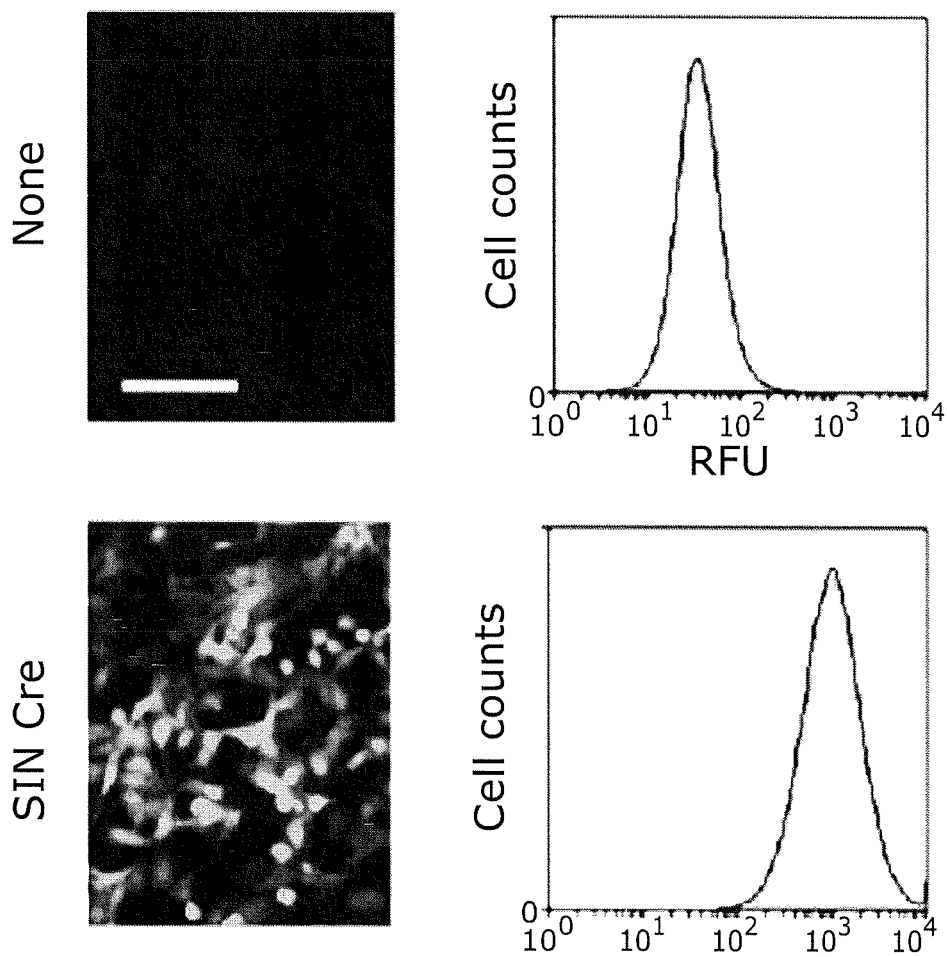
Figure 4:
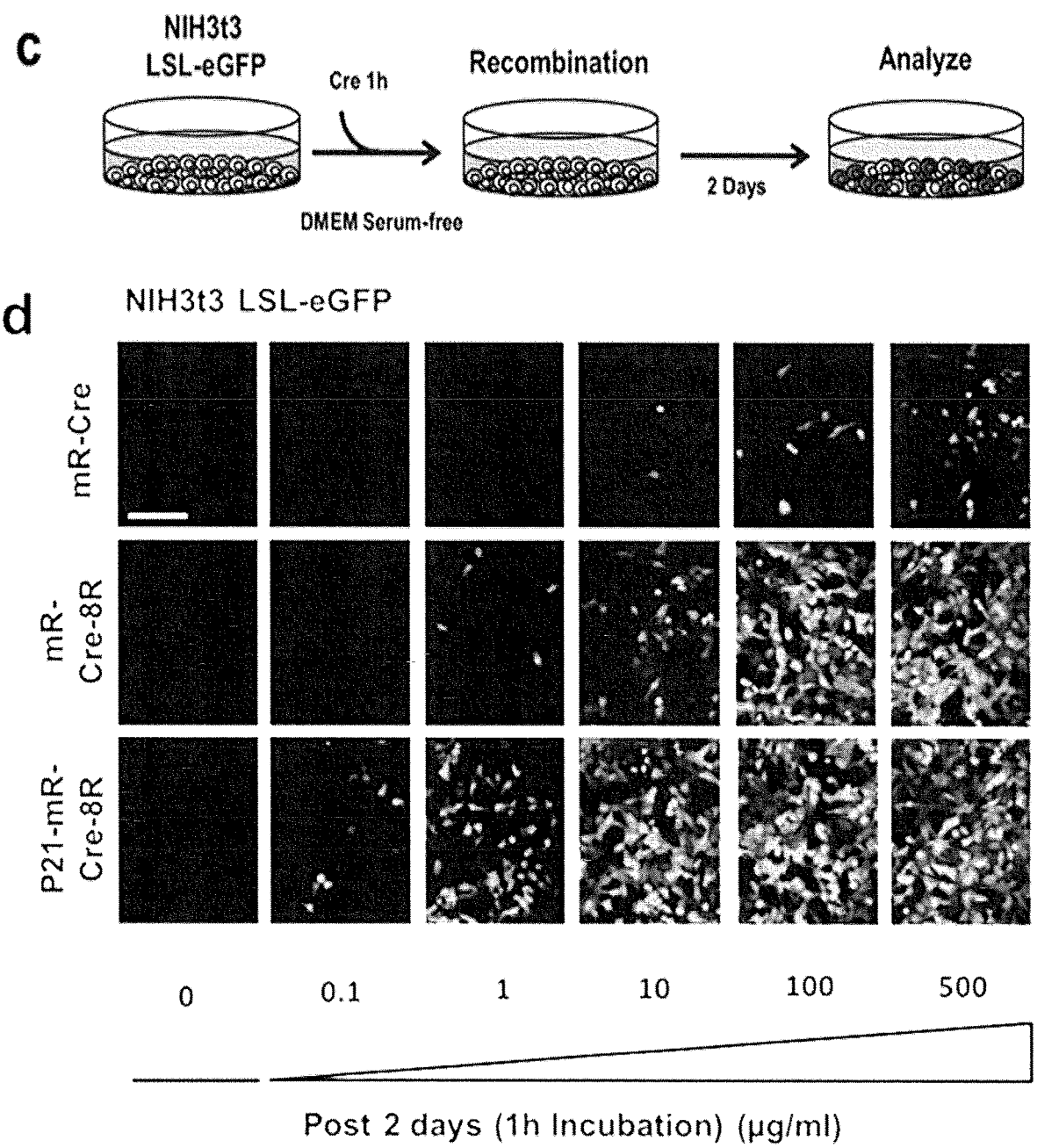
Figure 4:
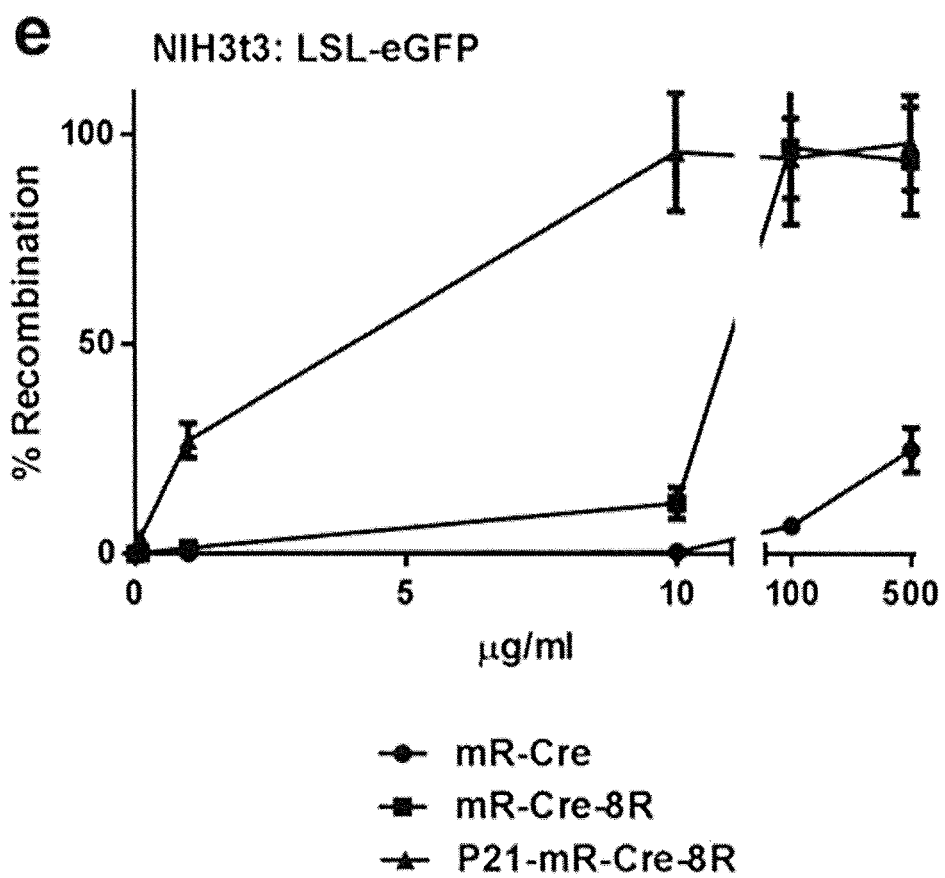

FIG. 4 GET/HETD-mediated nuclear delivery of Cre Recombinase. (a) Schematic of the construct created to mark Cre activity in cells. Cre-mediated excision of a transcriptional STOP region flanked by loxP sites induces the constitutive expression of eGFP. Pr, promoter; βGal, β-galactosidase; Neo, Neomycin phosphotransferase. The NIH3t3 LSL-eGFP cell line was created by transfection and selection of NIH3t3 cells. (b) eGFP expression in untreated NIH3t3 LSP-eGFP cells or those transduced with SIN Cre lentivirus. Left shows fluorescence microscopy and right shows flow cytometry histogram of eGFP expression. Scale bar, 50 μm (c) Scheme of testing transduction of Cre activity in NIH3t3 LSL-eGFP cells. Cells were transduced with Cre proteins for 1 hour, washed and cultured for 2 days before analyses. (d-e) P21-mR-Cre-8R is efficiently transduced and recombines DNA. (d) Fluorescence microscopy images Cre-transduced NIH3t3 LSL-eGFP with the variety of dosages. Scale bar, 50 μm. (e) Flow cytometry analyses of NIH3t3 LSL-eGFP cells transduced for 1 hour with mR-Cre, mR-Cre-8R and P21-mR-Cre-8R at a variety of dosages (0, 1, 10, 100 and 500 μg/ml), washed and cultured for 2 days. Graph shows % recombination (i.e. % of eGFP+ve from total cell population). Error bars indicate s.d.

Figure 5:
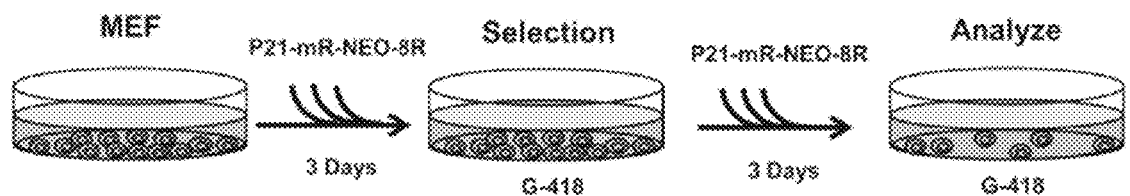
Figure 5:
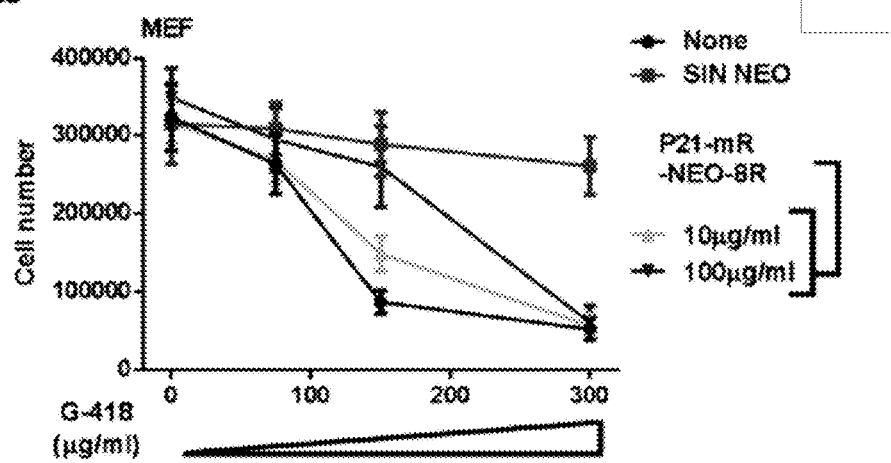
Figure 5:
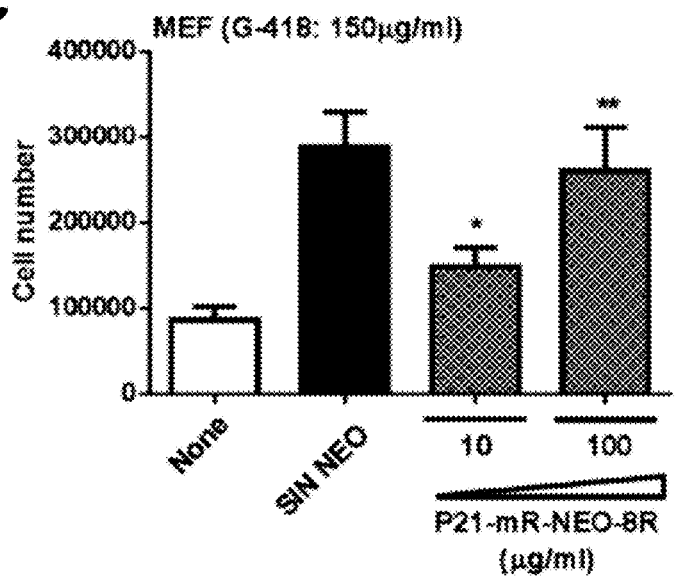
Figure 5:
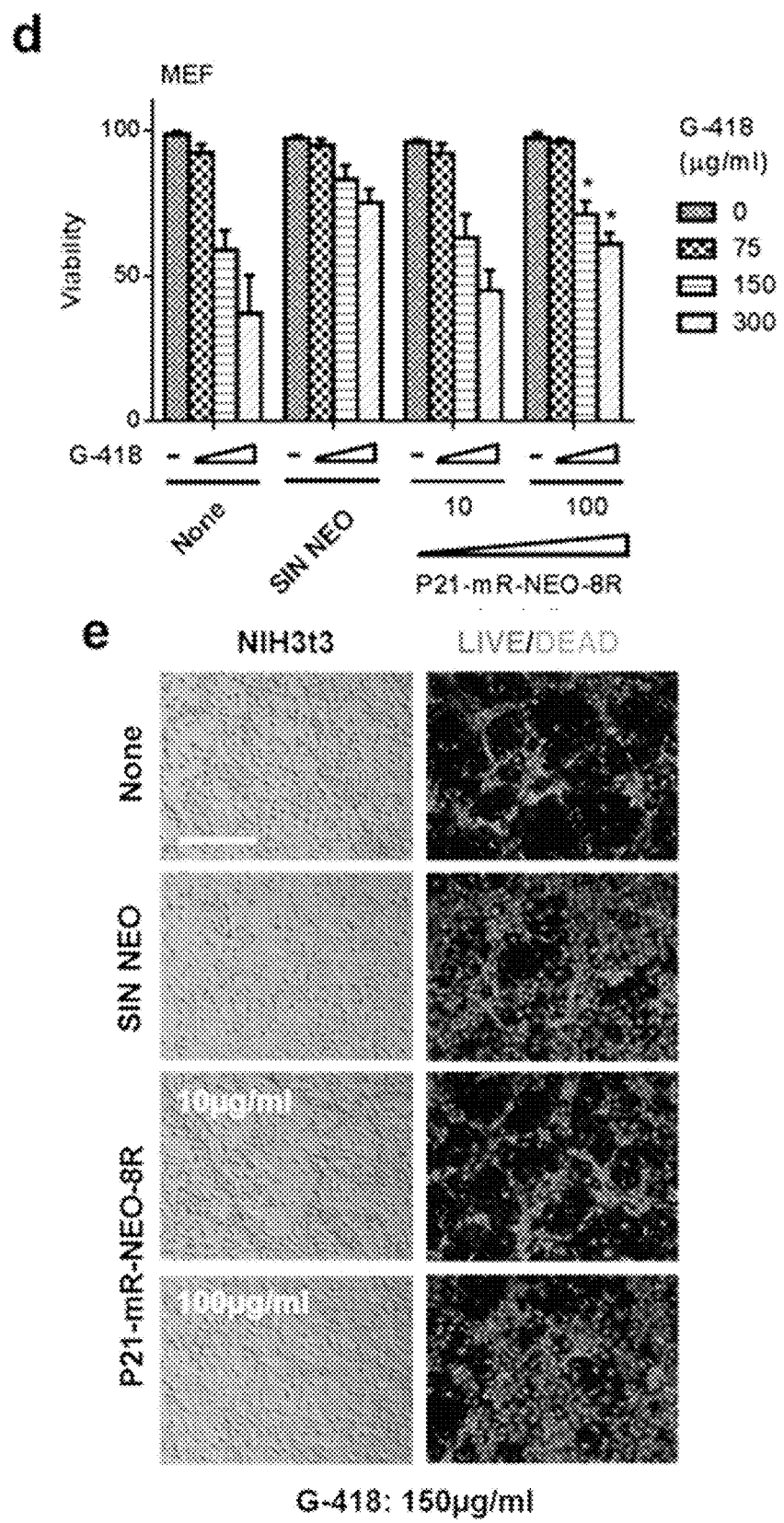

FIG. 5 GET/HETD-mediated delivery of NEO promotes antibiotic-resistance in mouse embryonic fibroblasts. (a) Scheme of testing the antibiotic-resistance activity of transduced NEO (Neomycin Phosphotransferase) in mouse embryonic fibroblast (MEF) cells. MEF cells (300,000) were cultured in DMEM containing 10% (v/v) FCS and P21-mR-NEO-8R (0, 10 or 100 μg/ml) for 3 days feeding with fresh media daily. G-418 was then added to media for a further 3 days with daily feeding of fresh media. (b-e) P21-mR-NEO-8R rescues MEF and NIH3t3 cells from G-418 selection by conferring antibiotic-resistance. (b-c) P21-mR-NEO-8R maintains living cultures of MEFs under G-418 selection. (b) MEF cell numbers when supplemented with SIN NEO (to overexpress NEO) or transduced with P21-mR-NEO-8R and selected with G-418 (0, 75, 150 or 300 μg/ml). (c) MEF cell numbers for the 150 μg/ml dose of G-418. Error bars indicate s.d. (d-e) P21-mR-NEO-8R promotes viability in G-418 selected MEF and NIH3t3 cells. (d) Quantitation of the percentage of viable MEF cells using Trypan Blue staining. (e) Fluorescence microscopy of NIH3t3 cells selected with 150 μg/ml G-418 assessed for viability using LIVE/DEAD staining. Scale bar, 100 μm. Error bars indicate s.d.

Figure 6:
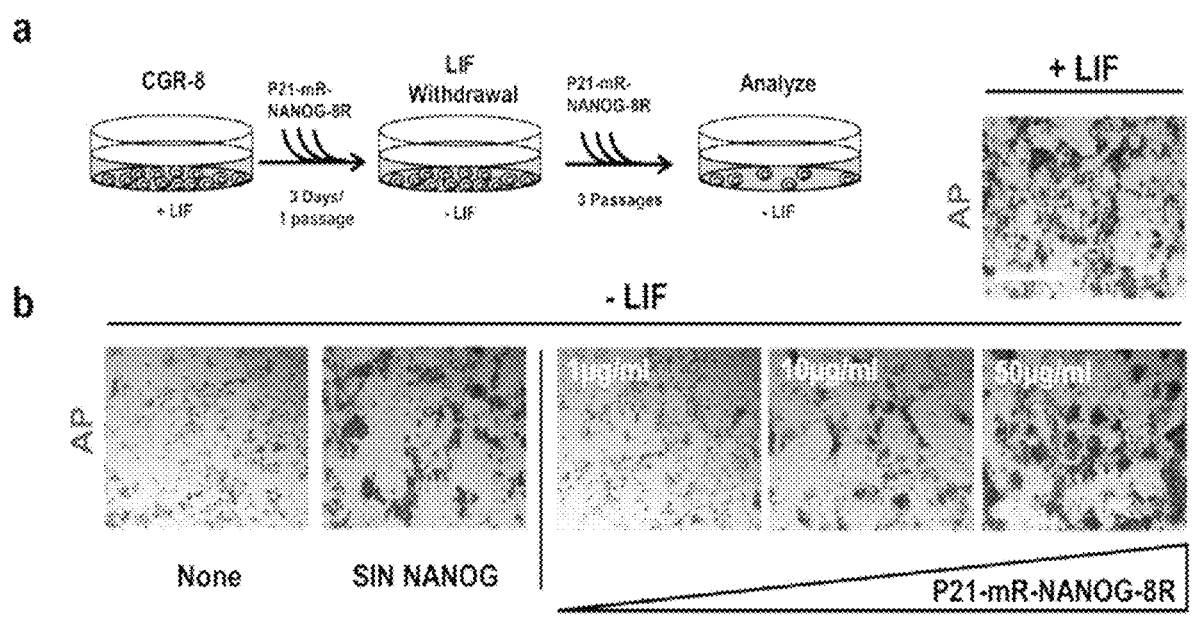
Figure 6:
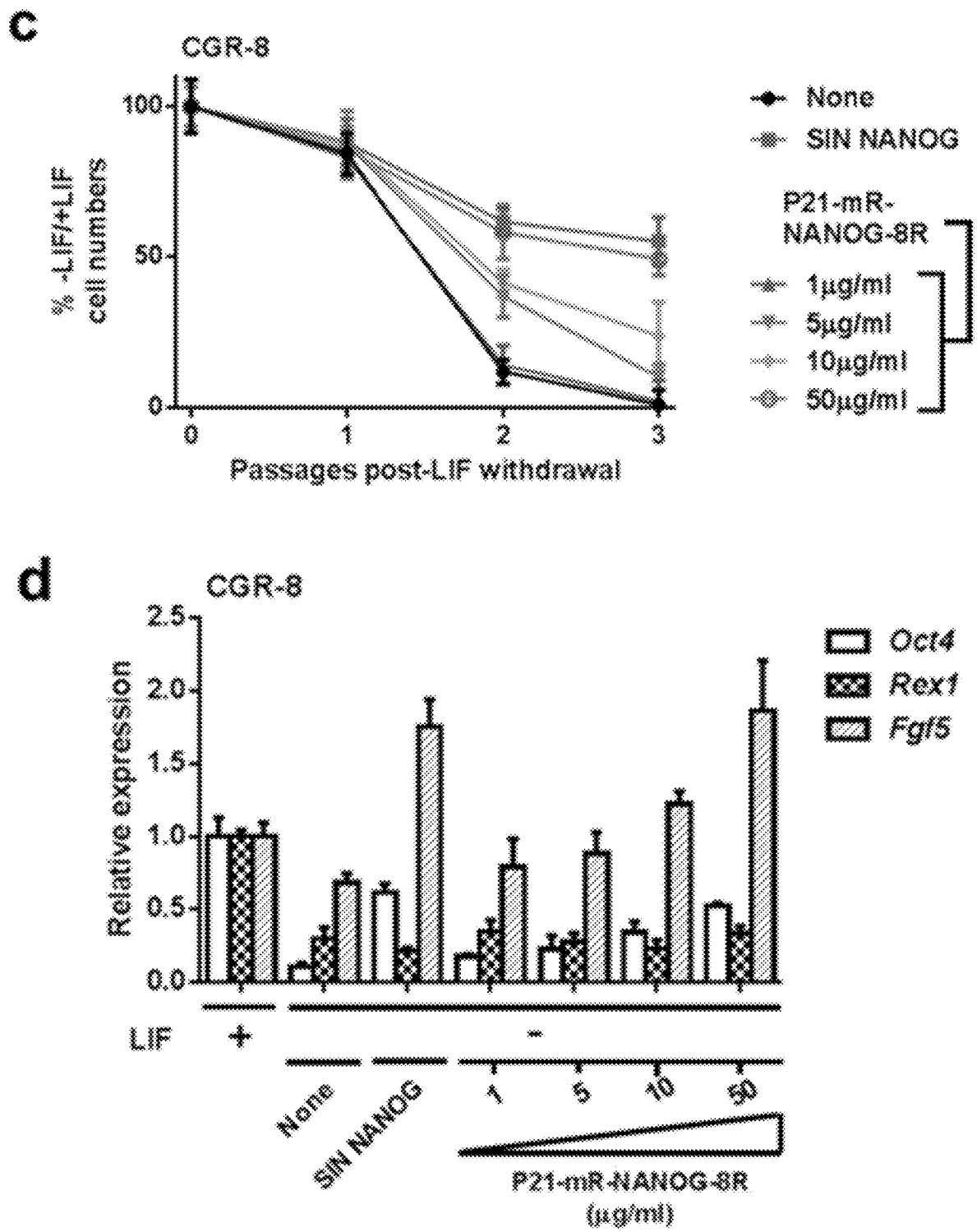

FIG. 6 GET/HETD-mediated delivery of NANOG promotes the Self-renewal of mouse Embryonic Stem cells. (a) Scheme of testing activity of transduced NANOG in CGR-8 cells. Cells were transduced with P21-mR-NANOG-8R proteins (0, 1, 10 and 50 μg/ml) for three consecutive days (1 passage, 1:3 split), passaged 1:3 and plated into growth media with P21-mR-NANOG-8R but lacking LIF (−LIF). Cells were fed daily with −LIF media containing P21-mR-NANOG-8R and passaged 1:3 every 3 days for 2 passages (a total of 3 passages −LIF) (b) P21-mR-NANOG-8R rescues self-renewal of mESCs lacking LIF dose dependently. Alkaline phosphatase (AP) staining of CGR-8 cells treated with P21-mR-NANOG-8R proteins and LIF withdrawal. AP activity and colony morphology is retained in CGR-8 cells cultured in LIF or without LIF but supplemented with SIN NANOG (to overexpress NANOG) or transduced with P21-mR-NANOG-8R. Scale bar, 100 m. (c) P21-mR-NANOG-8R maintains the proliferation of mESCs lacking LIF dose dependently. Percentage of the number of CGR-8 cells cultured without LIF verses those with LIF (% −LIF/+LIF) at passaging. In LIF-deficient CGR-8 cultures proliferation is promoted when supplemented with SIN NANOG (to overexpress NANOG) or transduced with P21-mR-NANOG-8R. Error bars indicate s.d. (d) NANOG-dependent rescue in LIF-deficient cultures generates a more epiblast-like gene expression profile. Relative gene expression analyses of LIF-deficient CGR-8 cultures using quantitative PCR (QPCR). Cultures supplemented with SIN NANOG (to overexpress NANOG) or transduced with P21-mR-NANOG-8R have increased Fgf5 expression, reduced Rex1 expression and retain Oct4 expression. Error bars indicate s.e.

Figure 7:
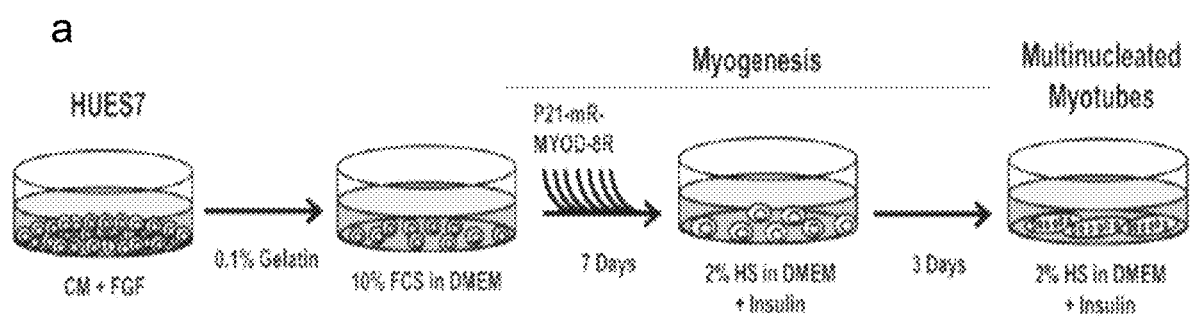
Figure 7:
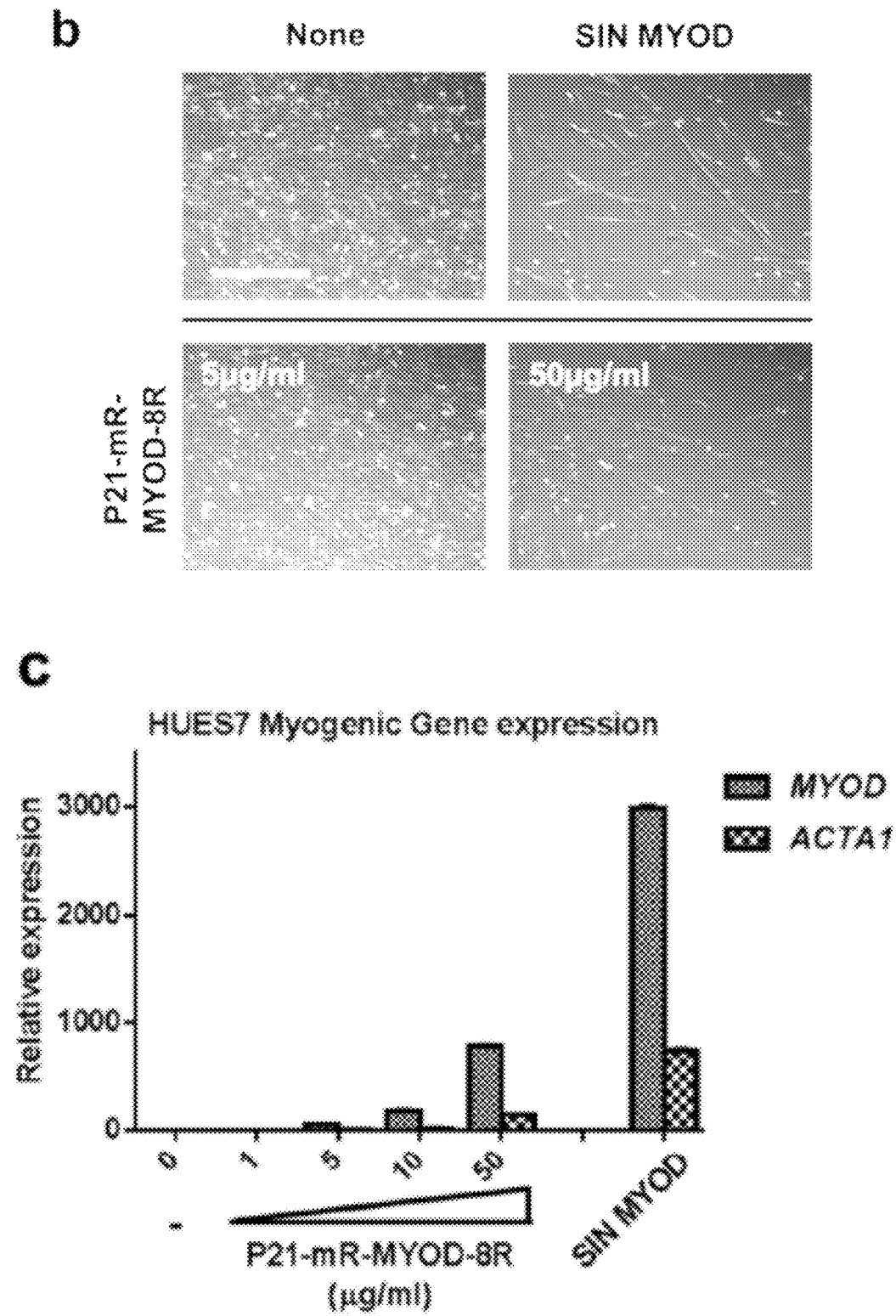
Figure 7:
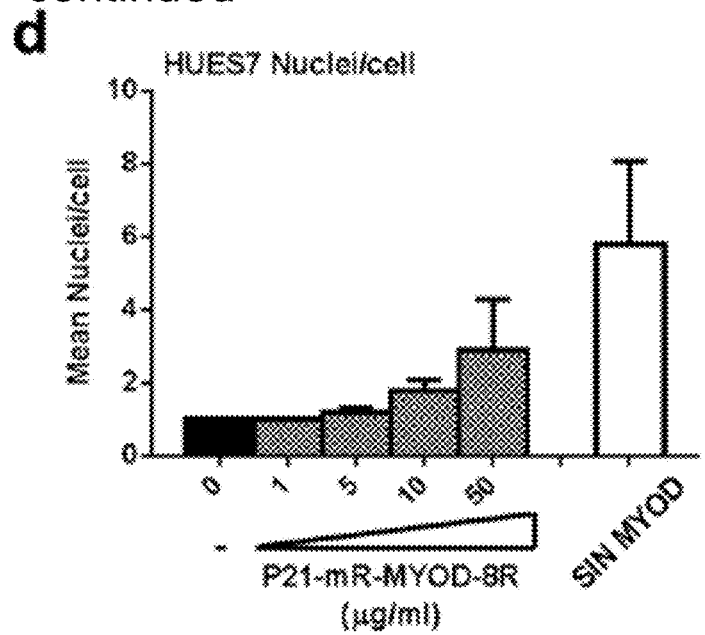
Figure 7:
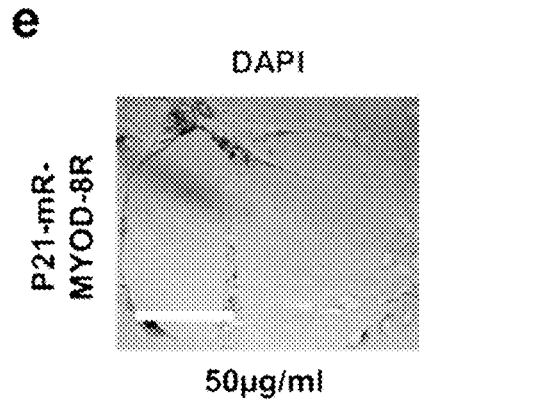
Figure 7:
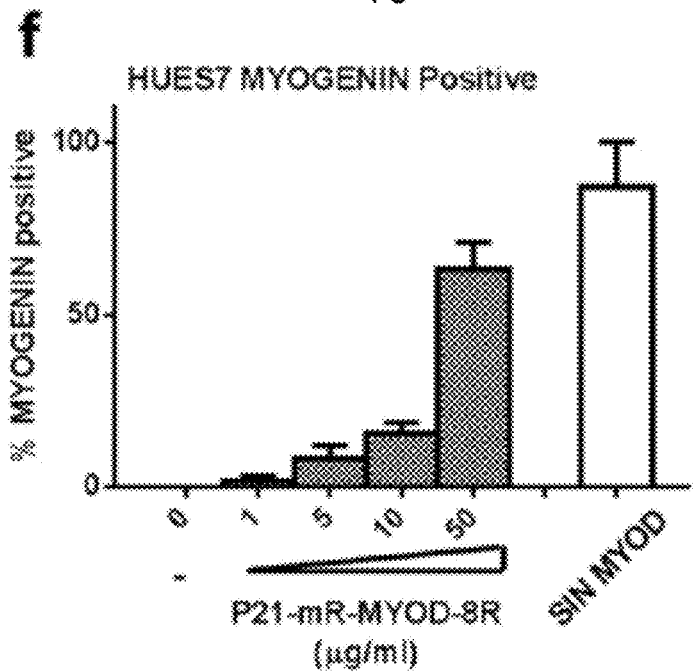

FIG. 7 GET/HETD-mediated delivery of MYOD promotes Myogenic differentiation of Human Embryonic Stem cells. (a) Scheme of testing the differentiation activity of transduced MYOD in HUES7 cells. HUES7 cells were plated onto gelatinised plastic and cultured in DMEM containing 10% (v/v) FCS. Cells were fed daily with DMEM containing 10% (v/v) FCS and P21-mR-MYOD-8R (0, 1, 5, 10 or 50 μg/ml) for 7 days. Media was then changed to DMEM containing 2% (v/v) Horse serum (HS), Human recombinant Insulin and P21-mR-MYOD-8R and fed daily for 3 days. (b-f) P21-mR-MYOD-8R drives myogenic differentiation of HUES7 cells to multinucleated Myotubes. (b) Light microscopy of HUES7 cells cultured under the myogenic regime supplemented with SIN MYOD (to overexpress MYOD) or transduced with P21-mR-MYOD-8R. Elongated fused Myotubes and single myocytes are generated with SIN-MYOD or high doses of P21-mR-MYOD-8R. Scale bar, 100 μm. (c) MYOD-dependent myogenic differentiation of human embryonic stem cells. Relative gene expression analyses of HUES7 cultures using quantitative PCR (QPCR). Cultures supplemented with SIN MYOD (to overexpress MYOD) or transduced with P21-mR-MYOD-8R have increased endogenous MYOD expression and skeletal muscle-specific ACTA1 expression. Error bars indicate s.e. (d-e) P21-mR-MYOD-8R differentiated cells are multinucleated. (d) Quantitation of mean nuclei number per cell using PI staining. Error bars indicate s.d. (e) Fluorescence microscopy images of HUES7 cells differentiated with P21-mR-MYOD-8R (50 μg/ml) and stained with nuclear dye DAPI. Scale bar, 50 μm. (f) P21-mR-MYOD-8R differentiated cells are MYOGENIN positive. Quantitation of the percentage MYOGENIN positive cells, using immunofluorescent-labelling. Error bars indicate s.d.

Figure 8:
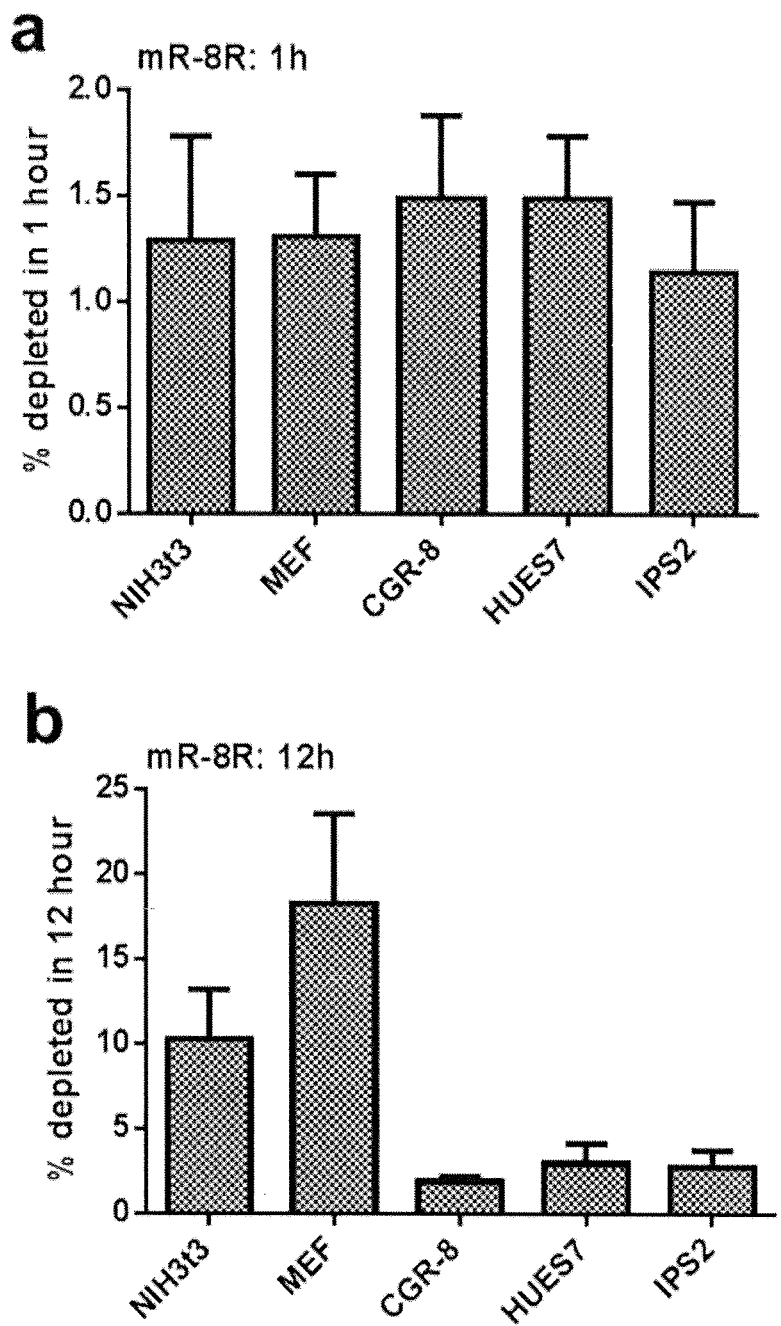

FIG. 8 PTD-proteins bind to Pluripotent cells but transduce poorly. Fluorometry of media to determine the remaining fluorescent protein remaining after incubation with cells. mR-8R was diluted to 20 μg/ml in serum-free media and 1 ml/well incubated for either 1 hour (a) or 12 hours (b) with confluent NIH3t3, MEF, CGR-8, HUES7 or IPS2 cells in 6 well plates. Fluorescence pre-incubation was assigned as 100% of units and background of serum-free media subtracted. Error bars indicate s.d.

Figure 9:
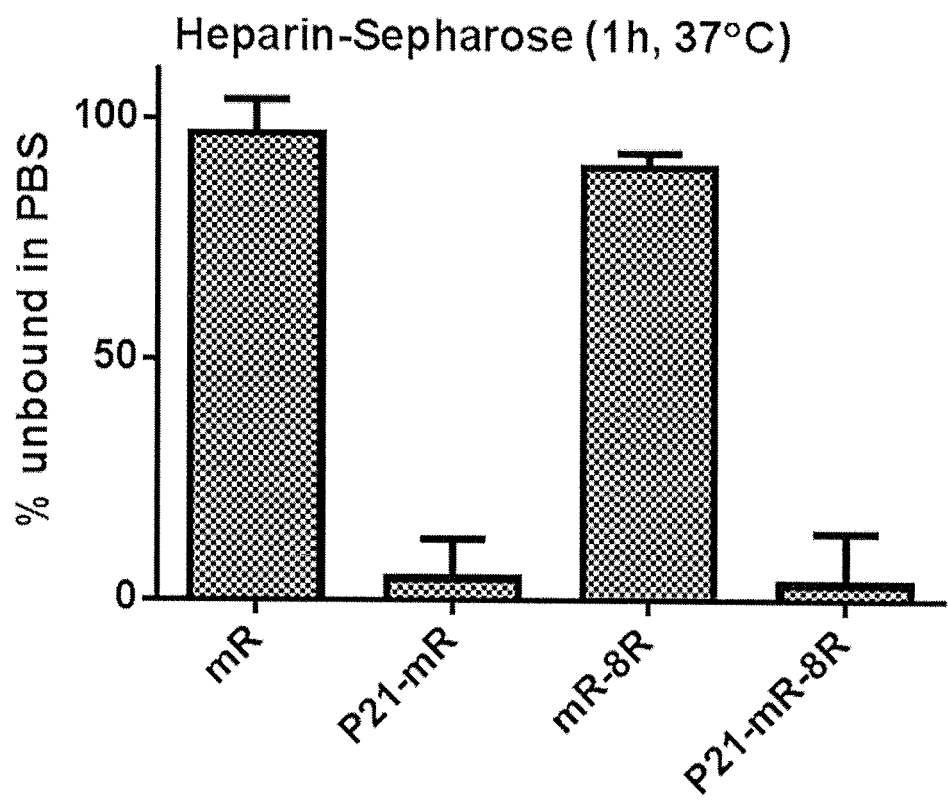

FIG. 9 P21 binds directly to Heparin. Fluorometry to determine the fluorescent protein remaining after incubation with Heparin-sepharose beads. Recombinant proteins were diluted (20 µg/ml) in serum-free media and 1 ml/tube incubated for 1 hour at 37° C. with 50 µl Heparin-sepharose with rotation. Fluorescence pre-incubation was assigned as 100% of units and background of serum-free media subtracted. Error bars indicate s.d.

Figure 10:
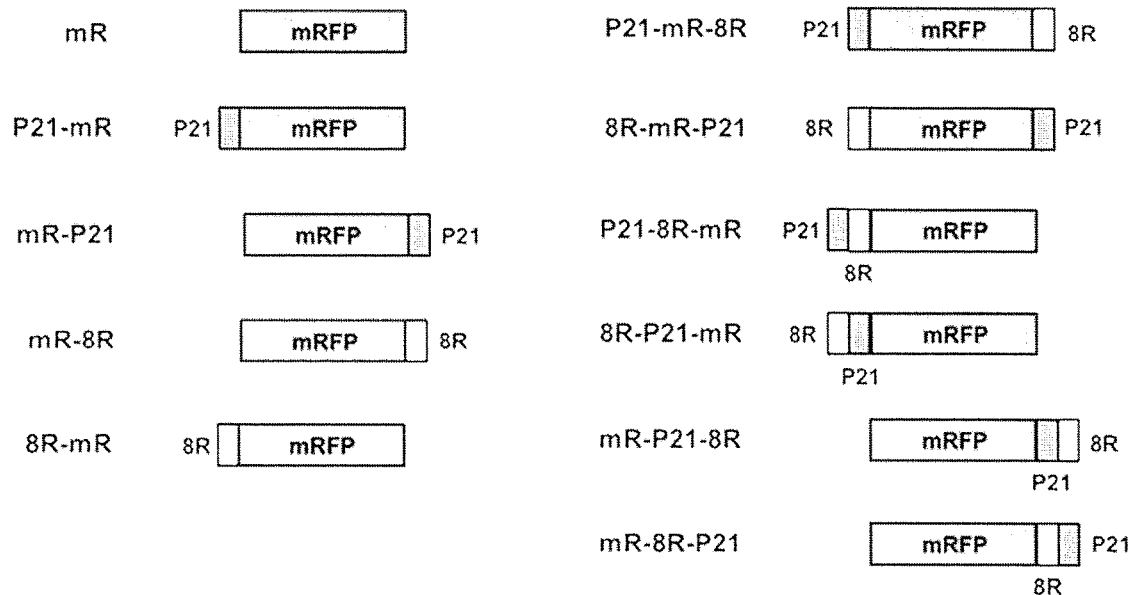
Figure 10:
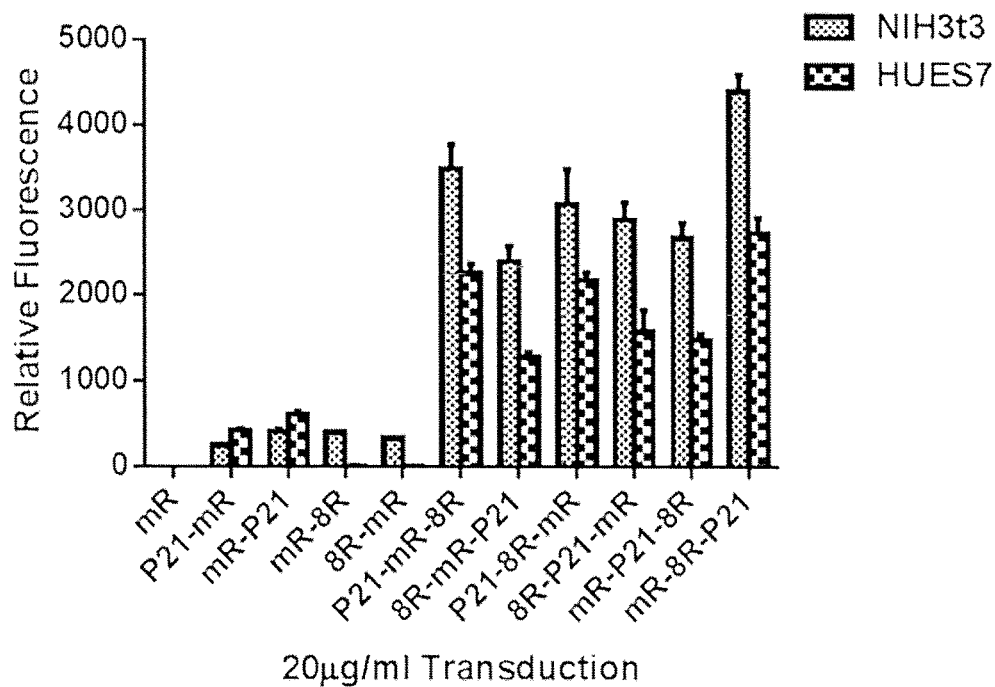

FIG. 10 GET/HETD-mediated delivery of domain position protein variants. (a) Schematic of the proteins created to test the effect of domain position on protein delivery to cells. (b) Fusion of P21 and 8R to mR in any orientation significantly improves transduction. Flow cytometry analyses of NIH3t3 and HUES7 cells incubated with the protein variants (20 g/ml) for twelve hours. Error bars indicate s.d.

Figure 11:
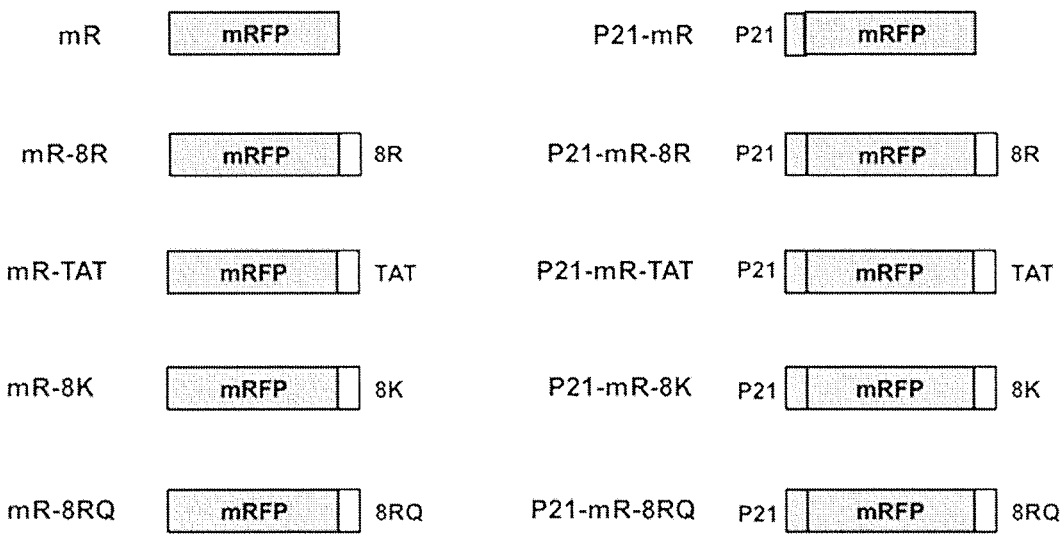
Figure 11:
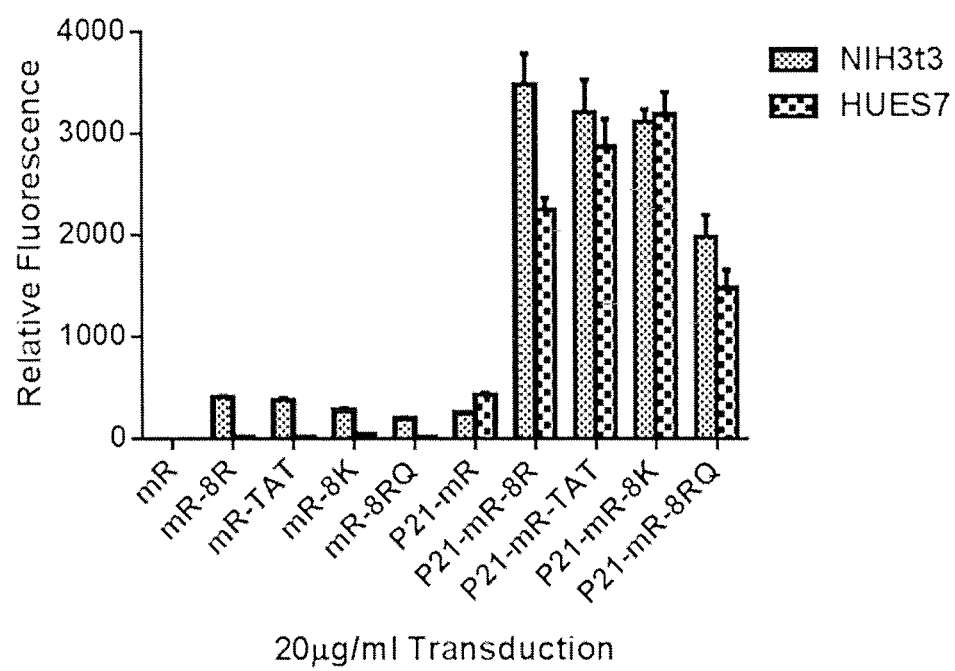

FIG. 11 GET/HETD-mediated delivery of PTD protein variants. (a) Schematic of the proteins created to test the enhancing effect of P21 on other PTDs for protein delivery to cells. 8R is RRRRRRRR (SEQ ID NO: 19), TAT is HIV-1 TAT protein RKKRRQRRR (SEQ ID NO: 20), 8K is KKKKKKKK (SEQ ID NO: 56), 8RQ is RQRQRQRQ (SEQ ID NO: 57) (b) Fusion of P21 and any PTD to mR significantly improves transduction. Flow cytometry analyses of NIH3t3 and HUES7 cells incubated with the protein variants (20 µg/ml) for twelve hours. Error bars indicate s.d.

Figure 12:
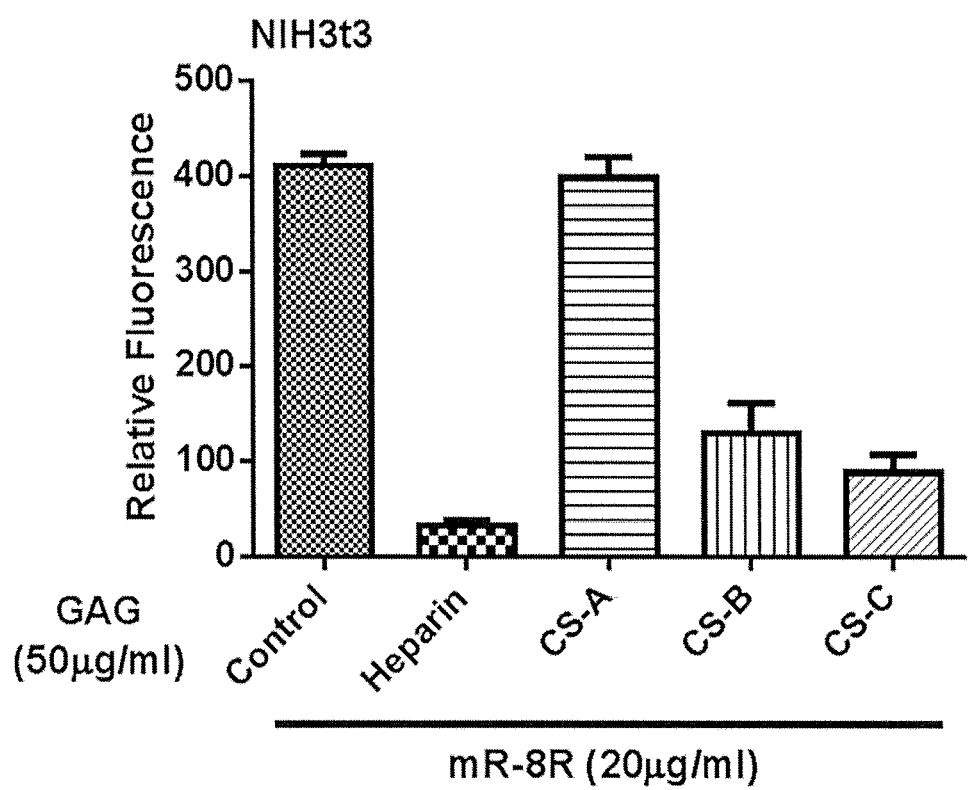

FIG. 12 PTD-mediated delivery is inhibited by free Heparin and Chondroitin sulfate. Flow cytometry analyses NIH3t3 cells treated with mR-8R (20 µg/ml) for 6 hours with or without a variety of GAGs (50 µg/ml) in serum-free medium. CS is Chondroitin sulphate. Cells were pre-incubated for 1 hour in serum-free media and transduced for 6 hours in serum-free media with or without GAGs. Error bars indicate s.d.

Figure 13:
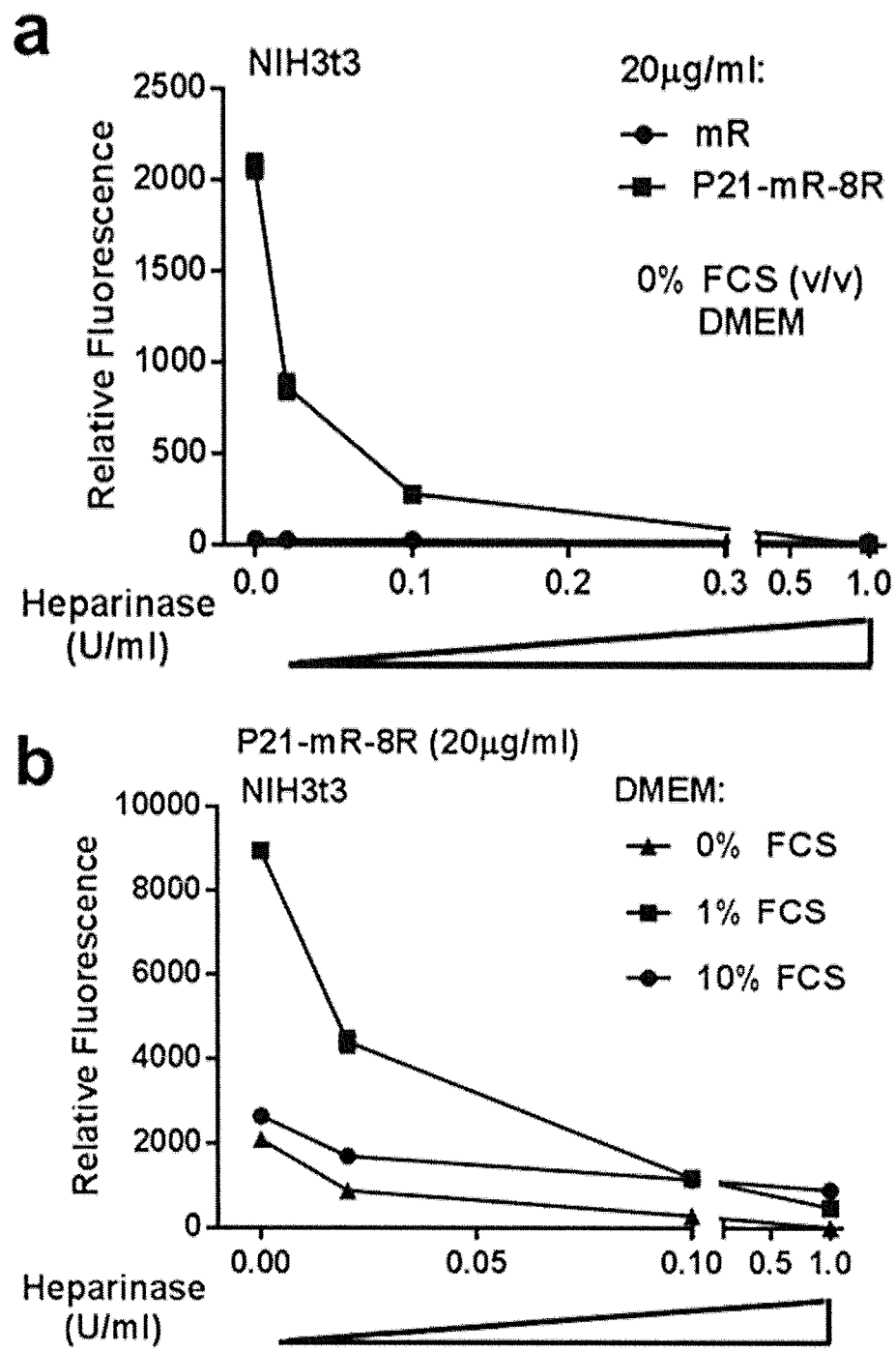
Figure 13:
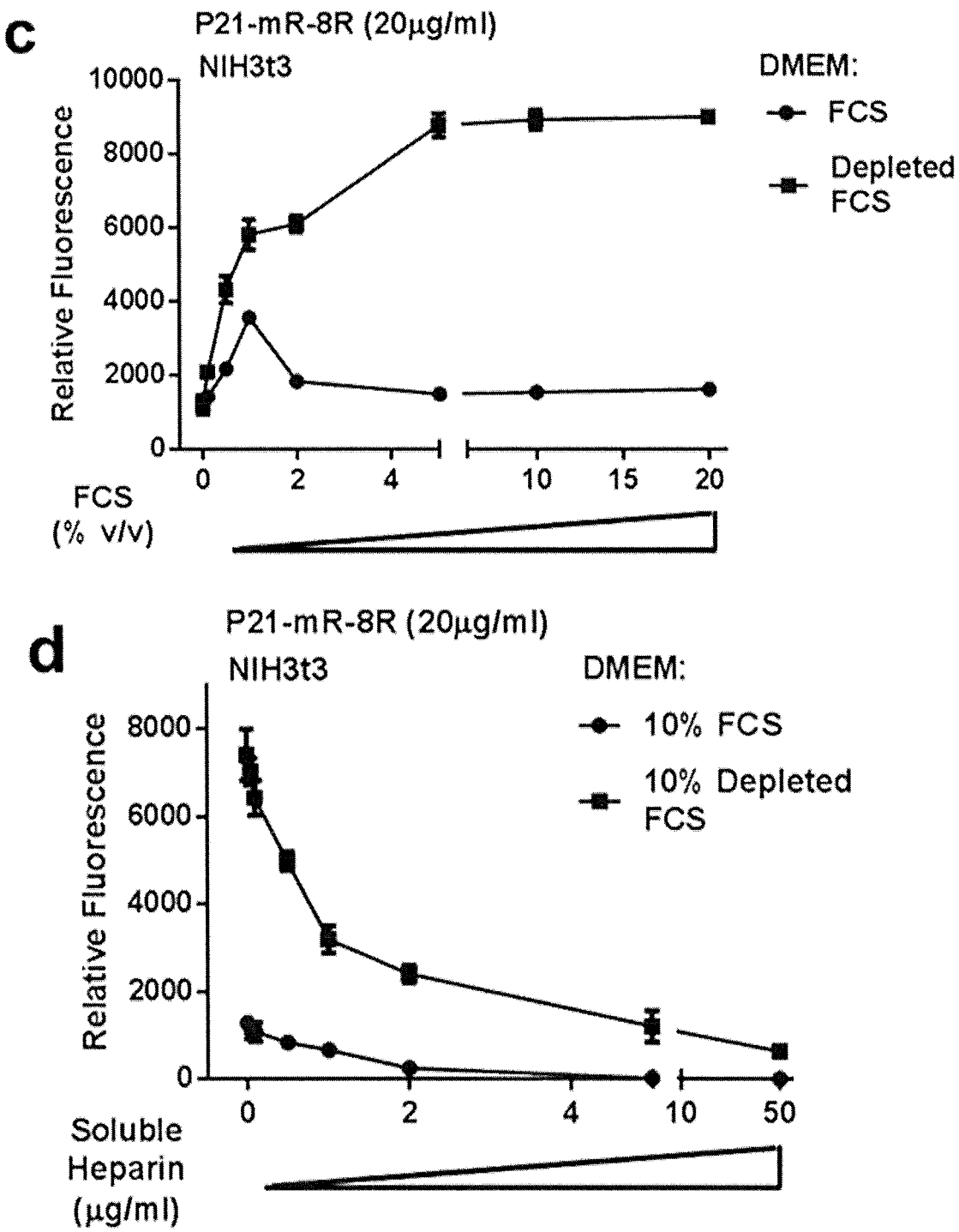

FIG. 13 GET/HETD-Protein delivery is inhibited by GAG-containing FCS, Heparinase treatment and competing soluble Heparin. (a-b) Flow cytometry of transduced cells pre-treated with Heparinase. (a) NIH3t3 cells were pre-incubated in serum-free media for 1 hour with different amounts of Heparinase III (0, 0.01, 0.1 or 1 U/ml) and transduced with mR or P21-mR-8R (20 µg/ml in serum-free media) containing Heparinase III for 12 hours. (b) NIH3t3 cells were pre-incubated in serum-free media for 1 hour with different amounts of Heparinase III and transduced with P21-mR-8R (20 µg/ml) containing Heparinase III and different amounts of FCS (0, 1 or 10% (v/v)) for 12 hours. (c) Flow cytometry of NIH3t3 cells transduced in different concentrations of FCS or FCS which has been depleted for P21-binding material. NIH3t3 cells were pre-incubated in serum-free media for 1 hour and transduced with P21-mR-8R (20 µg/ml) containing different amounts of FCS (0, 0.1, 0.5, 1, 2, 5, 10 or 20 (v/v)) for 6 hours. (d) Flow cytometry of NIH3t3 cells transduced in 10% FCS or 10% P21 binder-depleted FCS with the addition of soluble Heparin. NIH3t3 cells were pre-incubated in serum-free media for 1 hour and transduced with P21-mR-8R (20 g/ml) containing either type of FCS and different amounts of soluble Heparin (0, 0.1, 0.5, 1, 2, 5 or 50 µg/ml) for 6 hours. Error bars indicate s.d.

Figure 14:
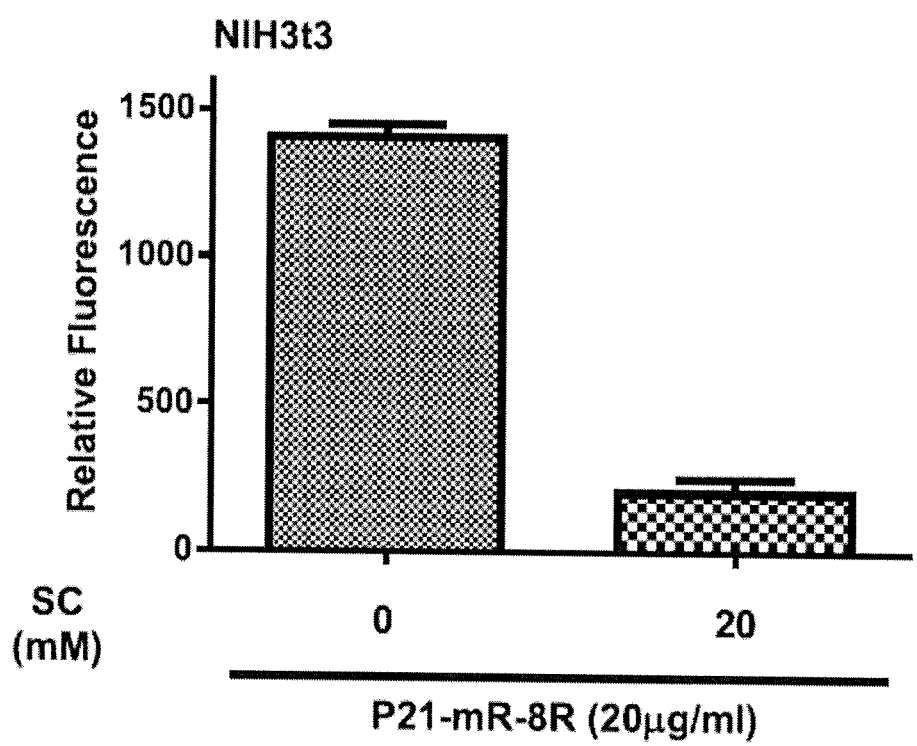

FIG. 14 GET/HETD-mediated delivery is inhibited by HS-GAG synthesis inhibitor Sodium Chlorate. Flow cytometry analyses NIH3t3 cells treated with P21-mR-8R (20 µg/ml) for 6 hours with or without Sodium Chlorate (SC, 20 mM) in serum-free medium. Cells were pre-incubated with or without SC for 1 hour in serum-free media and transduced for 6 hours in serum-free media with or without SC. Error bars indicate s.d.

Figure 15:
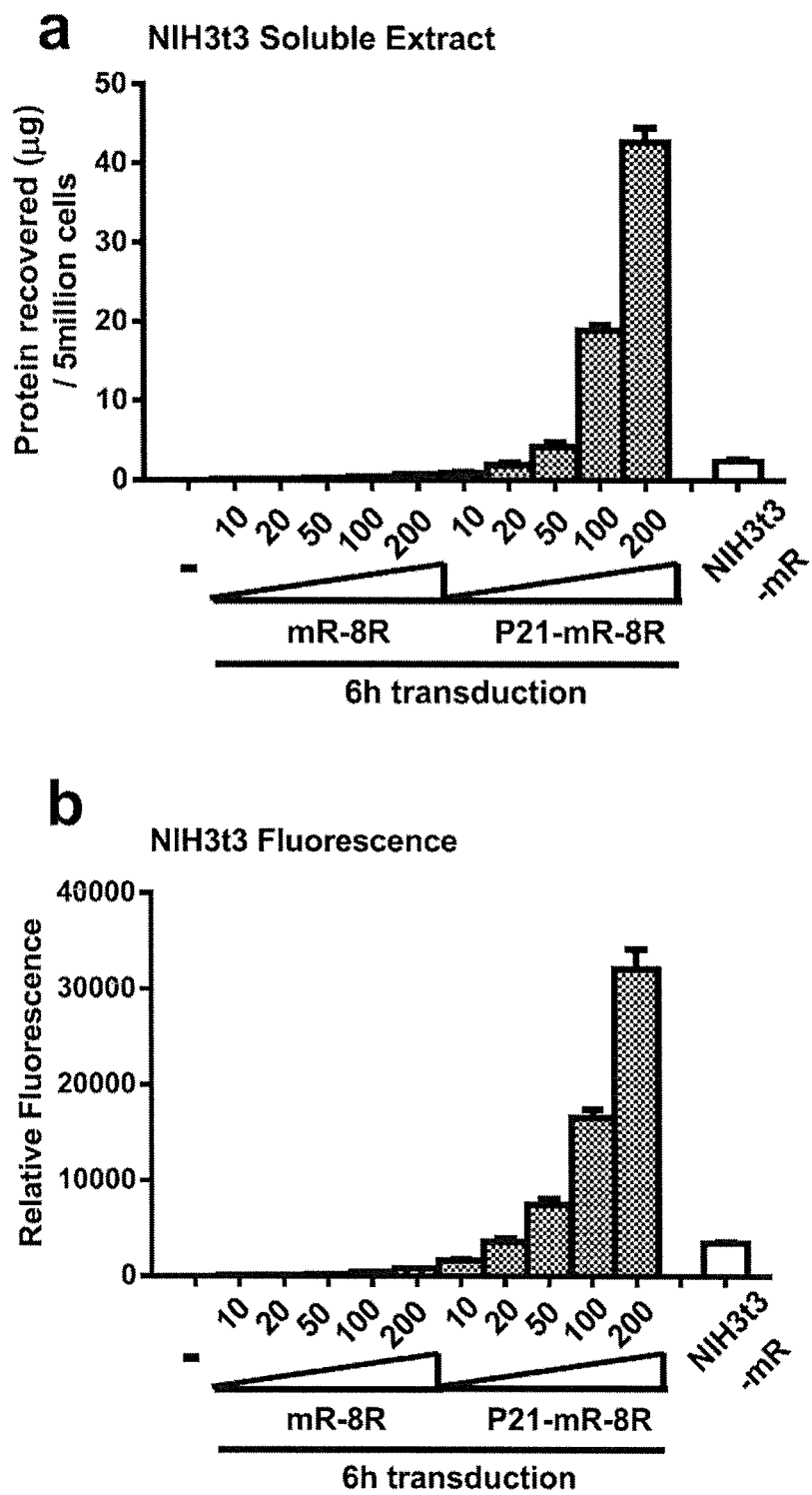

FIG. 15 GET/HETDs can achieve higher intracellular levels of cargo delivery than transgenic systems. (a) Fluorometry of soluble extracts generated from NIH3t3 mR (transgenic NIH3t3 cells transduced with SIN mR) compared with those from NIH3t3 cells transduced for 6 hours with different doses of mR-8R or P21-mR-8R (0, 10, 20, 50, 100 or 200 µg/ml in serum-free media) (b) Flow cytometry of NIH3t3 mR (transgenic NIH3t3 cells transduced with SIN mR) compared with those from NIH3t3 cells transduced for 6 hours with different doses of mR-8R or P21-mR-8R (0, 10, 20, 50, 100 or 200 µg/ml in serum-free media). Fluorescence is normalised to untreated NIH3t3 cells. Error bars indicate s.d.

Figure 16:
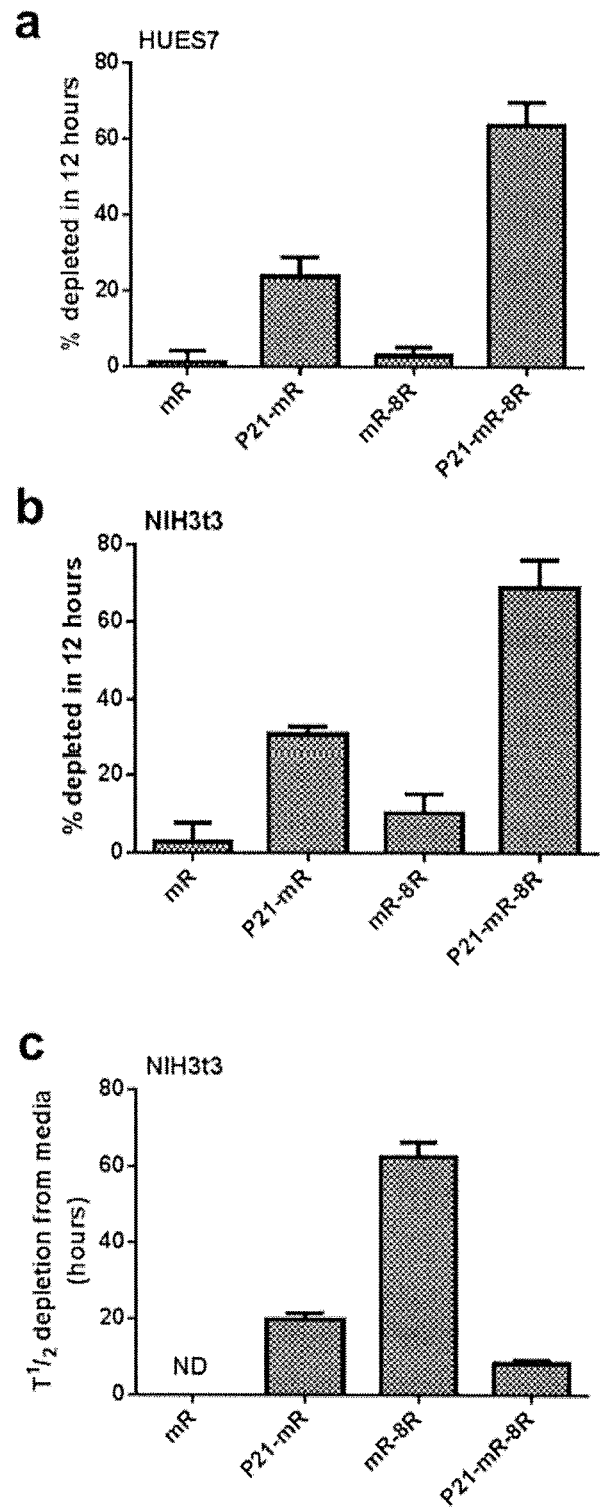

FIG. 16 GET/HETD-tagged proteins are rapidly depleted from culture media by efficient transduction. (a-b) Fluorometry of media to determine the remaining fluorescent protein remaining after incubation with cells. Recombinant proteins were diluted to 20 µg/ml in serum-free media and 1 ml/well incubated for 12 hours with confluent NIH3t3s in 6 well plates. Fluorescence pre-incubation was assigned as 100% of units and background of serum-free media subtracted. (a) HUES7-mediated depletion of recombinant proteins from culture media in 12 hours. (b) NIH3t3-mediated depletion of recombinant proteins from culture media in 12 hours. (c) The Tl/2 depletion was calculated by incubating NIH3t3 cells with recombinant proteins (20 µg/ml) for different times. Bar chart shows the time (hours) required to deplete the recombinant protein to half the starting concentration in the described system. Error bars indicate s.d.

Figure 17:
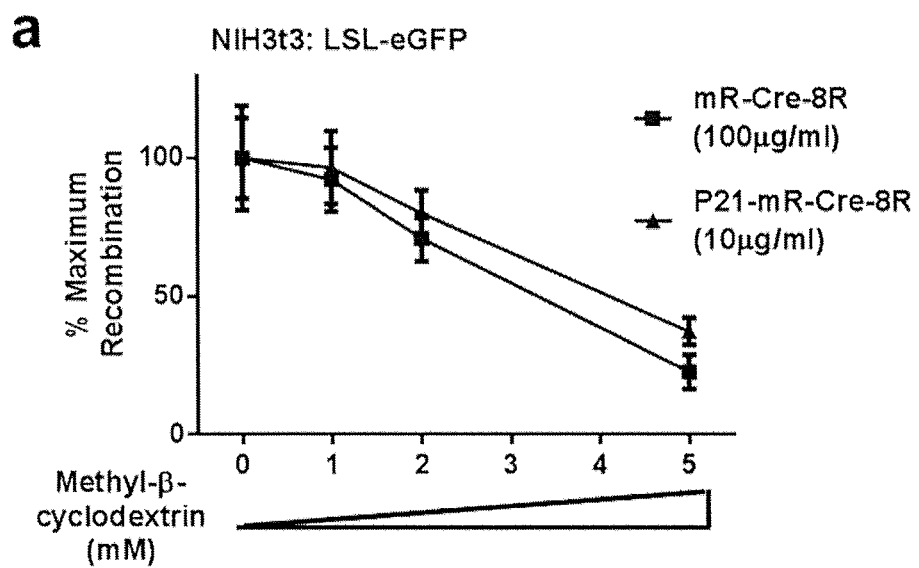
Figure 17:
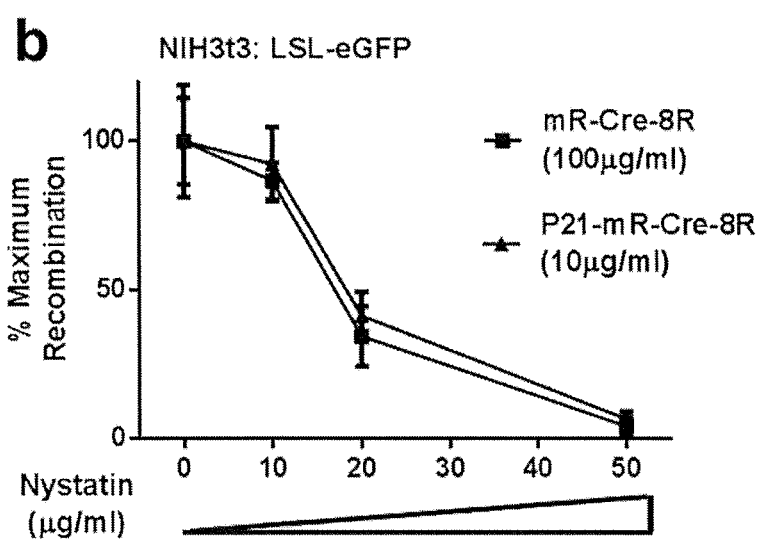
Figure 17:
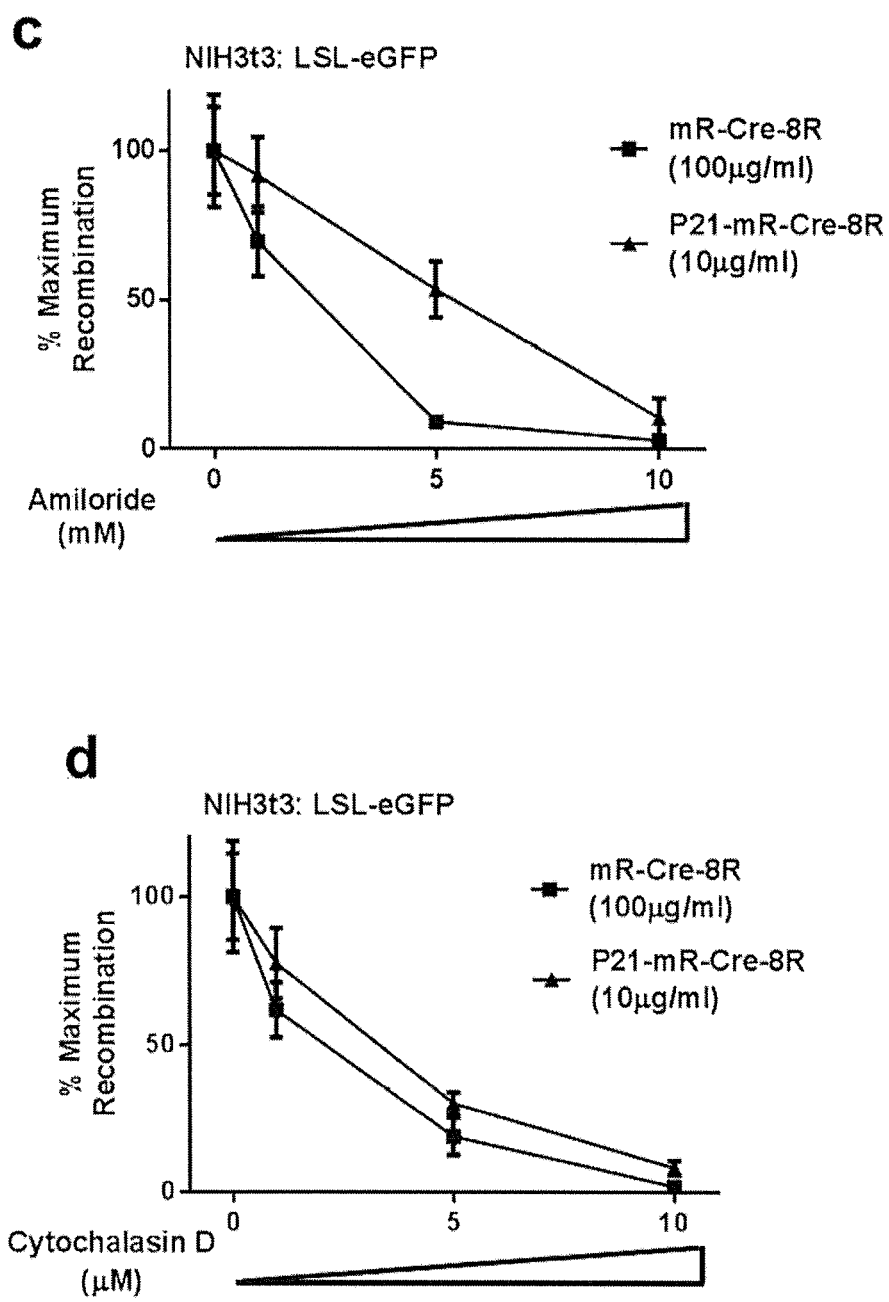
Figure 17:
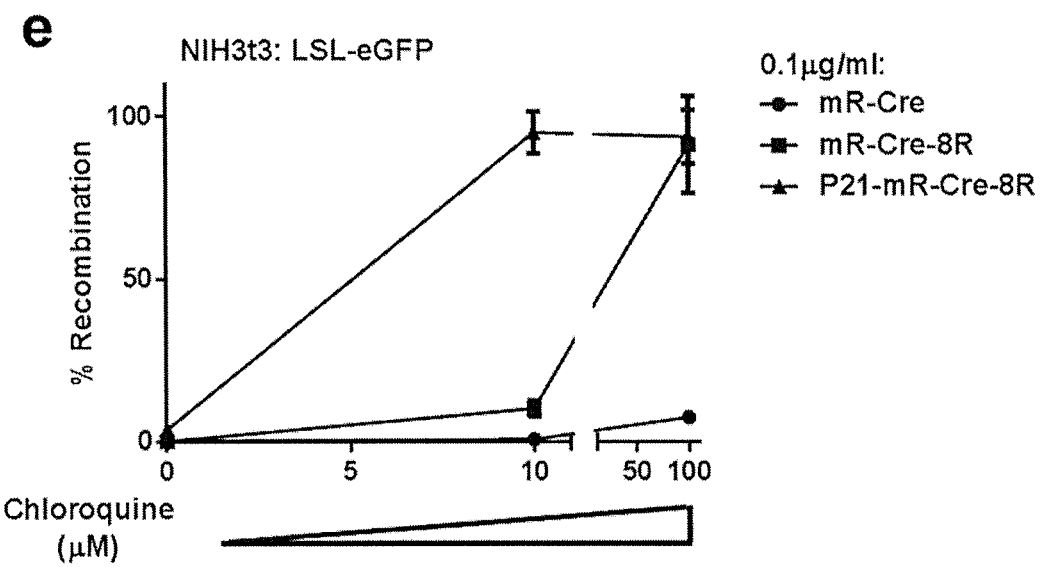
Figure 17:
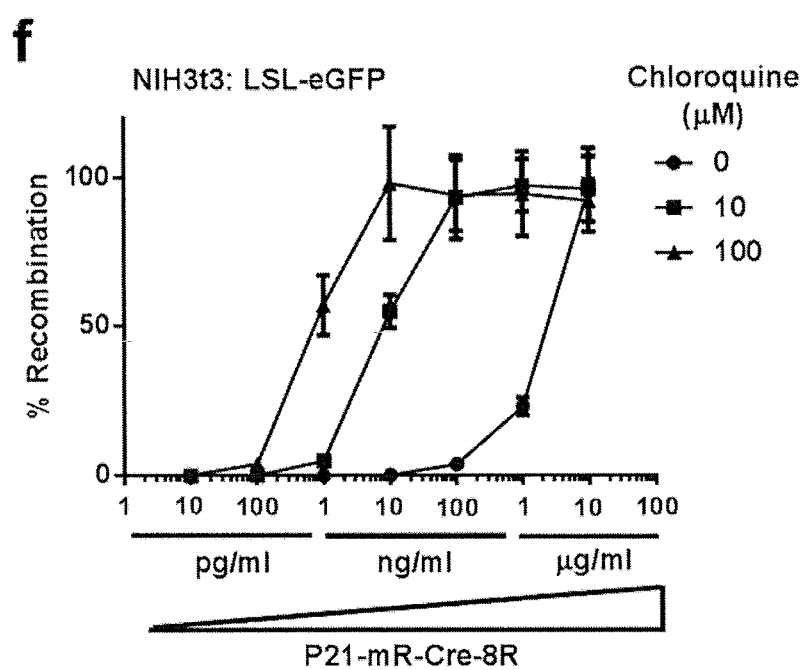

FIG. 17 HERD-mediated Cre Recombinase nuclear activity is promoted by vesicle escape but repressed by inhibitors of macropinocytosis or cholesterol depletion. NIH3t3; LSL-eGFP cells were pre-incubated in serum-free media (with or without drugs), transduced with Cre proteins (mR-Cre: 100 g/ml or P21-mR-8R: 10 µg/ml) for 1 hour in serum-free media (with or without drugs), washed and cultured for 12 hours in full growth media (with or without drugs) and a further 36 hours in full growth media before analyses. (a) Methyl-β-cyclodextrin (used to deplete cholesterol) inhibits Cre transduction and recombination. (Methyl-β-cyclodextrin doses were 0, 1 2 and 5 mM). (b) Nystatin (a drug which sequesters cholesterol) inhibits Cre transduction and recombination. (Nystatin doses were 0, 10, 20 and 50 µg/ml). (c) Amiloride (a specific inhibitor of $Na^+/H^+$ exchanged required for macropinocytosis) inhibits Cre transduction and recombination. (Amiloride doses were 0, 1, 5 or 10 mM). (d) Cytochalasin D (an F-actin elongation inhibitor) inhibits Cre transduction and recombination. (Cytochalasin D doses were 0, 1, 5 or 10 µM). (e) Chloroquine promotes the release of Cre from endosomal vesicles and increases recombination (Chloroquine doses were 0, 10 and 100 µM). (f) Picogram per millilitre amounts is required to induce recombination with enhanced vesicle escape. The dose of transduced P21-mR-Cre-8R was varied in ten-fold dilutions (0-100 µg/ml) with 1 hour incubation in the presence of Chloroquine. All data is presented as % of the maximal recombination. Error bars indicate s.d.

Figure 18:
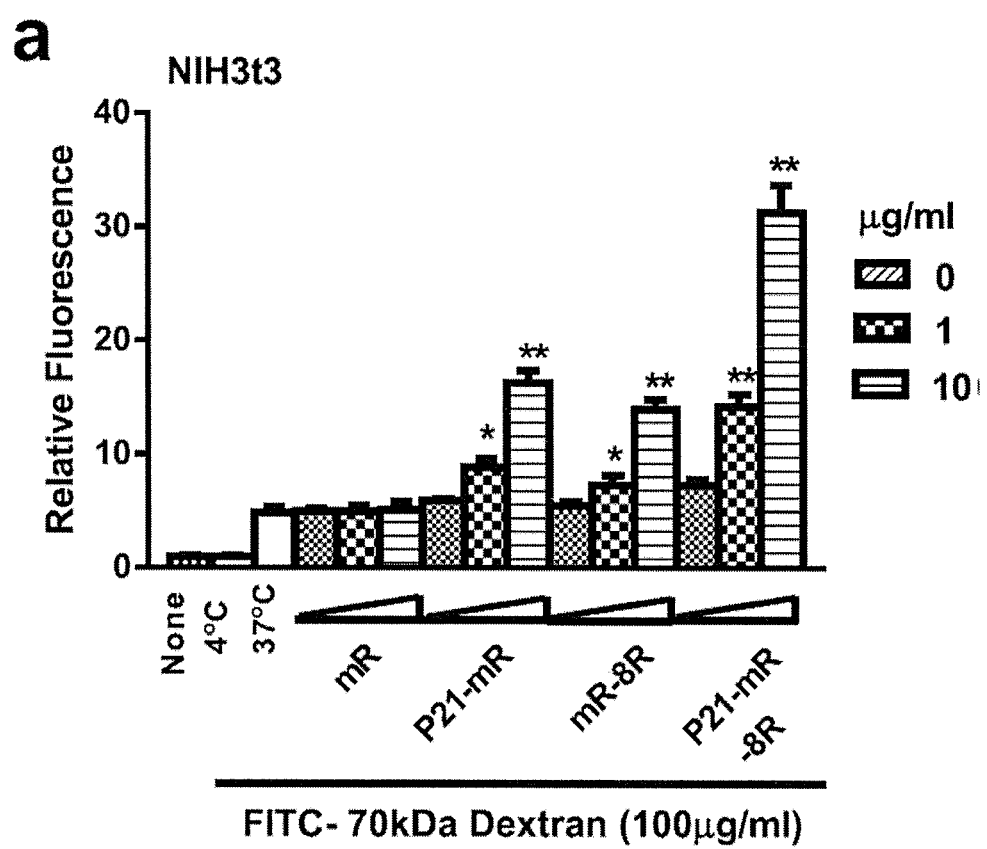

FIG. 18 GET/HETD-mediated transduction increases general cellular macropinocytosis. Flow cytometry of cells incubated in 70 kDa FITC-Dextran and transduced with recombinant proteins. NIH3t3 cells were pre-incubated in serum-free media for 1 hour and transduced with mR, P21-mR, mR-8R or P21-mR-8R (20 µg/ml in serum-free media) containing 70 kDa FITC-Dextran (neutral) for 1 hour. Error bars indicate s.d.

Figure 19:
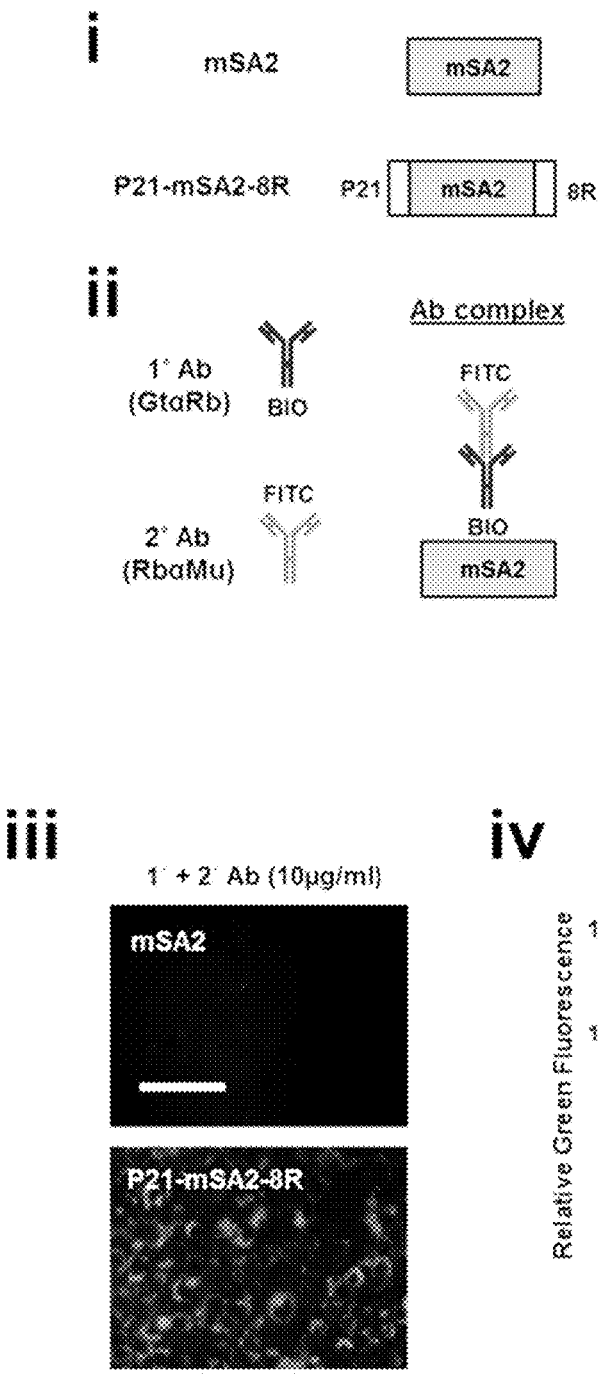
Figure 19:
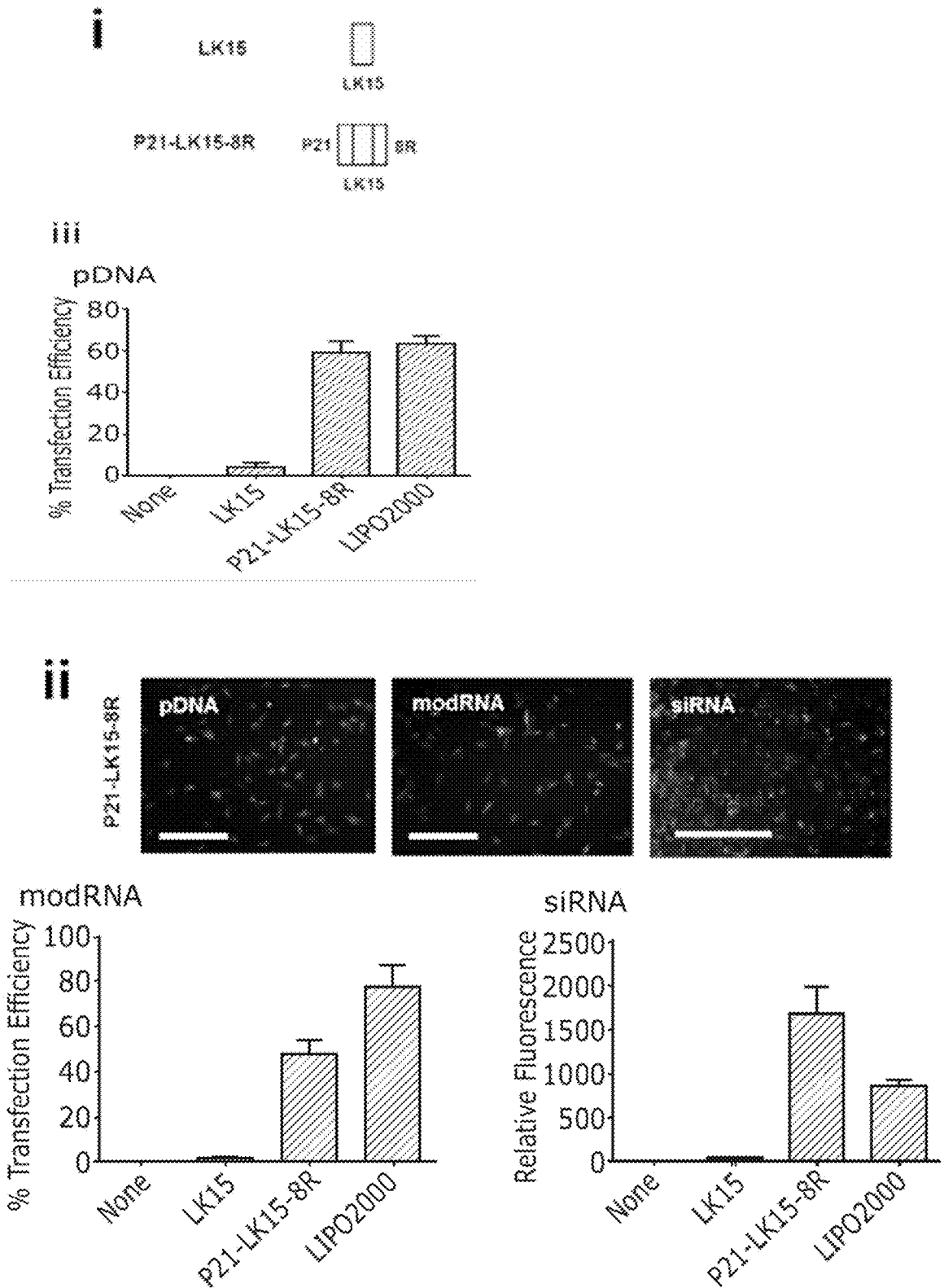
Figure 19:
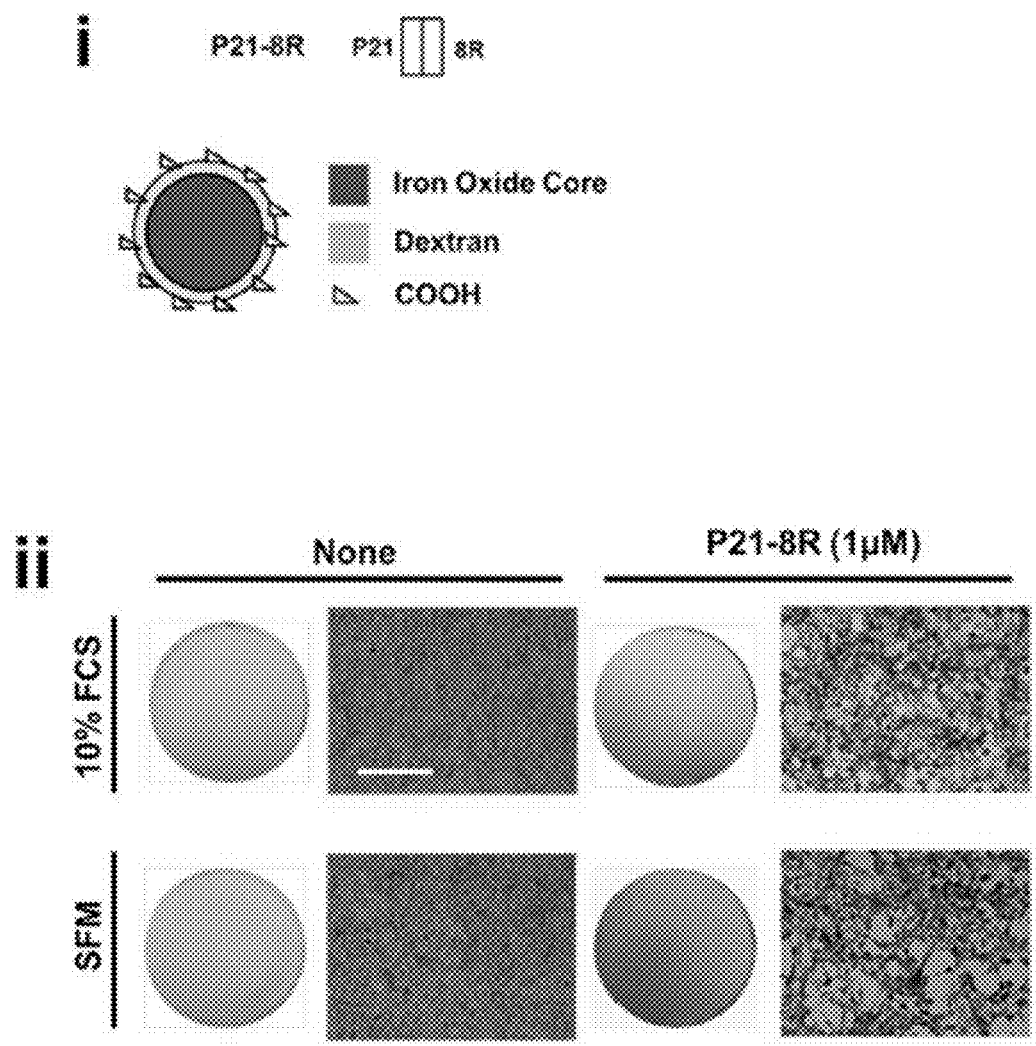

FIG. 19 GET of non-protein Cargoes. (a) GET of biotinylated cargoes using monomeric streptavidin (mSA2). (i) Schematic of the mSA2 proteins engineered to bind to and transduce biotinylated cargoes. P21-8R was used as a non-interacting control, mSA2 as a non-transducing control, and P21-mSA2-8R as the test protein. (ii) Schematic of the antibody (Ab) complexes of a biotinylated primary (1°) antibody (Goat anti-rabbit; GtαRb) bound to an FITC-conjugated secondary (2°) antibody (Rabbit anti-mouse; Rb αMu) used to test activity. (iii) GET-delivery of Ab complexes were visible by fluorescence microscopy (scale bar, 50 µm). With co-incubation of P21-mSA2-8R (10 µg/ml, bottom image), Ab complexes were efficiency delivered to cells (iv) Flow cytometry demonstrating that 1'/2 Ab complexes (1 g/ml) are taken into NIH3t3 cells poorly by direct incubation or when co-incubated with mSA2 only. (b) GET of nucleic acids by employing LK15 peptide. (i) Schematic of the LK15 proteins engineered to bind to and transduce nucleic acids. (ii) Transfection of human mesenchymal stem cells (iHMSCs) using GET-LK15. Initially we assessed binding capacity of LK15 peptides for plasmid (p)DNA (SIN GFP, to express GFP on transfection), modified synthetic messenger RNA (modRNA) (Miltenvi Biotech; to express GFP on transfection) and small-inhibitory (si)RNAs (labelled with FAM fluorophore to detect delivery). After optimising ratios we transfected iHMSCs with P21-LK15-8R and pDNA (10 µg), modRNA (10 µg) or siRNA (1 µg) and visualised transfection by fluorescence microscopy (scale bar, 100 µm). (iii) Quantification of GET-LK15 transfection of iHMSCs by flow cytometry (% transfection efficiency or relative fluorescence for siRNA) compared to lipofectamine (LIPO)2000 as a commercial standard. Error bars indicate s.d. (c) GET of Magnetic Nanoparticles. (i) Schematic of the P21-8R peptide synthesised and test magnetic nanoparticles (MNPs). We tested 250 nm Nanomag-D dextran shell/iron oxide core MNPs and conjugated P21-8R peptide to surface COOH groups. (ii) MNPs are taken into NIH3t3 cells most efficiently in serum-free media (SFM; left panel). Light microscopy images of Prussian blue iron stained NIH3t3 cells treated with MNPs (50 µg/ml) for twelve hours in standard media conditions (10% FCS) or SFM. Conjugation of P21-8R to MNPs significantly increases cellular uptake in both 10% FCS and SFM conditions (circular image is of entire well, scale bar, 100 m).

Figure 20:
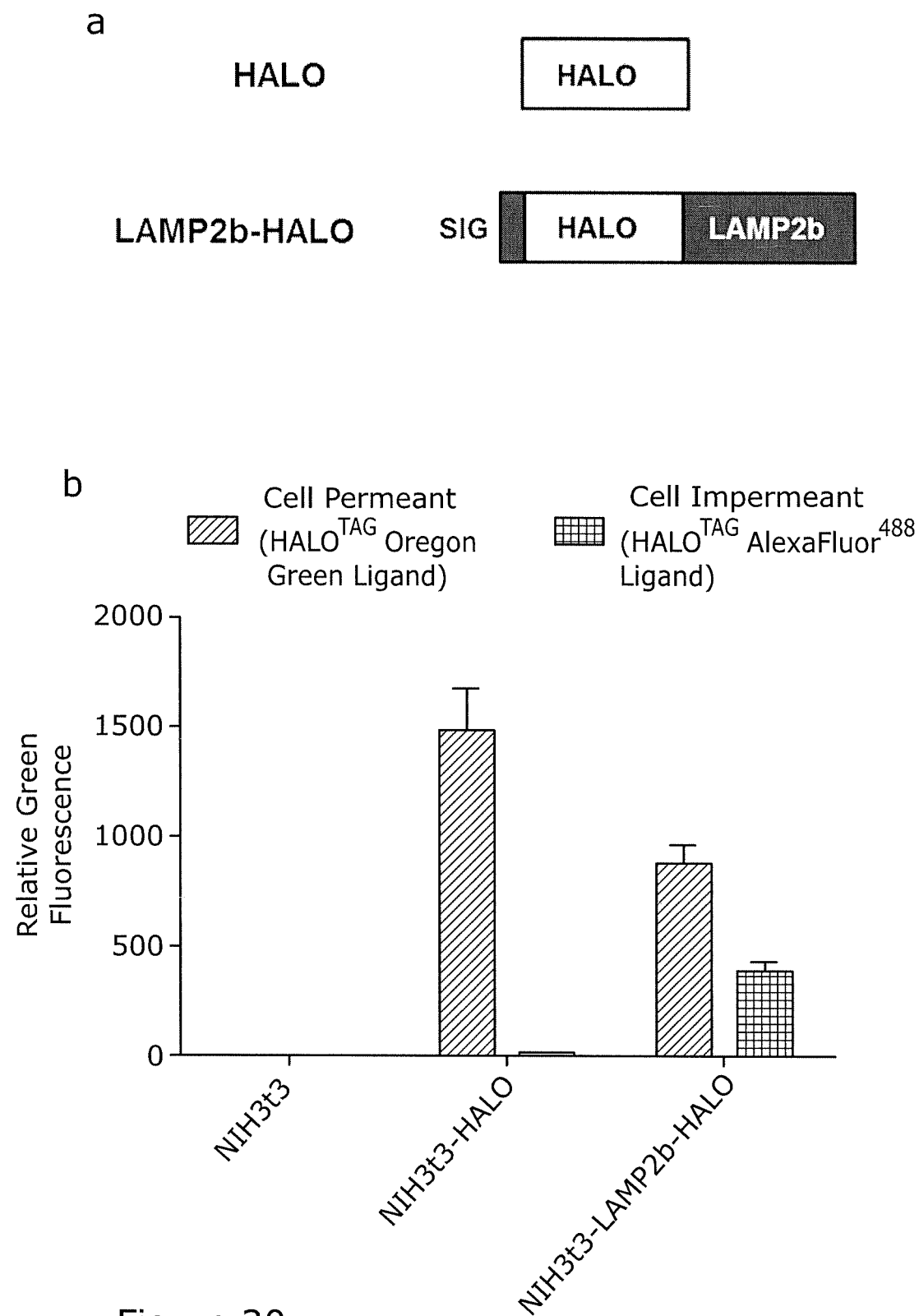

FIG. 20 Ligand auto-labelling of intracellular and extracellular membrane-anchored HALO proteins. (a) Schematic of the HALO (intracellular) and LAMP2b-HALO (extracellular membrane-anchored) transgenic SIN lentivirus constructs. In LAMP2b-HALO the expressed protein is localised to the cell membrane by the signal peptide (SIG) which is cleaved and presented on the extracellular side of the cell membrane (b) NIH3t3 cells transgenic for intracellular HALO protein (NIH3t3-HALO) are only efficiently labelled by cell permeant ligands (HALO$^{TAG}$ Oregon Green). NIH3t3 cells transgenic for membrane-anchored extracellular HALO protein (NIH3t3-LAMP2b) is efficiently labelled by both cell permeant and cell impermeant ligands (HALO$^{TAG}$ Alexafluor$^{488}$). Data shows flow cytometry of the NIH3t3 cell-lines incubated in ligand (1 µM) for 15 mins, followed by 3 media washes and a 15 mins incubation to remove unbound ligand. Error bars indicate s.d. This provides an assay to assess intra-verses extracellular localisation of HALO proteins.

Figure 21:
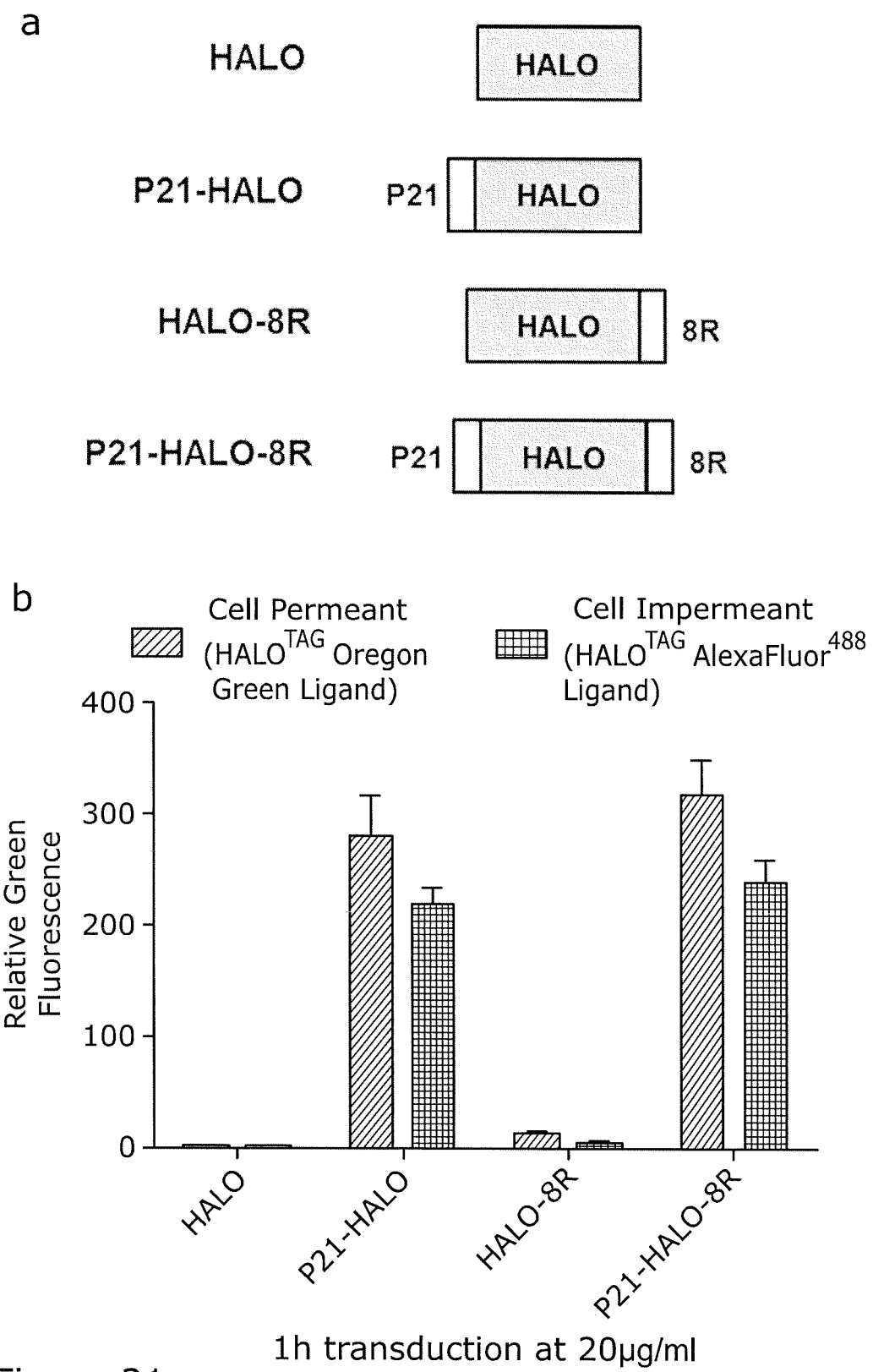
Figure 21:
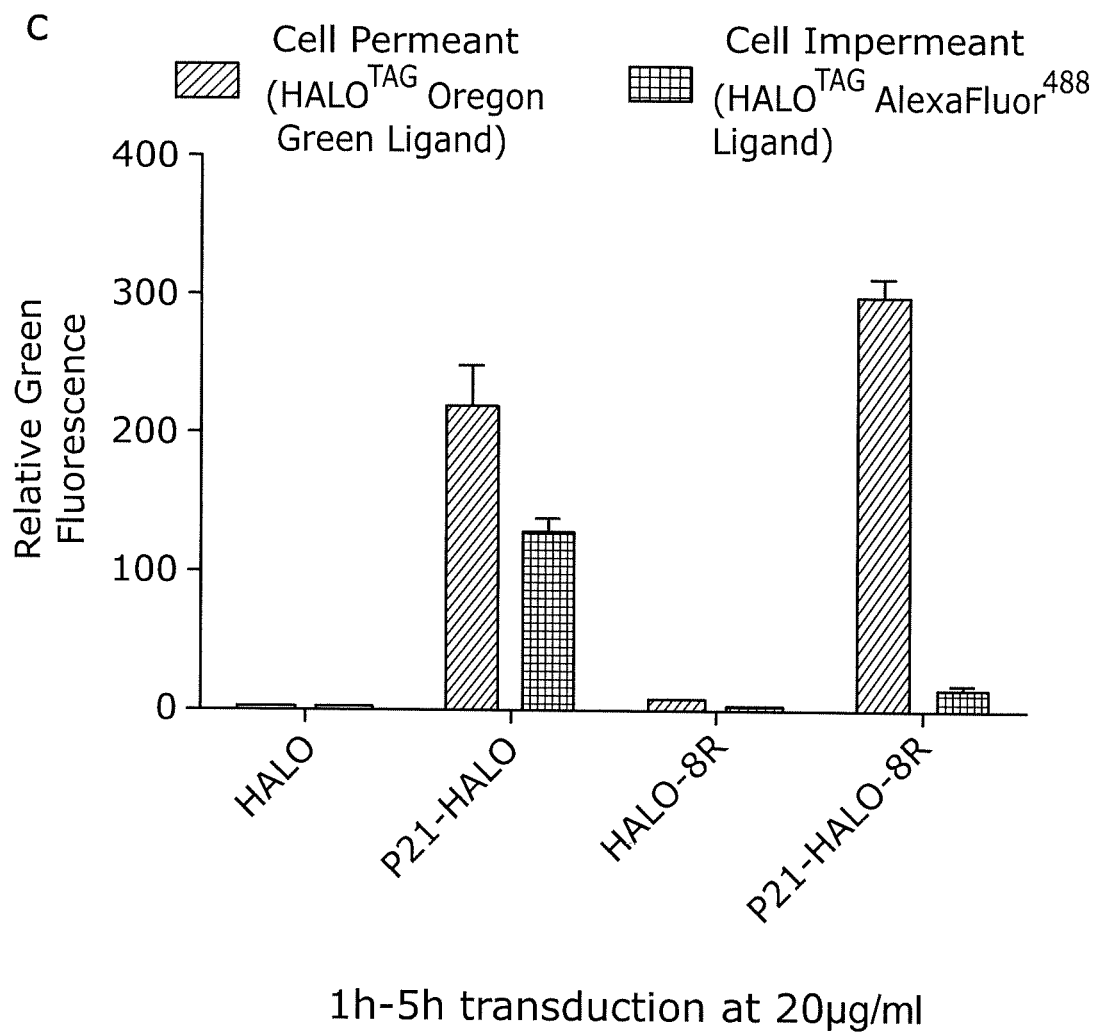

FIG. 21 Ligand labelling of GET-HALO proteins demonstrates rapid cell binding and transduction. (a) Schematic of HALO proteins created (as described for mRFP in FIG. 1). (b) P21-HALO-8R and P21-HALO efficiently bind NIH3t3 cells but do not significantly internalise with a 1 hour incubation. (c) Bound P21-HALO-8R efficiently transduces into NIH3t3 cells with further incubation (1 h-5 h). Bound P21-HALO does not as efficiently enter cells and remains bound to cell membrane with further incubation. Data shows flow cytometry analyses of NIH3t3 cells treated with proteins (20 µg/ml) for 1 hour followed direct ligand labelling (1 h) or further incubation of 5 hours (1 h-5 h). Error bars indicate s.d.

Figure 22:
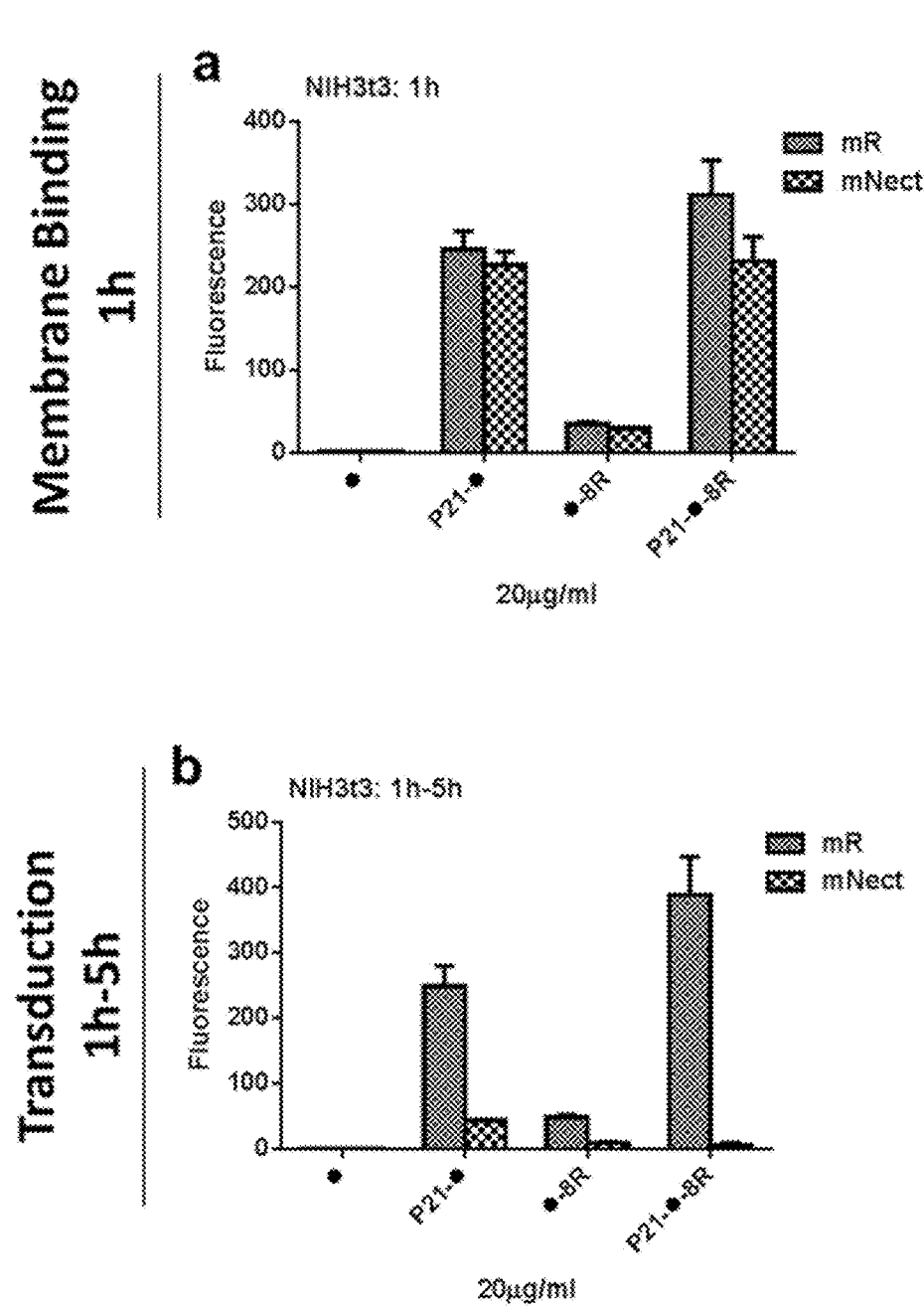
Figure 22:
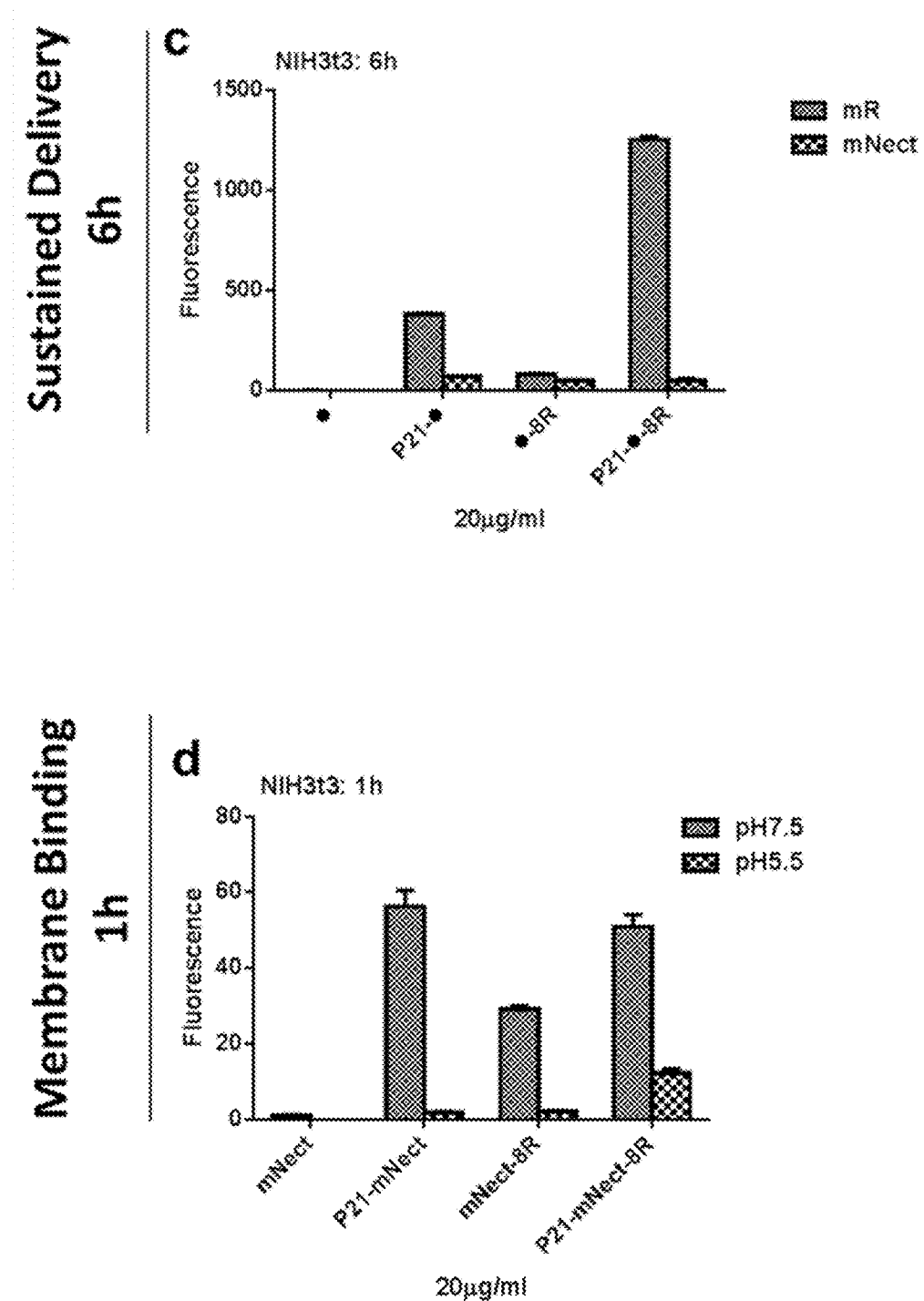
Figure 22:
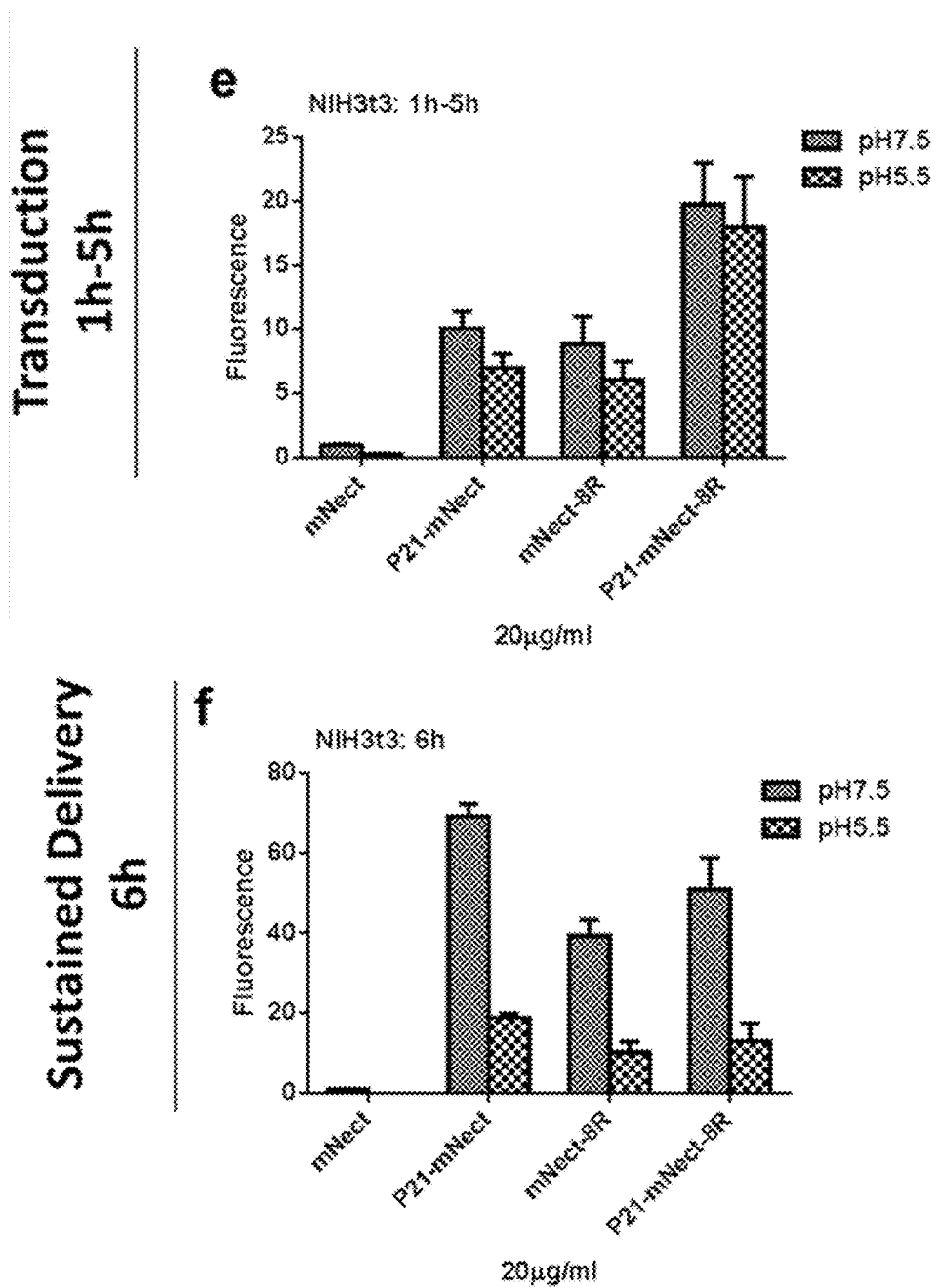

FIG. 22 pH-sensitivity of GET-mNectarine (mNect) proteins demonstrates rapid cell binding and transduction. (a) Schematic of HALO proteins created (as described for mRFP in FIG. 1). (b-c) GET-mNect or GET-mR proteins (20 µg/ml) were transduced into NIH3t3 cells for 1 h (to demonstrate membrane binding activity), 1 h followed by a further 5 h incubation without protein (1 h-5 h) (to demonstrate transduction activity) or 6 h (to demonstrate sustained delivery). Flow cytometry was used to compare intensities of mNect and mR GET-proteins. Fluorescence signal from transducing mNect proteins (unlike mR versions) is rapidly lost after internalisation new to endosomal acidification and protein unfolding. Error bars indicate s.d. (d-f) GET-mNect proteins (20 µg/ml) were transduced into NIH3t3 cells for the same regimes but washed in DMEM at pH7.5 or pH5.5 before cytometry. Membrane localised mNect protein fluorescence is extinguished by pH5.5 but is retained at pH7.5 indicating at 1 h incubations leave P21-mNect-8R external to cells, bound to membranes and not protected from pH-mediated unfolding. 1 h-5 h incubations demonstrate that P21-mNect-8R localisation is shifted and protected from pH-mediated unfolding demonstrating internalisation of the protein and protection by the cell membrane. Error bars indicate s.d.

Figure 23:
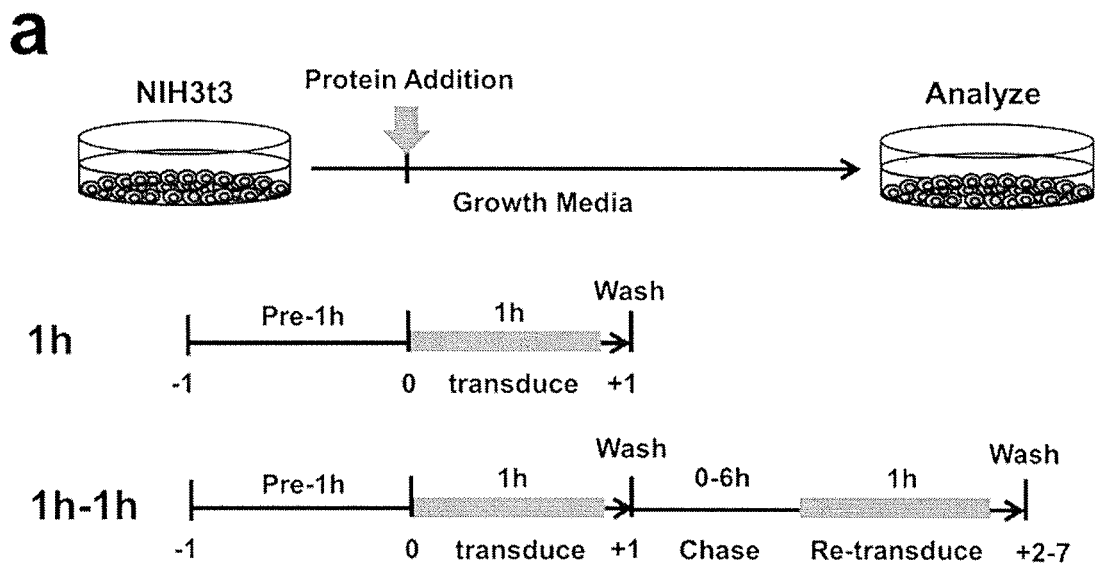
Figure 23:
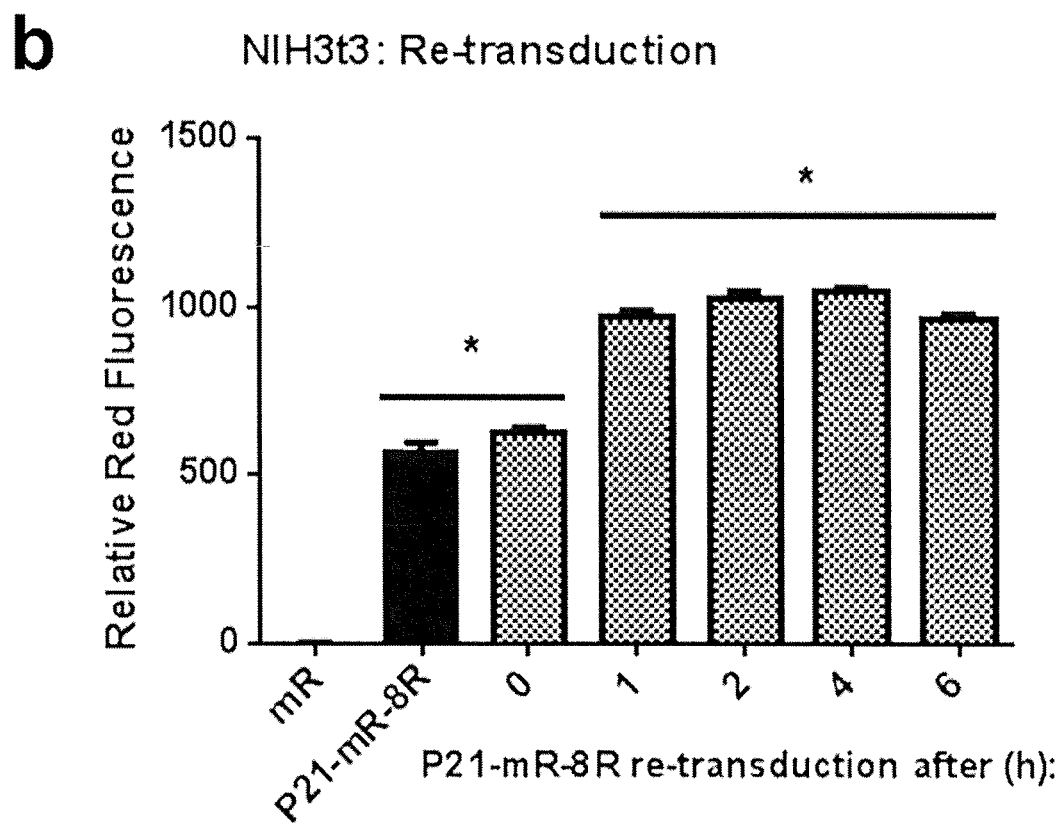

FIG. 23 GET protein must be delivered intracellularly to allow successful re-transduction (a) Scheme of testing the effect of re-transduction of GET proteins in NIH3t3 cells. Cells were pre-incubated in fresh media for 1 hour and transduced with P21-mR-8R (20 µg/ml) for 1 hour. Cells were then either analysed for fluorescence or re-transduced with P21-mR-8R (20 µg/ml) for a further 1 hour. This re-transduction was either immediate (0 h) or with a 1-6 hour incubation between re-transduction before fluorescence analyses by flow cytometry. Immediate re-transduction is inhibited whereas >1 hour incubation between transductions allows the most efficient re-transduction of GET-protein (b). Error bars indicate s.d. * p<0.05.

Figure 24:
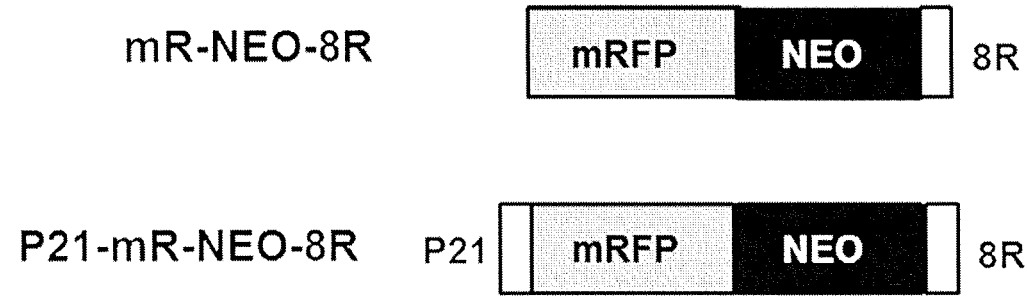
Figure 24:
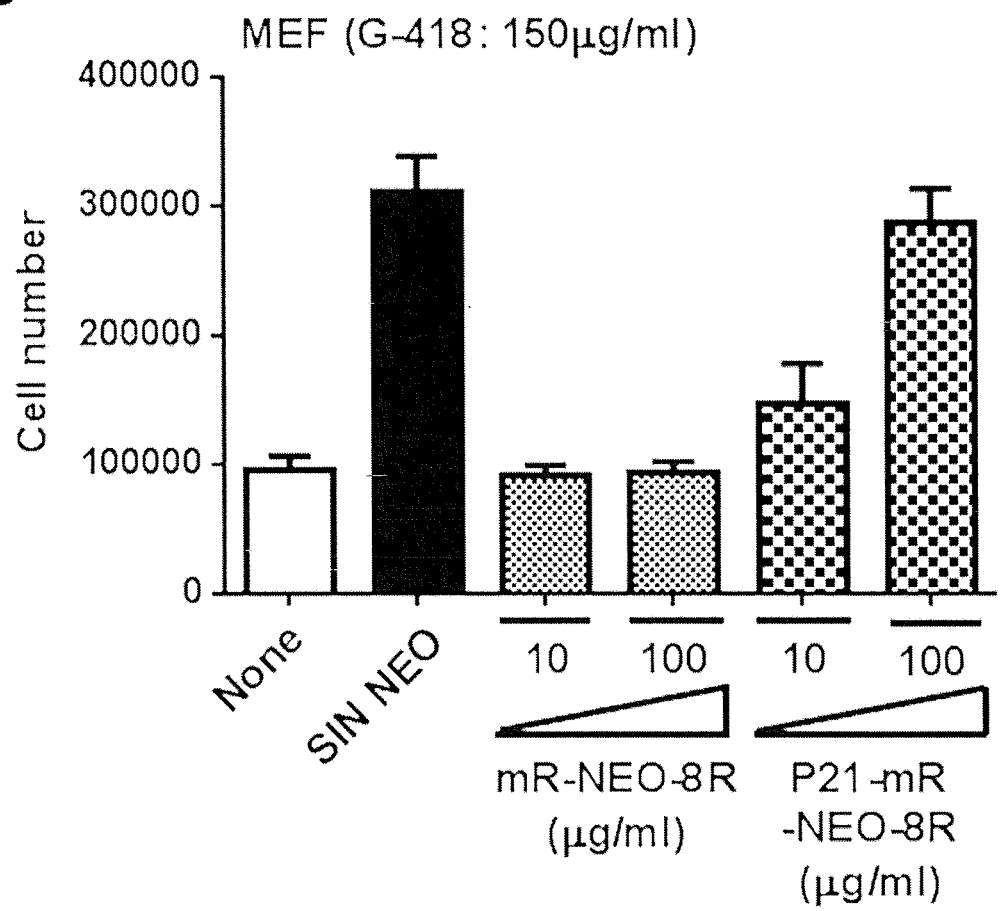

FIG. 24 GET compared to CPP-only transduction of NEO. (a) Schematic of the mR-NEO-8R (CPP-only protein) and P21-mR-NEO-8R (GET protein). (b) P21-mR-NEO-8R maintains living cultures of MEFs under G-418 selection whereas mR-NEO-8R has poor rescue activity. P21-mR-NEO-8R activity is comparable to cells genetically supplemented with SIN NEO (to overexpress NEO). Data shows MEF cell numbers for the 150 µg/ml dose of G-418. Error bars indicate s.d.

Figure 25:
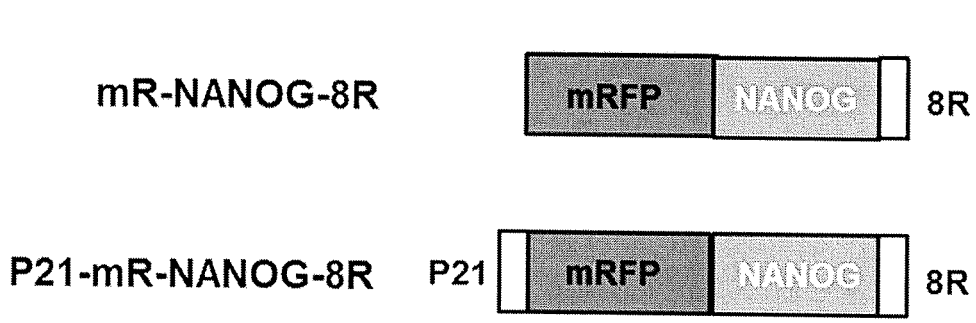
Figure 25:
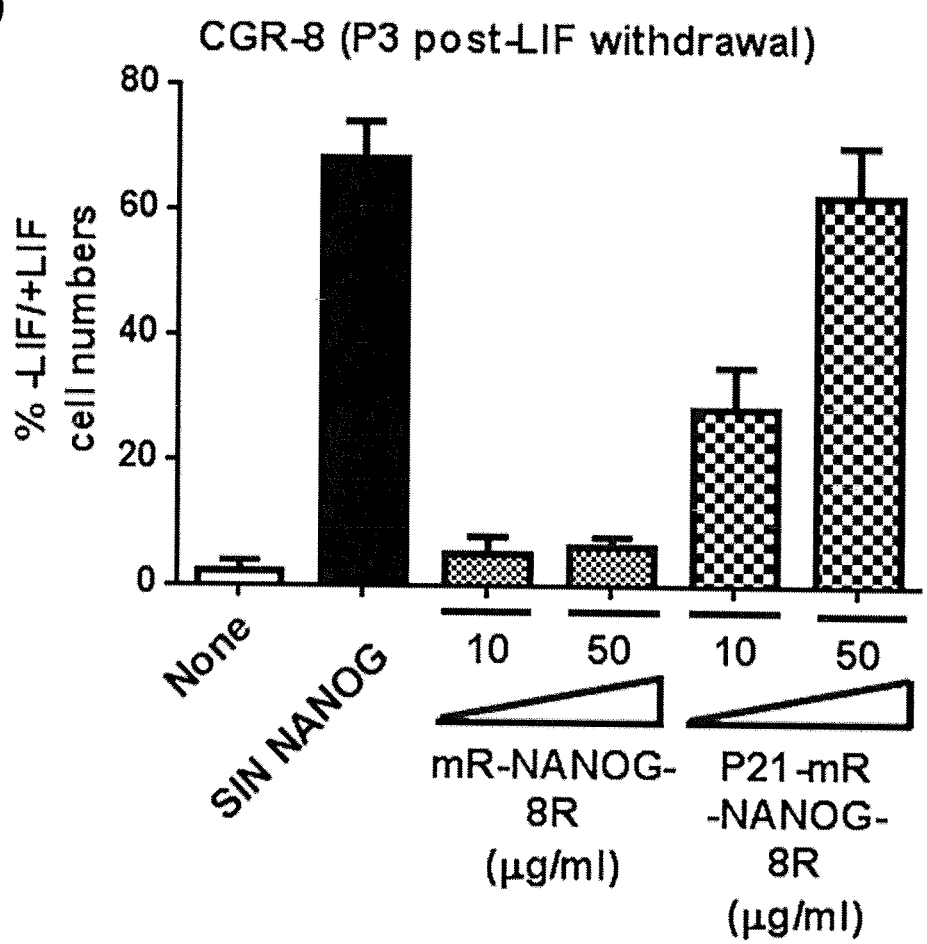

FIG. 25 GET compared to CPP-only transduction of NANOG. (a) Schematic of the mR-NANOG-8R (CPP-only protein) and P21-mR-NANOG-8R (GET protein). (b) P21-mR-NANOG-8R maintains the proliferation of mESCs lacking LIF dose dependently whereas mR-NANOG-8R has poor self-renewal activity. Data shows the percentage of the number of CGR-8 cells cultured without LIF verses those with LIF (% −LIF/+LIF) at passaging. In LIF-deficient CGR-8 cultures proliferation is promoted when supplemented with SIN NANOG (to overexpress NANOG) or transduced with P21-mR-NANOG-8R but poorly by mR-NANOG-8R. Error bars indicate s.d.

Figure 26:
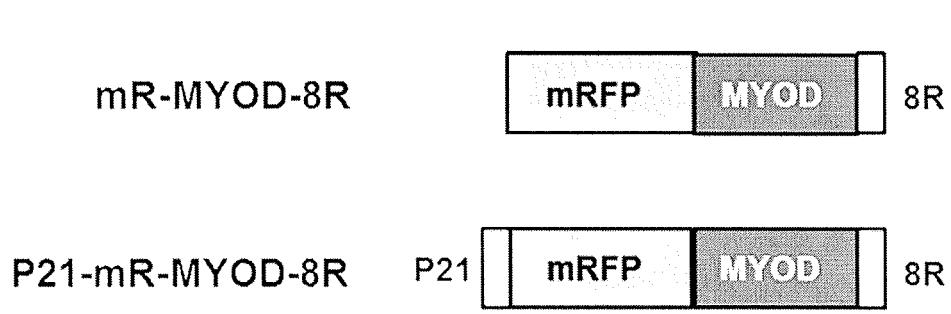
Figure 26:
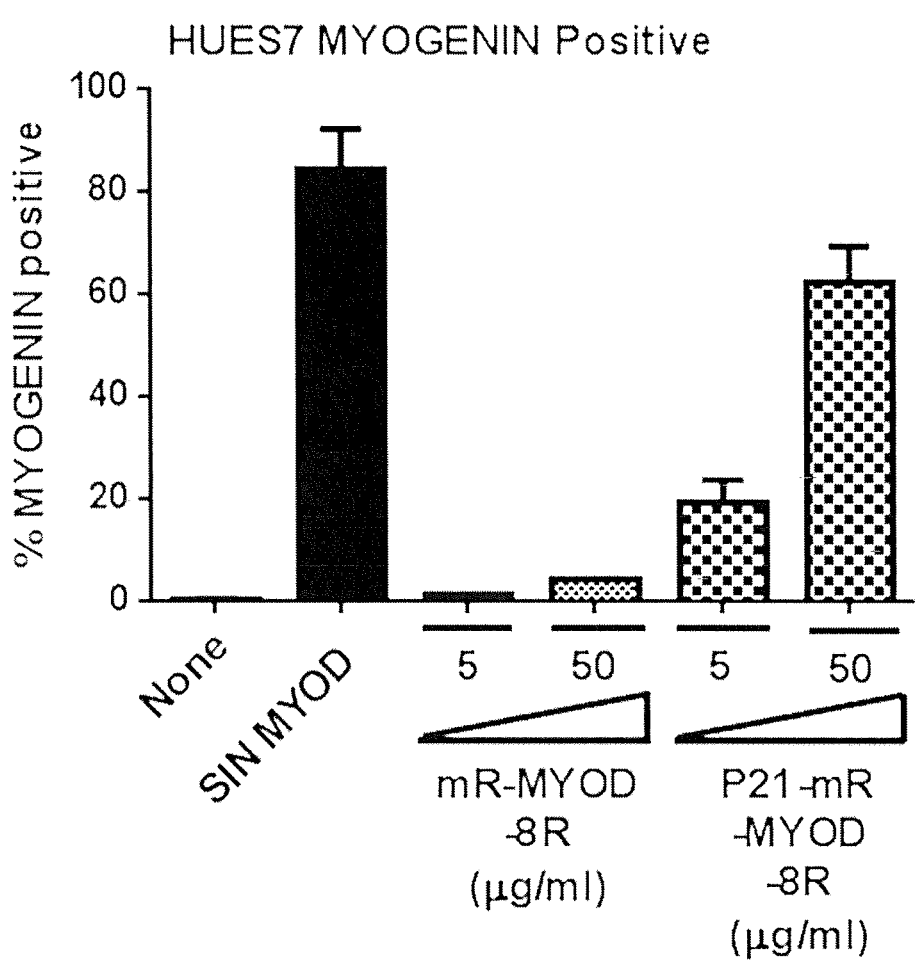

FIG. 26 GET compared to CPP-only transduction of MYOD. (a) Schematic of the mR-MYOD-8R (CPP-only protein) and P21-mR-MYOD-8R (GET protein). (b) P21-mR-MYOD-8R drives myogenic differentiation of HUES7 cells to MYOGENIN positive multinucleated Myotubes whereas mR-MYOD-8R has poor myogenic activity. P21-mR-MYOD-8R activity is comparable to cells genetically supplemented with SIN MYOD (to overexpress MYOD). Data shows the quantitation of the percentage MYOGENIN positive cells using immunolabelling. Error bars indicate s.d.

Figure 27:
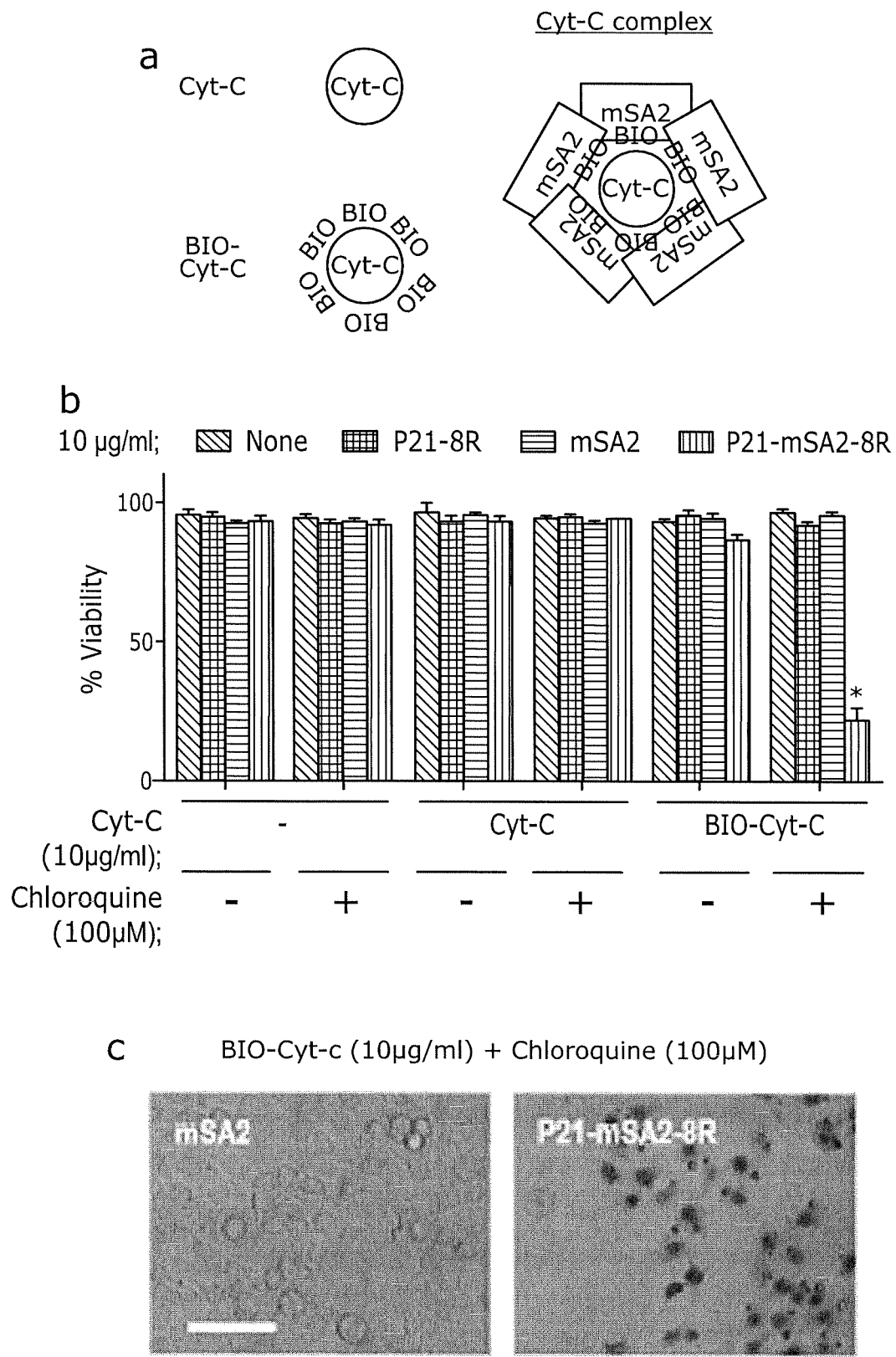

FIG. 27 Delivery of a tissue-extracted pro-apoptotic protein by GET-mSA2. (a) Schematic of bovine heart cytochrome-C(Cyt-C) and biotinylated Cyt-C (BIO-Cyt-C) and Cyt-C complexes with mSA2. (b) Co-incubation of Cyt-C (as a non-interacting control) or BIO-Cyt-C (10 µg/ml) with GET-mSA2 proteins in the presence of Chloroquine (100 µM) to induce apoptosis of NIH3t3s. As assessed by trypan blue exclusion after a 12 hour incubation only the fully interacting and transducing complex (with Chloroquine) mediated loss of cell viability. Error bars indicate s.d. (c) BIO-Cyt-C transduced with P21-mSA2-8R in the presence of chloroquine caused complete loss of cell viability demonstrated by light microscopy. (scale bar, 50 µm).

Figure 28:
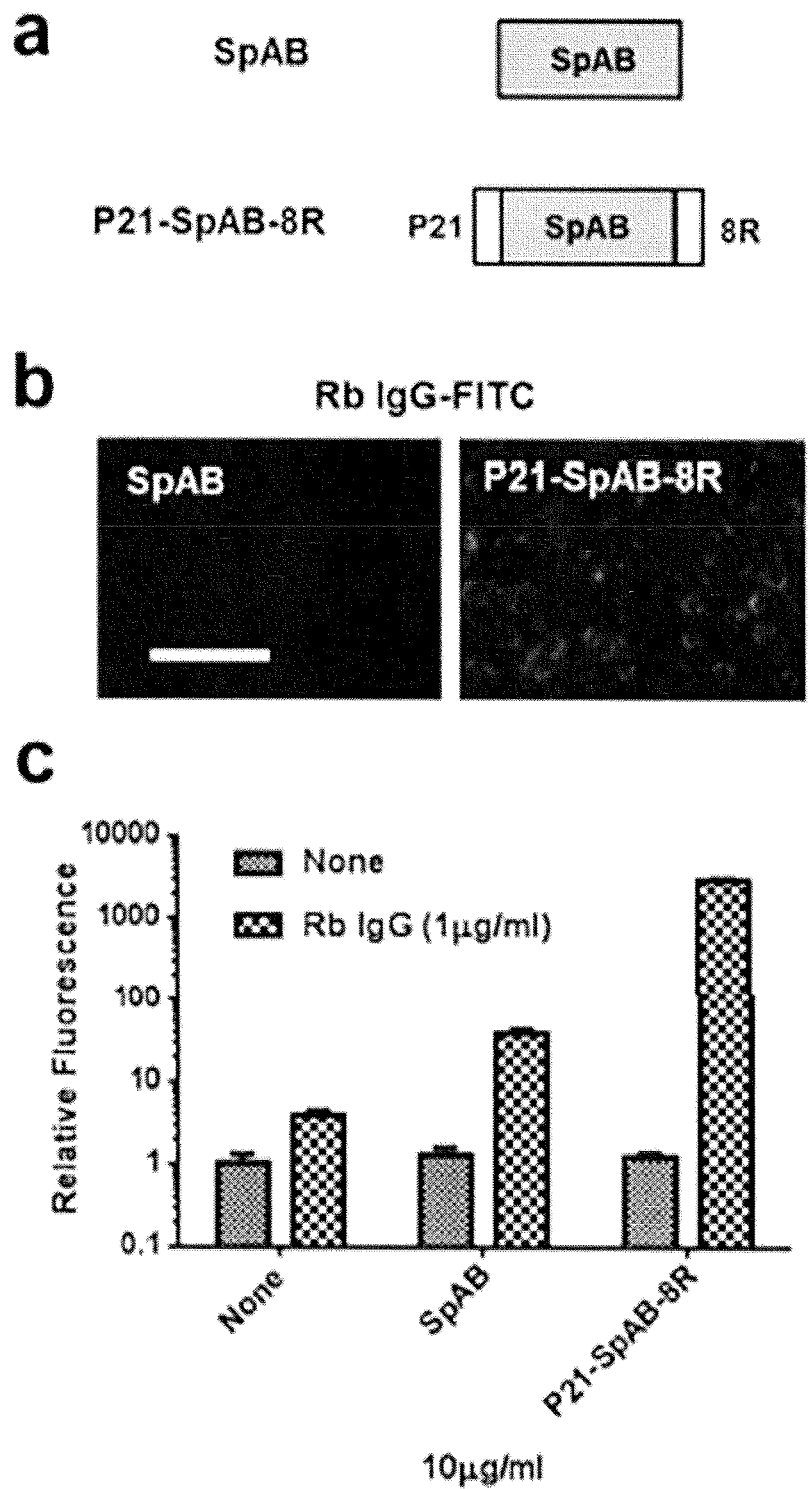

FIG. 28 GET of Antibodies using SpA B domain. (a) Schematic of the SpAB and P21-SpAB-8R proteins engineered to bind to and transduce IgG antibodies. We tested the delivery of an FITC-conjugated Rabbit anti-mouse IgG (Rb IgG-FITC). (b) IgG (1 µg/ml) was taken into NIH3t3 cells poorly by direct incubation or when co-incubated with SpAB (left panel). With co-incubation of P21-SpAB-8R (10 g/ml, right panel), IgG was efficiency delivered to cells visible by fluorescence microscopy (scale bar, 50 µm). (c) Flow cytometry of delivered cells confirmed an increase in IgG delivery of over 2-orders of magnitude. Error bars indicate s.d.

Figure 29:
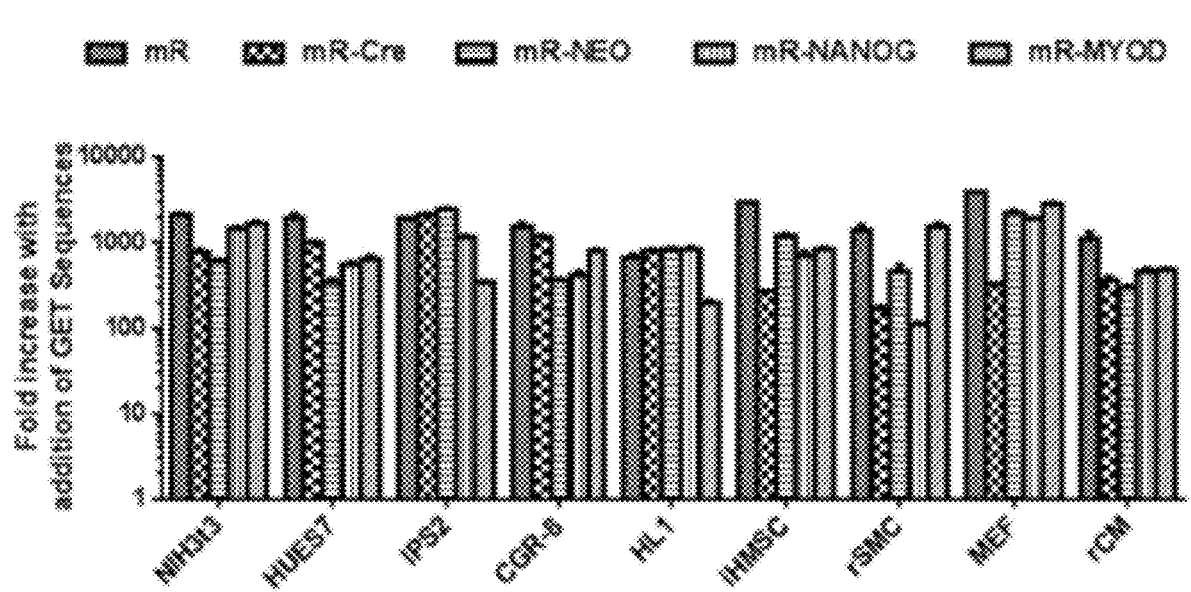

FIG. 29 P21 and CPP addition to cargoes improves delivery by >two-orders of magnitude. Cell lines (described in FIG. 1) including rat aortic smooth muscle cells (rSMC) and neonatal cardiomyocytes (rCMs) were transduced with mRFP fused-variants of cargo proteins (mR, mR-Cre, mR-NEO, mR-NANOG or mR-MYOD) or with cargoes with N-terminally fused P21 and C-terminally fused 8R (CPP) sequences (GET proteins; P21-mR-8R, P21-mR-Cre-8R, P21-mR-NEO-8R, P21-mR-NANOG-8R or P21-mR-MYOD-8R). Transductions were at 20 µg/ml protein for 24 hours in the cell-line standard media. Data shows the fold increase of transduction with addition of GET sequences (P21 and 8R) to the cargoes as assessed by flow cytometry. Error bars indicate s.d.

Figure 30:
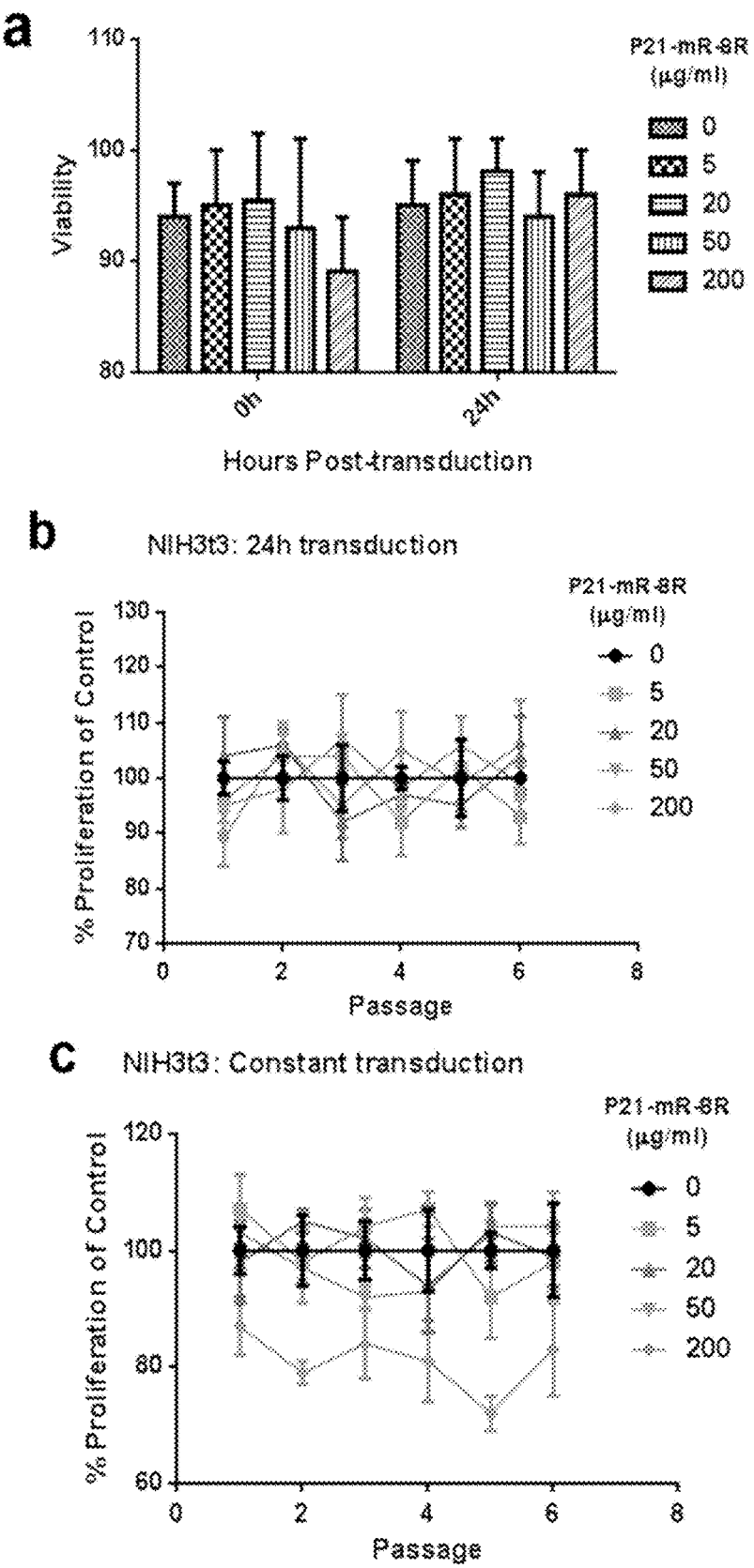

FIG. 30 High level or constant GET-transduction does not affect cell viability (a) Assessment of cell viability by trypan blue exclusion of NIH3t3s transduced for 12 hours with 0-200 µg/ml P21-mR-8R protein either directly after transduction (0 h; left) or 24 hours-post transduction (24 h; right). (b) Assessment of cell proliferation after transduction by passaging and cell counts of NIH3t3s transduced for 24 hours with 0-200 µg/ml P21-mR-8R protein. (c) Assessment of cell proliferation during constant transduction by passaging and cell counts of NIH3t3s transduced with 0-200 µg/ml P21-mR-8R protein (protein refreshed at each passage). Cells were passaged daily and re-plated at 100,000 cells per 12 well. Error bars indicate s.d.

Figure 31:
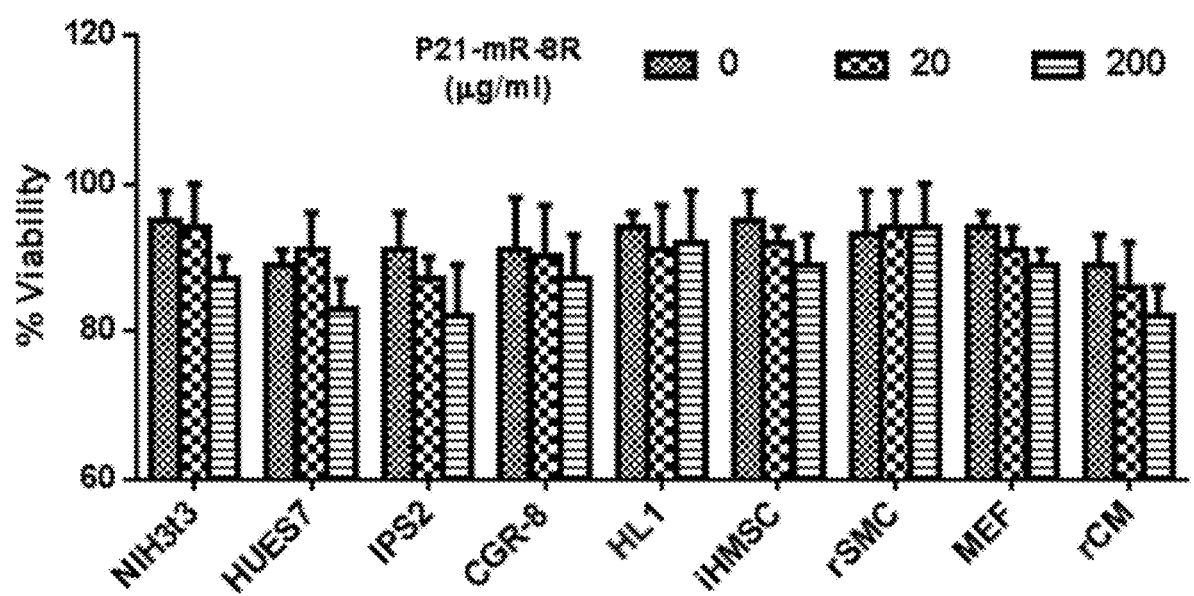

FIG. 31 GET is biocompatible in multiple clinically relevant cell types. Cell lines were transduced with P21-mR-8R at 20 or 200 µg/ml over 24 hours and assessed by trypan blue for cell viability (cell lines were those described in FIG. 1 including rat aortic smooth muscle cells (rSMC) and neonatal cardiomyocytes (rCMs)). Viability remained high in all cell types for both concentrations tested. Error bars indicate s.d.

Figure 32:
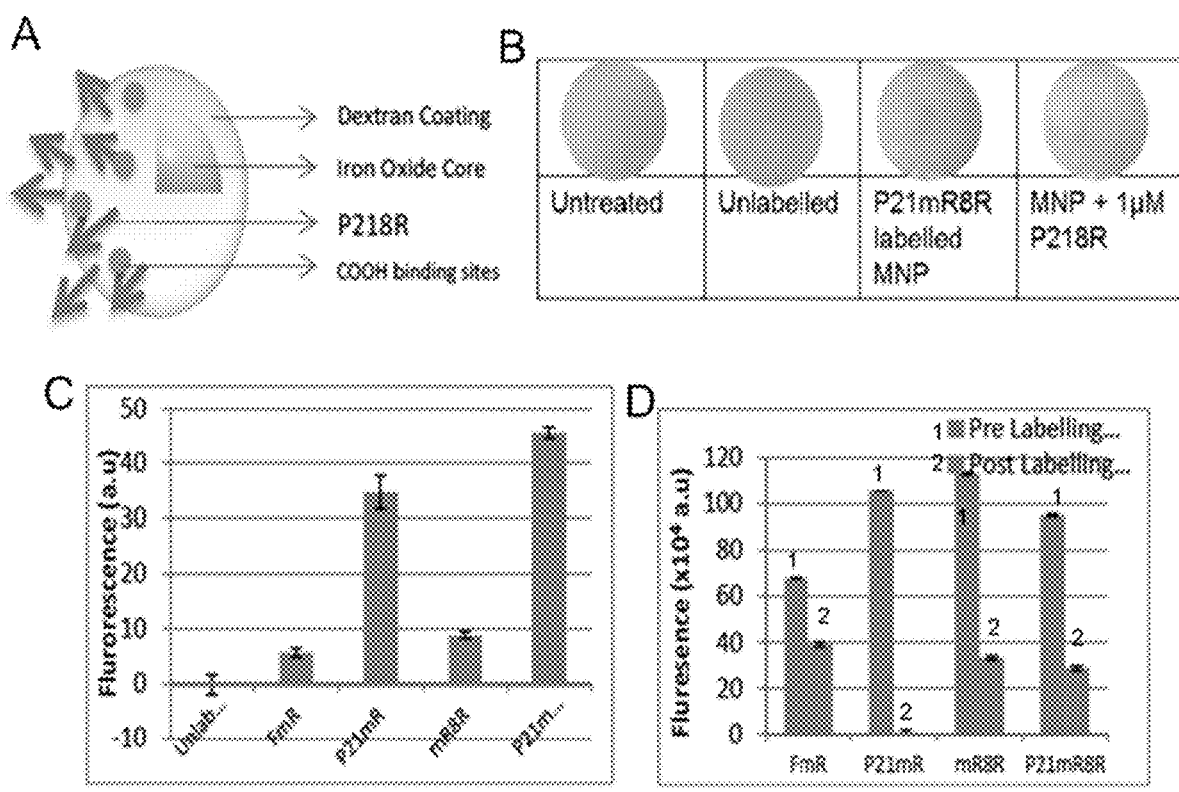

FIG. 32 A: Schematic diagram of a dextran coated nanoparticle, B: Prussian blue staining of 50 µg Nanomag-D nanoparticles labelled with P21mR and particles and protein added separately, C: Fluorescence of Nanomag-D particles labelled with red fluorescent protein, D: Fluorescence of pre and post labelling solutions.

Figure 33:
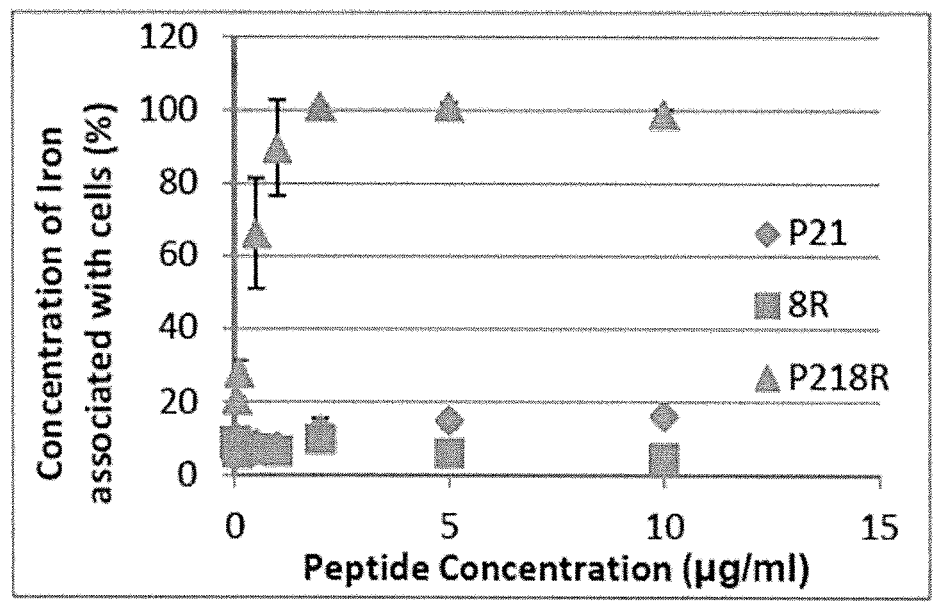

FIG. 33 A: Prussian blue staining of Nanomag particles incubated with 3t3 cells for 24 hours, B: Iron assay results for the amount of iron per cell after the 24 hour incubation.

Figure 34:
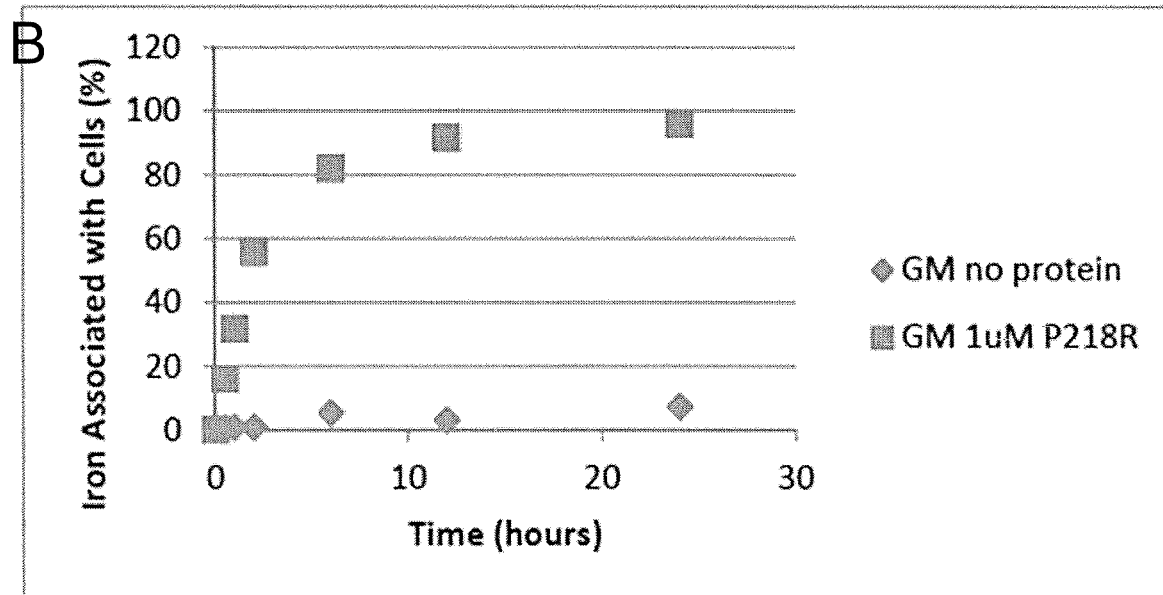

FIG. 34 A: Prussian blue staining of nanomag-D particles incubated in 3t3 cells for varying times, B: The iron assay quantification results.

Figure 35:
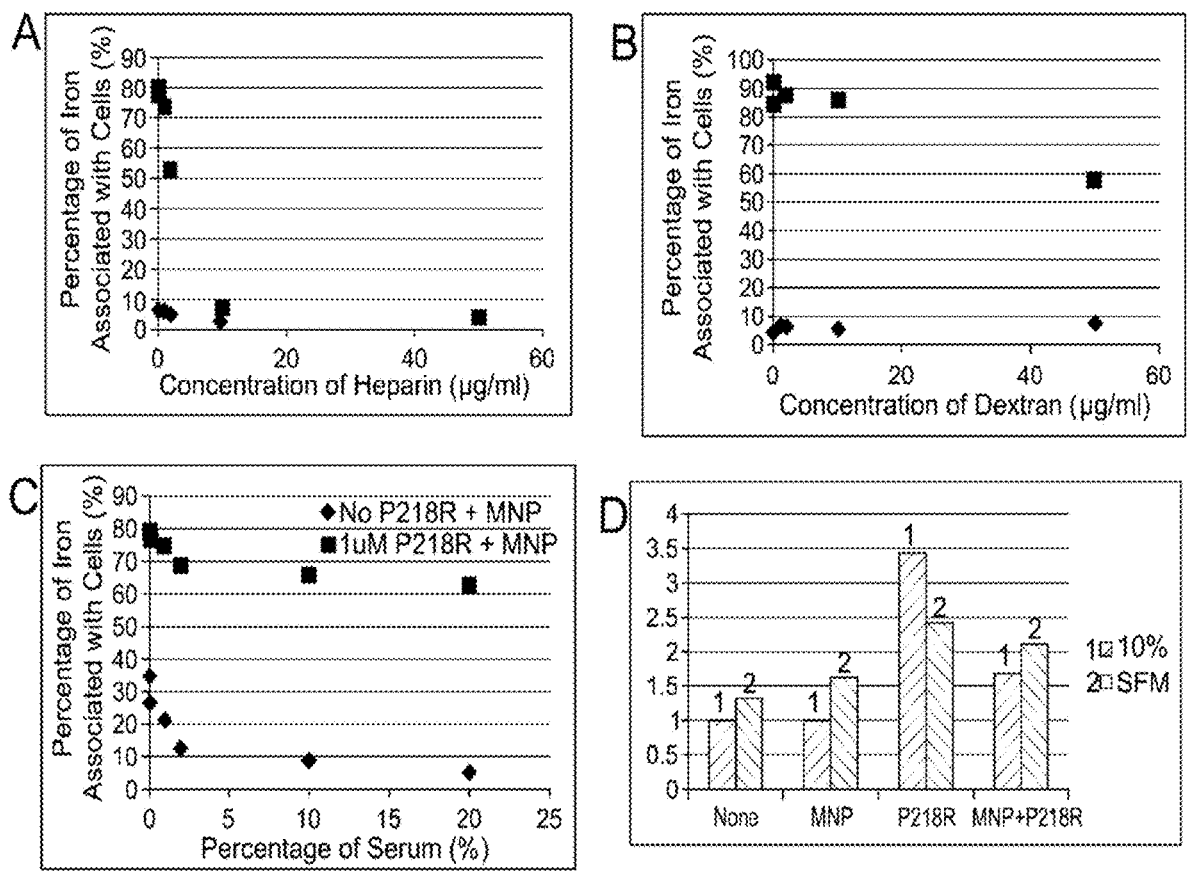
Figure 36:
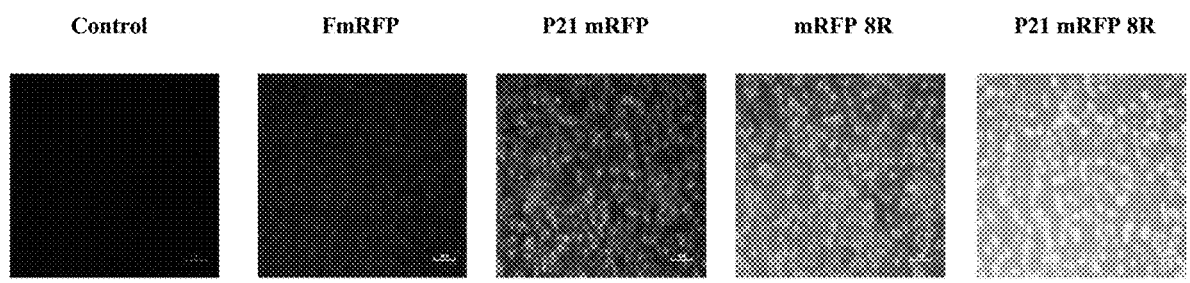

FIG. 35 A: 3t3 cells incubated with 50 µg nanoparticles, 1 µM of P218R and various quantities of heparin analysed by iron assay. B: incubated with dextran. C: incubated with varying amounts of serum. D Fluorescence of 3t3 cells after incubation with Fitc-BSA FIG. 36 GET-mediated enhanced delivery of mRFP to cells via P21 mRFP 8R peptide. Fluorescence microscopy images of NIH3T3 cells treated with FmRFP, P21 mRFP, mRFP 8R and P21 mRFP 8R peptides (20 g/ml) for twelve hours. The images also include cells that weren't treated with any peptides, as a control. Scale bar, 100 µm.

Figure 37:
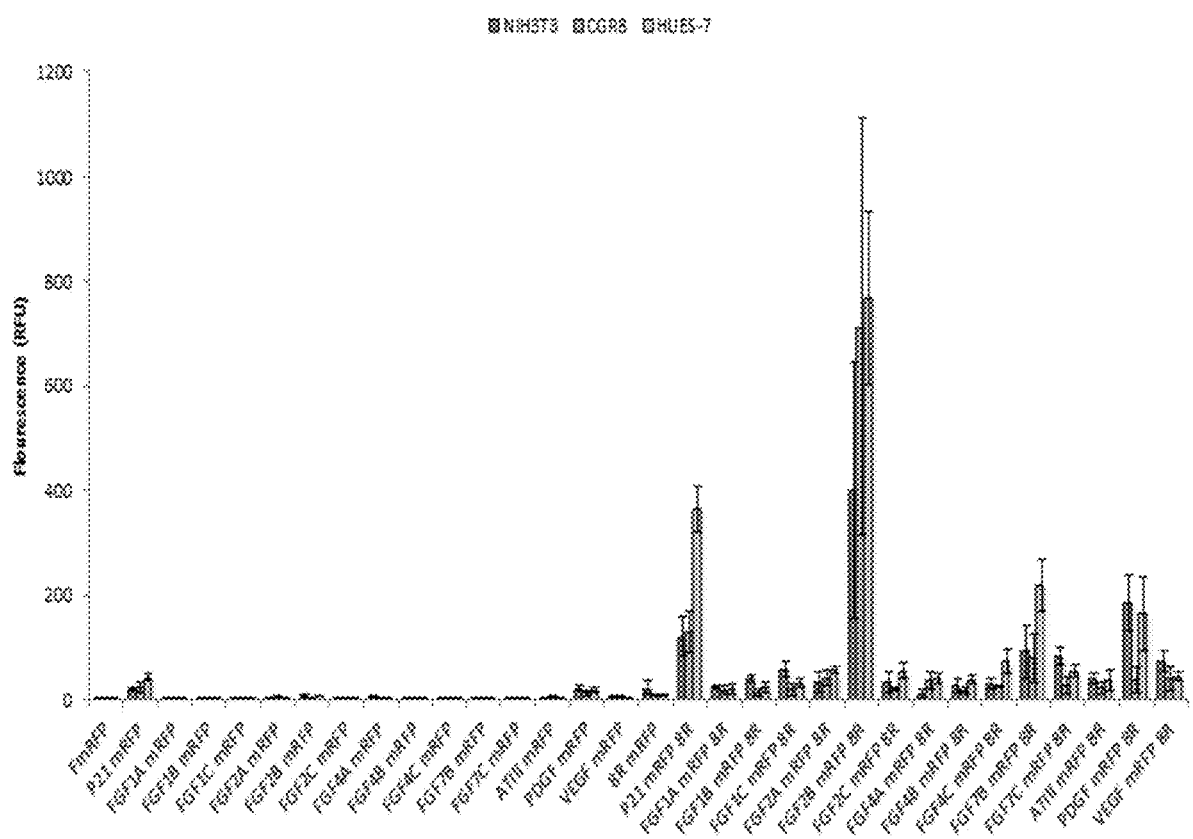

FIG. 37 Graph showing NIH3T3, CGR-8 and HUES7 cells treated with mRFP conjugated peptides (20 ug/ml) for 12 h. Flow cytometry analysis was used to quantify fluorescence (relative fluorescence units (RFU)) of cells. Error bars indicate s.d, n=3.

Figure 38:
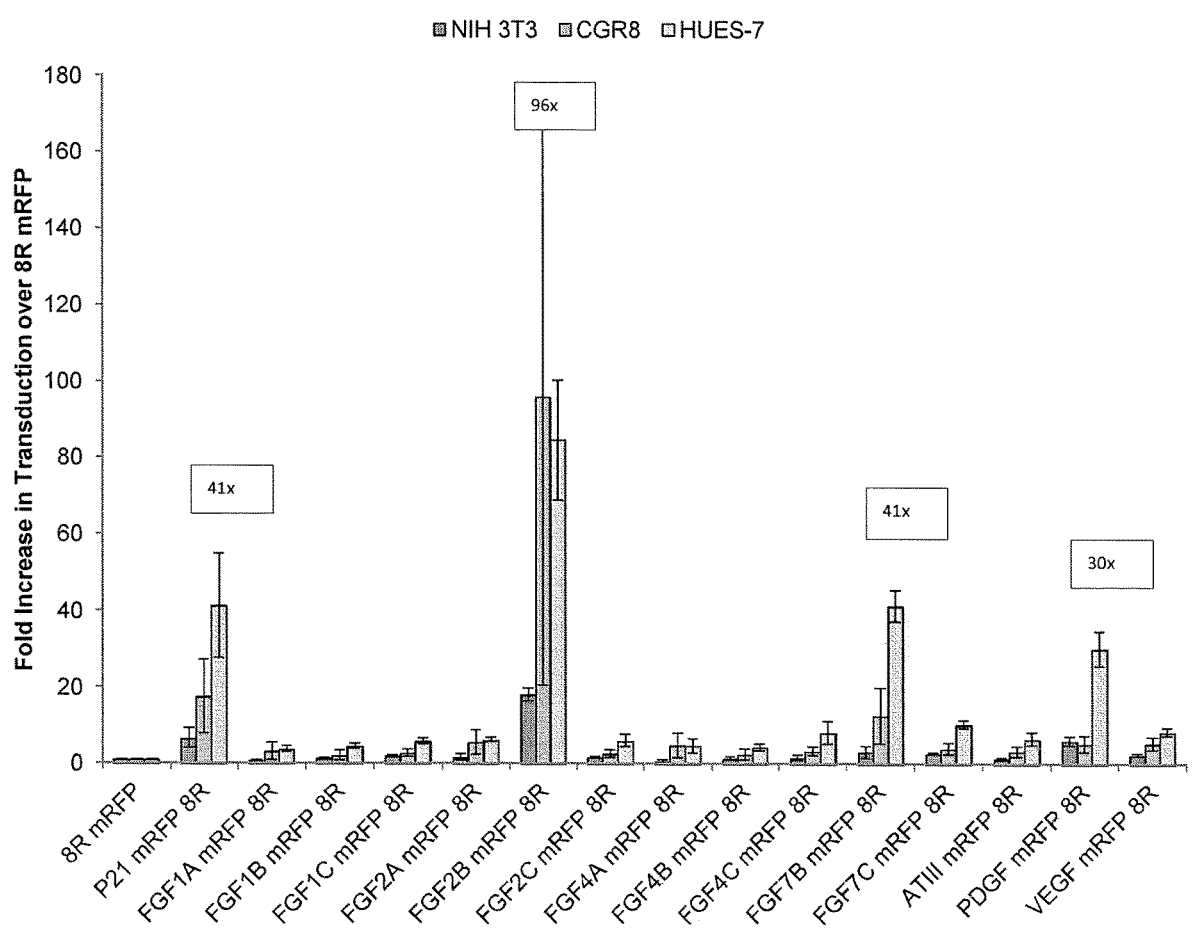

FIG. 38 Graph showing the increase in transduction of mRFP into cells by modified CPPs (HS-GAG binding domain mRFP 8R) over an unmodified CPP (mRFP 8R). NIH3T3, CGR-8 and HUES7 cells were treated with mRFP conjugated peptides (20 ug/ml) for 12 h. Error bars indicate s.d, n=3.

Figure 39:
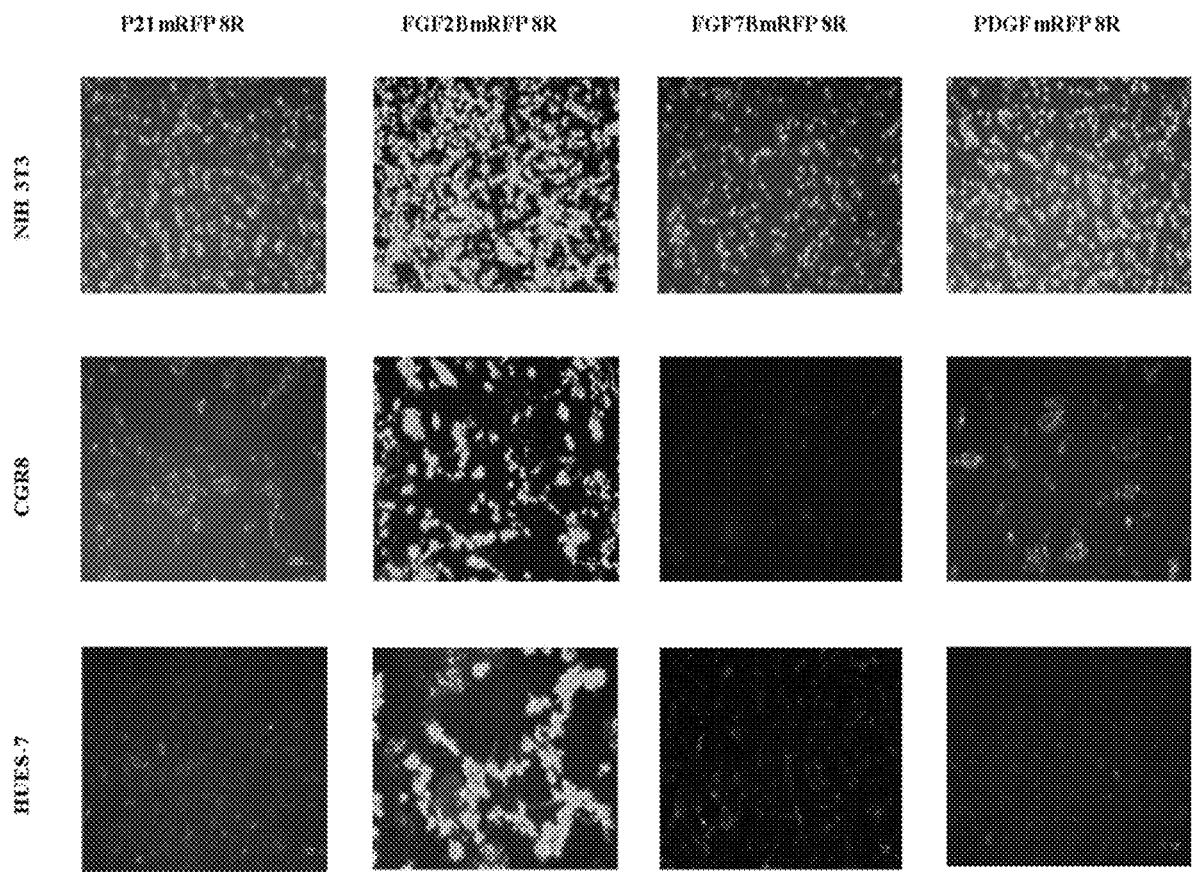

FIG. 39 Efficient delivery of mRFP to cells via modified peptides shown to promote GET. Fluorescence microscopy images of NIH3T3, CGR8 and HUES-7 cells treated with P21 mRFP 8R, FGF2B mRFP 8R, FGF7B mRFP 8R and PDGF mRFP 8R peptides (20 µg/ml) for twelve hours. Scale bar, 100 µm.

Figure 40:
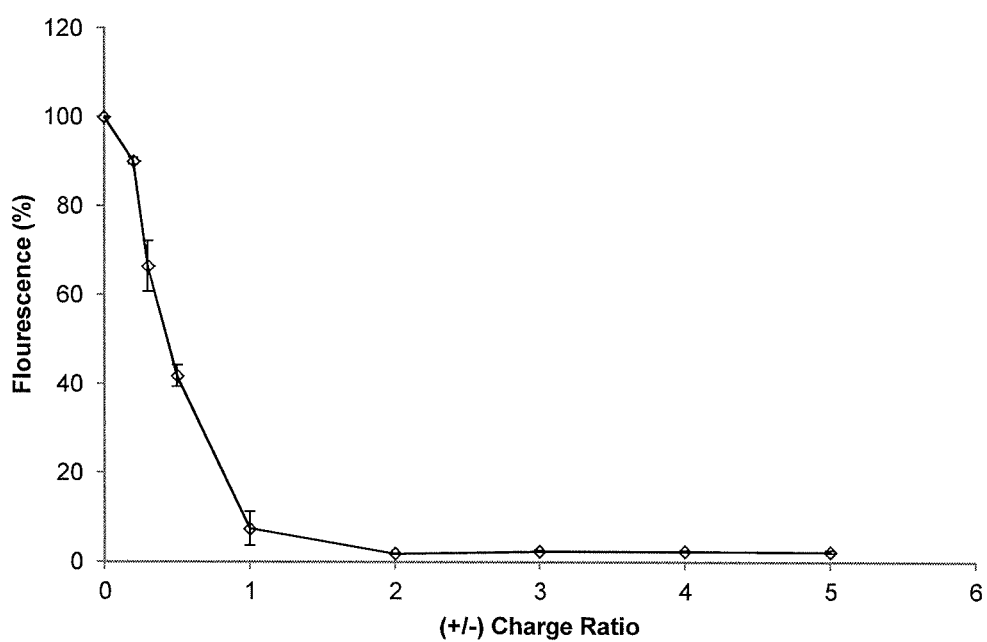

FIG. 40 Optimization of (+/−) charge ratio of P21 LKL5 8R to pSIN GFP using YO-PRO-1 assay. Graph shows a decrease in % of fluorescence as P21 LK15 8R binds pSIN GFP. Error bars indicate s.d., n=3.

Figure 41:
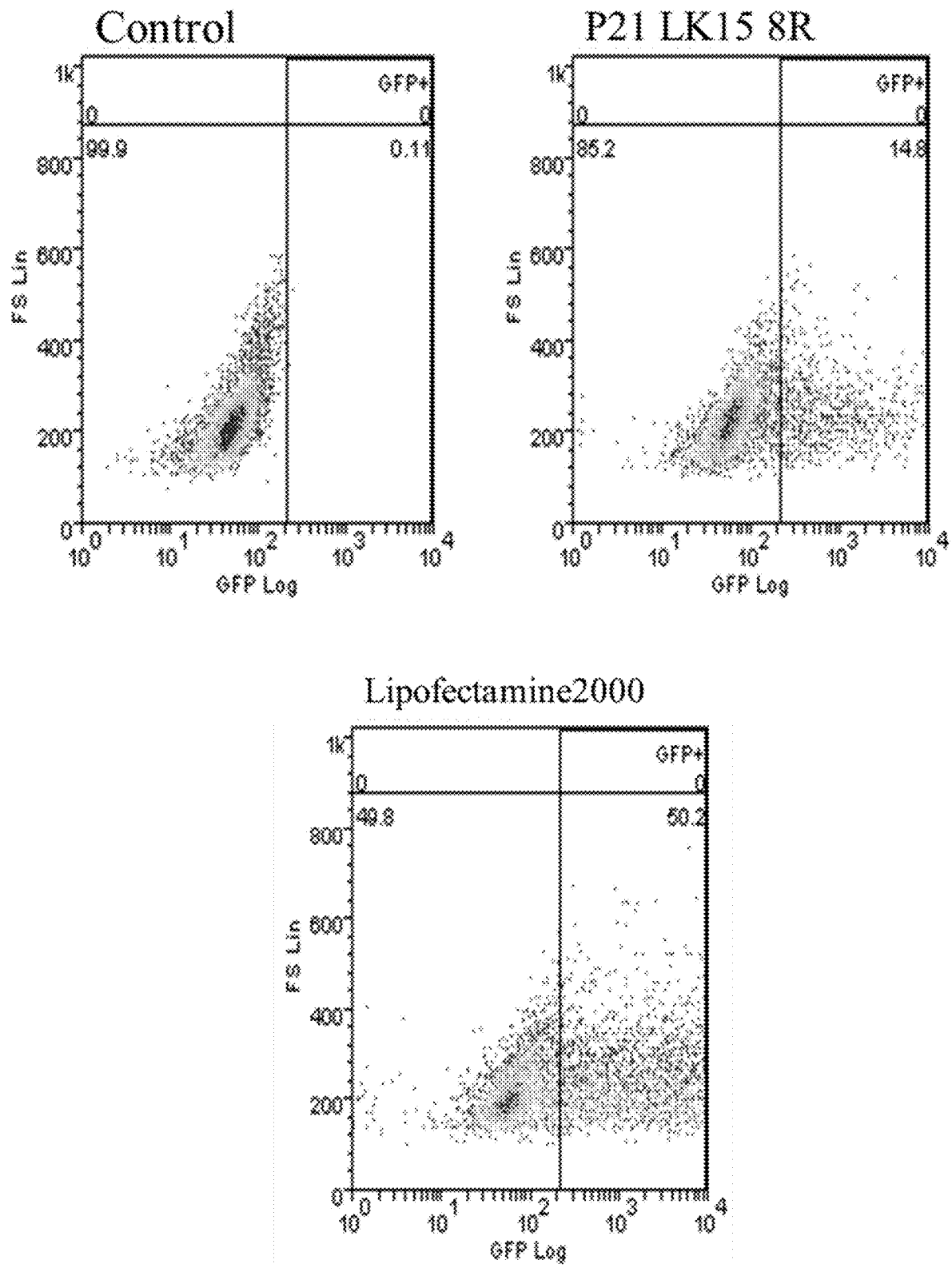

FIG. 41 Examples of flow cytometry dot plots showing GFP expression of NIH3T3 cells following transfection with pSIN GFP for 6 h. Following transfection, cells were fixed at a 48 h time-point. Flow cytometry analysis was used to quantify % of GFP positive cells.

Figure 42:
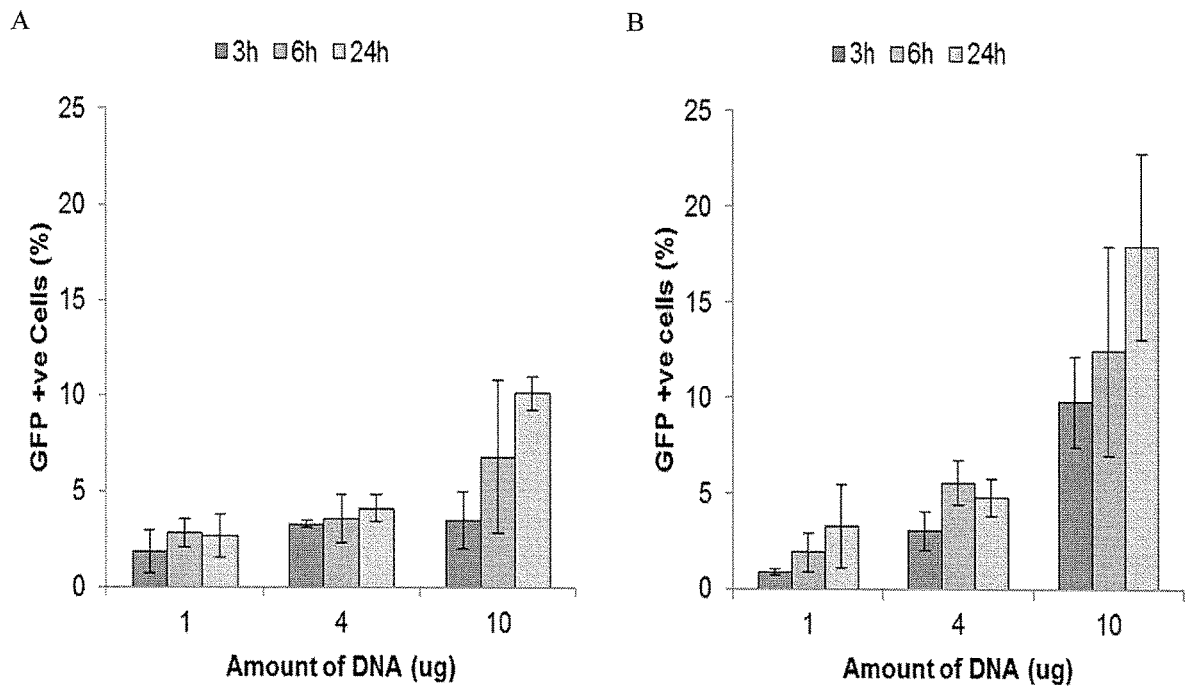

FIG. 42 Transfection optimization of pSIN GFP into NIH3T3 cells by P21 LK15 8R peptide. Cells were treated with the optimum (+/−) charge ratio of P21 LK15 8R to pSIN GFP of 2:1, respectively. Optimization was carried out at varying transfection times (3, 6 and 24 h) in (A) 10% serum transfection media (B) serum free transfection media. Following transfection, cells were fixed at a 48 h time-point. Flow cytometry analysis was used to quantify % of GFP positive cells. Error bars indicate s.d., n=3.

Figure 43:
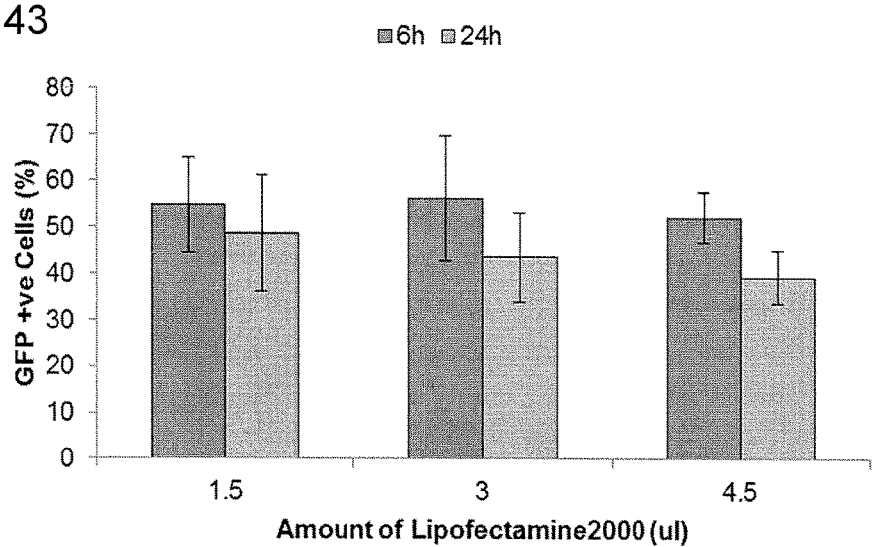

FIG. 43 Graph showing the optimization of the transfection of pSIN GFP into NIH3T3 cells by Lipofectamine2000, in serum free conditions. Flow cytometry analysis was used to quantify % of GFP positive cells. Error bars indicate s.d., n=3.

INTRODUCTION

Human pluripotent stem cells (HPSCs) comprise HESCs derived from the inner cell mass of the pre-implantation embryo, and HiPSCs generated by epigenetic reprogramming of somatic cells {Robinton, 2012 #30}. The ability to control the behaviour and differentiation of these cells efficiently and reproducibly underpins current efforts in regenerative and personalized medicine. A transcription-factor driven transgenic method has been previously described to directly programming gene-regulatory networks in HPSCs to drive cardiac differentiation and create contractile Cardiomyocytes {Dixon, #11}. Many transgene-driven methods to control cell behaviours such as genome reprogramming {Takahashi, 2007 #82}, self-renewal {Chambers, 2003 #70}, differentiation {Dixon, #11}, apoptosis {Mohan, 2013 #83}, proliferation {Zhao, 2013 #85} or migration {Deboux, 2013 #84} have been described. These all involve the integration of DNA to allow exogenous gene expression usually using viral vectors or transient DNA transfection which is inefficient and may also lead to genome modification, Approaches such as RNA transfection {Warren, 2010 #4} or PTD-mediated protein delivery {Zhou, 2009 #72} are therefore an attractive alternative with controlled stoichiometry and have no possibility of genome integration {Gump, 2007 #39}. It was an aim to develop PTD-technology to allow robust delivery of bioactive proteins into pluripotent stem cells which could replace present technologies and be used to improve the adoption of HPSCs for regenerative medicine applications.

Results

Isolation of P21, a HBD that enhances PTD function through HS-GAG interaction A focus was improving the initial PTD interaction and lipid-bilayer transduction of cargo proteins rather than on endosomal escape. Initially, monomeric red fluorescent protein (mRFP1) was employed as a self-reporting cargo which is readily expressed and purified in *Escherichia coli* (FIG. 1a). Investigation led to the determination that TAT and 8R PTDs interact with the cell membranes of mESCs, HESCs and HiPSCs (FIG. 8a) but have very poor transduction of cargo (~1-3 fold over control) (FIGS. 1 & 8b). This was in comparison to extensively tested cell-lines (such as NIH3t3, C2C12 and mouse embryonic fibroblasts) which showed efficient delivery (~5-50-fold over control, p<0.01) (FIG. 1). Previous reports have demonstrated the functional delivery of PTD-tagged proteins in pluripotent stem cells with different degrees of robustness {Do Kwon, 2005 #74; Liang, 2013 #73}. The success achieved in these studies was hypothesized to be due to very minimal amounts of efficacious protein required, protein delivery into the differentiated derivatives rather than the starting population, or the use of vast amounts of protein to elicit low-level functionality.

It was aimed to improve binding and ultimately transduction of cargo proteins into these target cell-types. Several short peptides were screened which have been reported to interact with molecules known to be present on mESC, HESC or HiPSC membranes including integrins, CD markers and GAGs. Peptides were fused N-terminally to mRFP1, expressed, affinity purified and incubated with the three cell-types. Screening of 12 variants yielded one which clearly increased localisation of mRFP1-fluorescence (mR) to cells and their membranes, termed P21 (KRKKKGKGLGKKRDPCLRKYK (SEQ ID NO: 1)) (FIG. 2). Interestingly this peptide also demonstrated transduction activity as evidenced by punctate intracellular fluorescence indicative of endosomal localisation (FIG. 2b,c). P21 was derived from HB-EGF, which belongs to the EGF family of cytokines. HB-EGF shows a strong affinity to heparin and binds to the same receptor as EGF and TGF-α {Sakuma, 1997 #76}. The interaction of HB-EGF with cell surface HS-GAG is essential for its optimal binding to EGFR and for promoting its growth/migratory activity toward vascular smooth muscle cells {Higashiyama, 1993 #90}. Mutagenesis and protease digestion of recombinant HB-EGF, coupled with analyses using synthetic peptides and heparin, revealed the P21 sequence in the amino-terminal region of the soluble HB-EGF is responsible for its binding to heparin so is considered a typical HBD {Thompson, 1994 #77}. In addition, P21 also interacts with cell surface HS-GAG but not the EGFR which is mediated by other sequences in HB-EGF. Therefore, a short 21-residue peptide, P21, was isolated, which enhances the association of a fluorescent reporter to both mouse and human pluripotent stem cells.

To confirm direct binding of P21 to Heparin a binding assay was developed using Heparin-sepharose beads (FIG. 9). P21-tagged mR was efficiently sequestered by Heparin-sepharose unlike untagged mR (96.2±5.3%; p<0.01). This could be reversed by co-incubating with free Heparin in a dose dependent manner. The fact an HBD was isolated is interesting; HS-GAGs have long been considered important in the process of PTD-mediated transduction. However the exact role of HS-GAG in transduction is presently a point of contention with the most recent hypothesis being that HS-GAG is merely important in transduction by directly binding to PTDs and concentrating them on the membrane; this enhances lipid-bilayer translocation but is not necessary for its occurrence {Gump, 2010 #2}.

Negatively charged sulphated proteoglycans and glycoproteins are present on all mammalian cells. However they are differently modified and specific variants are ubiquitous or present on very specific cell types {Lindahl, 1998 #56}. GPI-anchored proteoglycans and glycoproteins are present in lipid rafts suggesting that PTDs may have increased avidity for certain proteoglycans or perhaps that PTDs bind directly to cholesterol membrane constituents which trigger macropinocytosis. It is also possible that the P21-peptide may have specific avidity to certain HS-GAG forms and could recognise the same motifs at PTDs.

P21-mediated binding of cell membranes was tested to determine if it could enhance PTD-mediated transduction of mR by combining both moieties in one molecule (FIG. 2a). P21-mR-8R was cloned, expressed and purified, and its activity compared to P21-only (termed P21-mR) or 8R-only (mR-8R) proteins (FIG. 2a). Data demonstrated that the inclusion of both P21- and 8R-moieties synergized in the same protein to significantly enhance the fluorescence of all cell-lines tested. (FIG. 2b). Importantly mouse and human pluripotent stem cells (CGR-8, HUES7 and IPS2) and cardiomyocytes (HL1) only transduced efficiently with the inclusion of P21-tag, and both tags synergized to produce the high-levels of transduction similar to that seen in other cell lines (FIG. 2c). These motifs were also placed in tandem at N- and C-terminal of mRFP (P21 or 8R first; P21-8R-mR, 8R-P21-mR or mR-P21-8R, mR-8R-P21) or switched their termini (i.e. 8R-mR-P21) with all variants demonstrating similar synergy and cell transducing behaviour (FIG. 10) as seen for P21-mR-8R. Furthermore 8R was swapped for alternative well characterised PTDs (TAT, 8K and 8RQ; {El-Andaloussi, 2005 #36}) and showed that these also synergized with P21 (FIG. 11).

By incubating cells with protein for different timings and including a post-culture period it could be efficiently distinguished between fluorescence signal produced at the cell surface with that internalised (FIG. 2d). Cells demonstrated membrane localisation of fluorescence with short incubation times (1 hour), termed 1 h. With this short incubation and a subsequent culture period (1 hour with a 5 hour post-culture), termed 1 h-5 h we observed near exclusive intracellular fluorescence indicating transduction. Using longer incubation times (6 hours), termed 6 h, cells exhibited strong punctate peri-nuclear fluorescence indicative of endosomal-mediated transduction. This synergistic delivery mechanism is described as GAG-binding enhanced transduction (GET) or otherwise Heparan-sulfate enhanced transduction domain (HETD)-mediated delivery.

GET Requires the Presence of Trypsin-Sensitive and Detergent-Soluble Cell Membrane Molecules To evaluate the mechanism of GET interaction and uptake by cells, a series of experiments were performed which were previously used to assess PTD. To assess which cell membrane components are required for both initial cell association and transduction by HETDs it was determined whether similar transduction would be obtained by enzymatic depletion of cell membrane before transduction. Cells were pre-treated with proteolytic enzyme trypsin and tested cell transduction using the 1 h-5 h regime protocol. Enzymatic removal of cell-surface proteins potently inhibited GET/HETD-mediated transduction (~8.4-fold; $p<0.05$) (FIG. 2e). In contrast, non-enzymatic release of cells from the culture plastic using ionic cell dissociation solution (CDS) did not alter HETD-mediated uptake.

Next it was tested if depletion of detergent-soluble cell-membrane molecules would also have a similar effect on transduction. Cells were pre-incubated in 0.1% (v/v) Triton X-100 and using the 1 h-5 h protocol a decrease (~2.2-fold; $p<0.05$) was observed in GET (FIG. 2f) without a decrease in viability. Therefore, it was demonstrated that both protein and detergent soluble moieties on the cell membrane affect the efficacy of protein transduction through P21- and PTD-synergy in GET/HETD-transduction.

GET Requires the Presence of Cell Membrane HS-GAG

P21 is a HBD, and PTDs due to their cationic nature bind to negatively charged HS-GAGs. It was further aimed to confirm the mechanism of GET/HETD-mediated transduction by either enzymatic depletion of HS-GAG or competition with free GAGs (FIG. 3). Heparin prevented the cell-surface binding of HETD proteins and strongly inhibited transduction (99.8±2.1%; $p<0.001$) (FIG. 3a, b). Chondroitin sulphate (CS) A, B or C had little effect on either activity (FIG. 3b). CS-B and -C has previously been shown to affect the binding of PTD-proteins {Wadia, 2004 #25}. It was confirmed that Heparin, CS-B and -C have significant activities in inhibiting PTD-only protein transduction (8.1-, 2.4- and 4.1-fold, respectively; $p<0.05$) but that only Heparin affected GET/transduction mediated by HETDs (FIG. 3b and FIG. 12). P21-tagged proteins exhibit a dose-dependent inhibition of transduction with increasing concentrations of Heparin in NIH3t3 and CGR-8 cells (FIG. 3c & d, respectively). 8R-only protein is inhibited only with the highest doses of competing Heparin. In the context of the HETD protein (P21-mR-8R) it is therefore likely that the avidity of P21 for cell membrane HS-GAGs far outweighs that of CS-GAGs for PTD binding. Therefore, it can be concluded that Heparin and HIS-GAGs are the major target of P21 to enhance PTD activity.

To further understand the requirement of cell-membrane HS-GAG for P21-activity cells were treated with HS-lyase enzyme, heparinase III, and tested cell transduction using the 6 h protocol (FIG. 13). Enzymatic removal of cell-surface HS-GAGs potently inhibited GET/HETD-mediated transduction (at 1 U/ml 97.2±3.4%; $p<0.001$). In contrast, neuraminidase treatment which depletes sialic acid GAGs (SA-GAGs) did not alter GET/HETD-mediated uptake. The analysis was further extended to define the effect of serum on transduction (FIG. 13b). It has previously been shown that serum has a negative effect on PTD-mediated delivery {Kaplan, 2005 #43}. By incubating serum with affinity purified-P21 peptide on sepharose its inhibitory effect on HETD-mediated recombination was capable of being removed (10% v/v, ~7.3-fold increase with depletion; $p<0.01$) (FIG. 13c). This indicates that serum is likely to contain GAGs which act as competitive molecules for P21-membrane binding. These can be removed by pre-depletion using P21-bound sepharose. This inhibitory activity could be reconstituted by addition of soluble Heparin to depleted-serum further strengthening this hypothesis (FIG. 13d). In addition to enzymatic depletion, the HS-GAG requirement was confirmed by treating cells with Sodium Chlorate, a potent inhibitor of HS synthesis which also potently prevented HETD-mediated protein delivery (~7.6-fold; $p<0.05$) (FIG. 14). Therefore, it was demonstrated that HS-GAG depletion specifically affects the efficacy of protein transduction and therefore endogenous HS-GAGs are important molecules for GET/HETD-mediated protein delivery. Also that exogenous HS-GAG are highly inhibitory to this process.

HS-GAGs has a complex sugar structure, consisting of a backbone of repeating disaccharides of glucuronic acid (GlcUA) and N-acetylglucosamine (GlcNAc), polymerized by a heteromeric complex of EXT1/EXT2 enzymes {Lawrence, 2008 #51}. To further investigate the role of HS-GAGs on GET/HETD-mediated transduction EXT1−/− mESCs were used, which lack endogenously synthesized cell membrane HS-GAG {Lin, 2000 #78}. When cultured in conventional mESC media (containing 20% w/v FCS) a significantly lower transduction in EXT1−/− mESC versus wild-type CGR-8 mESCs was observed (~6.8-fold; $p<0.01$) (FIG. 3e,f). This was also apparent when cells were cultured in serum-free conditions likely to be due to interference from free GAGs in FCS (~5.6-fold; $p<0.01$). Transduction/ GET was not absent in EXT1−/− cells (~9.7-fold over mR control levels) nor was the initially binding of P21-containing proteins. It was hypothesized that this may be due to incorporation of exogenous soluble serum-GAGs into the deficient EXT1−/− cell membrane. This is likely as subsequence Heparinase III treatment further inhibits binding and transduction in these cells.

GET Generates Higher Intracellular Protein Levels than Lentiviral Transgenesis

Several studies have concluded that PTD-mediated transduction is sufficiently refined to allow the transport of biologically active cargos for clinical studies. These now include trials of cancer therapies {Gump, 2007 #39}, siR-NAs {Meade, 2007 #37} and in vivo imaging technologies {Bullok, 2006 #79}. As well as the benefits of avoiding genomic modification, if PTD-mediated transduction is to be preferential to gene-therapy approaches it must achieve the delivery of high-levels of molecule, be amenable to control of protein levels over short time-frames and also allow cell-type specific delivery. The levels achieved in cells by PTD- or GET/HETD-delivery were compared to those achieved by efficient lentiviral transduction {Dick, 2011 #10} and exogenous expression of mRFP1 (with stable EF1α-promoter driven) (FIG. 15). To achieve this soluble protein was extracted from transduced cells and measured amounts by fluorometry (FIG. 15a), or flow cytometry was used (FIG. 15b). Using 6 hour incubations, mR-8R levels were several times lower (~3-fold; p<0.05) than that achieved by viral transgenesis even at the highest tested doses (200 g/ml). However P21-mR-8R levels under the same conditions were ~16-fold higher (p<0.001) than transgenic cells. Importantly of the amount of P21-mR-8R protein incubated a significant proportion was recovered as soluble intracellular protein (~46±3.5 μg/200 μg used; ~2311.7% recovery). It is important to note that under these conditions transduced cells appear red/purple in colour under normal light, demonstrating the efficient enrichment of large quantities of HETD-tagged/GET proteins in cells.

The rate at which these proteins were concentrated in cells was investigated by measuring the depletion of fluorescence in media over the incubation period (FIG. 16). Proteins were diluted (20 μg/ml) and incubated with cells for 12 hours in serum-free conditions. 8R-tagged proteins were depleted by ~12% in NIH3t3- and ~3.5% in HUES7-incubations. This precisely mirrors flow cytometric data with 8R-proteins poorly transduced into HUES7 cells but at moderate levels in NIH3t3 cells (FIG. 2). P21-tagged proteins were significantly depleted in both cell types (~37% and ~25% in NIH3t3 and HUES7 cells, respectively; p<0.05) with HETD-proteins depleted from media to the highest levels and majority of protein removed (~72 and ~66% in NIH3t3 and HUES7 cells, respectively; p<0.01).

The time required to deplete half of the fluorescence (T½) was determined, with P21-mR-8R requiring only ~9.4 hours, in comparison to mR-8R which required –62 hours and untagged protein never achieving half-depletion even after 7 days (FIG. 16). These data are corroborative with the cytometric data proving a rapid and efficient enrichment of exogenous GET-protein/HETD-protein into cells. Therefore, it was demonstrated that within a relatively short incubation period (6 hours) that a significant protein concentration can be achieved within cells. In less than a day, the majority of extracellular protein has been effectively internalised using GET delivery. This system will be amenable to precise regulation of protein stoichiometry, while avoiding the stochastic transgene expression variation and silencing of integrating vectors used in gene-therapy approaches.

GET Enhances Cre-Mediated Genome Modification

It was determined that HETDs bind rapidly to cell membranes through HIS-GAGs and transduce efficiently into cells, but it was yet to be confirmed if the mode of uptake was through macropinocytosis as for PTDs. Also, what proportion of this protein escaped endosomes and may be considered successfully delivered was not assessed. Previous studies have the avoided issues associated with direct measurement of fluorescent-tagged proteins (such as being unable to distinguish membrane, vesicle or functional cytosolic/nuclear protein) by assaying for the successful nuclear activity of Cre recombinase {Gump, 2010 #2}. This system was used to measure Cre-mediated recombination of a loxP-STOP-loxP (LSL) enhanced green fluorescent protein (eGFP) reporter gene in live NIH3t3 mouse fibroblast cells (NIH3t3: LSL-eGFP cells) as an indicator of cellular uptake (FIG. 4a). This system is rigorous as activation of green fluorescence requires exogenous Cre protein to enter the cell, undergo nuclear-translocation and excise the LSL fragment of the transgene. This must occur in live cells and be non-toxic for the subsequent expression of eGFP. However, this process requires only one functional Cre recombinase molecule to be delivered to activate eGFP so does not allow the determination of the precise amount of cargo delivered. To overcome this issue Cre proteins were delivered at limiting dilutions for a short exposure time (1 hour) and the minimum dose required to activate green fluorescence after 48 hours (FIG. 4c) was determined.

Transduction of NIH3t3: LSL-eGFP cells with SIN Cre lentiviruses to overexpress Cre transgenically led to near complete (92±6%; p<0.001) activation of eGFP-expression in all cells confirming the utility of this system (FIG. 4b). The benefits of the fluorescence system and delivered fluorescent-versions of Cre-recombinase protein were retained by purifying proteins with mRFP1 cloned to the N-terminal of Cre cDNA. Treatment of NIH3t3: LSL-eGFP cells with mR-Cre (mRFP fused to Cre) resulted in recombination and eGFP activation (22.1±6.7%; p<0.05) at the highest doses (500 g/ml) (FIG. 4d). eGFP activation was inhibited at 4'C and negatively affected by serum concentration-dependently. mR-Cre-8R demonstrated that the 8R PTD enhanced functional delivery of Cre (~22-fold; p<0.01).

The GET-protein/HETD-protein, P21-mR-Cre-8R, required as little as one minute incubation with cells at a low dose (1 μg/ml) to elicit recombination (4.3±2.5%; p<0.05) confirming that binding and internalization is an efficient and rapid process. For a moderate dose (10 μg/ml) GET/HETD-transduction achieved a functional delivery ~15-fold (p<0.01) above PTD only levels and completely recombined all NIH3t3: LSL-eGFP cells (FIG. 4d,e). Importantly this activity was ~340-fold better than mR-Cre (p<0.001). Heparinase III, free-heparin and serum-free experiments were repeated using the Cre recombination system. It was confirmed that heparinase III pre-treatment reduced recombination to basal-levels and that media serum plays a role in replenishing cell membrane GAGs depleted by heparinase. Overall these data correlate well with the fluorescence delivery conclusions and show synergy between P21- and PTD-moieties to achieve significant increases in functional transduction of protein cargo.

GET Protein Enters Cells by Lipid Raft Macropinocytosis

Previously it has been shown that PTD-mediated internalization is via macropinocytosis rather than other endocytotic pathways {Wadia, 2004 #25}. It was next determined whether the cellular uptake of GET-proteins/HETD-proteins occurs through a specific endocytotic pathway employing the Cre assay system. Removal of cholesterol from the cell plasma membrane disrupts several lipid raft-mediated endocytotic pathways, including caveolae and macropinocytosis {Anderson, 1998 #29; Nichols, 2001 #30; Liu, 2002 #28}. NIH3t3: LSL-eGFP cells treated with methyl-p-cyclodextrin and nystatin were used to deplete or sequester cholesterol, respectively, then transduced HETD-tagged proteins. Both methyl-b-cyclodextrin (FIG. 17a) and nystatin (FIG. 17b) disruption of lipid rafts resulted in a dose-dependent inhibition of functional delivery. These data demonstrates that GET/HETD-mediated transduction specifically requires lipid raft-mediated endocytosis.

Macropinocytosis is a rapid, lipid raft-dependent and receptor-independent form of endocytosis which requires actin membrane protrusions that envelope into vesicles termed macropinosomes {Nichols, 2001 #30; Liu, 2002 #28; Conner, 2003 #22}. To confirm macropinocytosis was indeed the endocytotic mechanism of HETD-mediated transduction cells were pre-treated with macropinocytosis-inhibiting compounds (FIG. 11a,b). Amiloride is a specific inhibitor of the Na+/H+ exchange required for macropinocytosis {West, 1989 #31}. Cytochalasin D is an inhibitor of F-actin elongation which is required for macropinosome-linked membrane protrusions {Sampath, 1991 #32}. Amiloride and Cytochalasin D did not disrupt cell binding of HETD-proteins but resulted in a dose-dependent reduction of functional transduction into cells (FIGS. 17c and 17d, respectively). These data confirm that P21 enhances the macropinocytotic pathway used by PTD to internalize cargo molecules.

GET-Delivery Promotes General Macropinocytosis

The effects of GET-binding/HETD-binding on the induction of macropinocytosis was investigated. PTD-mediated transduction has previously been shown to promote the uptake of other proteins by an increase in the overall level of macropinocytosis {Wadia, 2004 #25}. Cells were incubated with a fluorescent fluid-phase macropinocytotic maker, FITC-labeled 70 kDa neutral dextran, in combination with GET/HETD protein, P21-mR-8R (FIG. 18). Other studies {Oliver, 1984 #24; Araki, 1996 #23; Wadia, 2004 #25} have demonstrated that neutral dextrans are taken up by amiloride-sensitive macropinocytosis. P21-mR-8R induced a significant dose dependant increase in fluid-phase dextran uptake over steady-state control levels. PTD-tagged versus GET/HETD-tagged activity to stimulate this macropinocytosis was compared. P21-mR-8R enhanced FITC-dextran uptake ~2.5-fold ($p<0.05$) over the stimulation achieved by the same concentration of mR-8R demonstrating that engagement with HS-GAG through P21 and its subsequent effect on PTD-mediated transduction stimulates macropinocytic uptake.

Significant Amounts of GET-Delivered Protein is Trapped in Endosomes which can be Efficiently Released with Chloroquine The majority of PTD-delivered molecules remain trapped in macropinosomes even after further incubation indicating that release from these vesicles is inefficient. If fine-tuned and graded amounts of delivery are to be controlled then it would be beneficial if the majority of internalized protein could be considered as functional. Cells were treated with chloroquine, an ion-transporting ATPase inhibitor that disrupts endosomes by preventing their acidification {Seglen, 1979 #33} (FIG. 17e). Similar doses have been demonstrated to significantly improve the functional delivery of PTD-delivered proteins {Wadia, 2004 #25}. Sub-cytotoxic doses of Chloroquine (100 μM) resulted in a marked increase (95.3±4.8-fold; $p<0.001$) in functional HETD-tagged/GET protein delivery at a sub-threshold dose (0.1 μg/ml) indicating that this is point in the pathway is still a major issue to resolve for GET/HETD medicinal application. Nevertheless the GET-delivery/HETD-delivery system was so efficient that with chloroquine treatment we achieved significant and measureable levels of recombination (4.8±2.9%; $p<0.05$) with short (1 hour) incubations of >10 μg/ml (FIG. 17f). Combination of GET/HETD-delivery efficiency with endosomal-escape technologies may therefore allow precise and temporally controlled amounts of cargo function in cells.

GET-Mediated Internalisation is Efficient after Cell Membrane Association

Even for incubations using low amounts of GET-protein functional quantities of protein activity were observed within cells. However, to categorically and stringently prove that most GET protein was indeed efficiently internalising a series of analyses was conducted using reporters that are responsive to their cellular or extracellular localisation. HALO (Halo$^{Tag}$) was used, which is a self-labelling protein derived from DhaA[29]. HALO rapidly forms a covalent attachment to synthetic chloroalkane-based ligands; with cell permeant and impermeant ligands available. Intra-versus extracellular labelling of HALO was confirmed using transgenic over-expression of untagged HALO (for intracellular) and LAMP2b-HALO which is presented on the external cell membrane (for extracellular) and labeling with cell permeant (HALO$^{TAG}$ Oregon Green) or impermeant (HALO$^{TAG}$ Alexafluor$^{488}$) ligands (FIG. 20). GET-HALO proteins were constructed and recombinantly expressed (FIG. 21a) and delivered them to cells testing the the internalisation by sensitivity to labelling with the cell impermeant ligand. One hour incubation demonstrated that GET-proteins remained mainly extracellularly localised and attached to the cell membrane (FIG. 21b). However, with further incubation (1 h exposure with 5 h further incubation: 1 h-5 h) GET-protein (P21-HALO-8R) is effectively internalised (remaining cell permeant ligand-sensitive but impermeant ligand-insensitive) (FIG. 21c). These experiments were repeated using the mNectarine (mNect) variant of RFP which is pH-sensitive and loses almost all fluorescence in environments <pH6[30] (FIG. 22). In agreement with HALO transduction, mNect remained mostly membrane localised after 1 h and its fluorescence sensitive to acidic pH media incubation (pH5.5) (FIG. 22 d). After further incubation post-delivery (1 h-5 h) GET-mNect fluorescence was no longer sensitive to extracellular pH (FIG. 22c); however interestingly the absolute fluorescence levels were significantly decreased when compared to GET-mR, presumably due to the internal pH change the protein is experiencing during endosomal acidification[1]. These data demonstrates that GET protein membranes association is rapid and transduction is efficient post-cell binding. It was hypothesised that membrane clearance of GET-protein could be a rate-limiting step in the delivery process and this was tested by undertaking multiple transductions (1 h) of GET-mR varying the time between transductions (FIG. 23a). Indeed re-transduction directly after the initial transduction decreases the effectiveness of the second transduction however as little as I h between new transductions is required to obtain a maximal efficiency of re-transduction (FIG. 23b).

GET-Delivery Promotes Survival by NEO-Conferred Resistance of Antibiotic Selection The GET/HETD system appeared to be able to deliver significant amounts of molecule several orders of magnitude better than untagged protein. Next it was sought to test if the system could deliver prolonged protein activity and a system was devised to attempt to provide resistance to cells under antibiotic selection (FIG. 5). This is believed to be a more reflective assay of the sustained delivery and function of GET-cargos/HETD-cargos that would be required for clinical translation. Unlike the Cre-based which requires a single enzyme to be delivered once into cells to be reported by eGFP as 'success', the NEO-based assay requires sustained delivery over several days and significant quantities to negate the activity of the antibiotic. G-418 sulfate (Geneticin), an aminoglycoside antibiotic, which blocks polypeptide synthesis by inhibiting chain elongation {Eustice, 1984 #69}.

To test this, both MEF and NIH3t3 cells were subjected to a selection protocol in which cells were plated and subjected to three consecutive days of transduction with a GET/HETD NEO-cargo, P21-mR-NEO-8R. Cells were then re-plated and simultaneously selected with G-418 and ongoing GET/HETD NEO transduction for an additional three days (FIG. 5a). After selection these cultures were assessed for cell numbers remaining, viability using trypan blue exclusion, and stained using calcein AM/ethidium homodimer-1 to label LIVE/DEAD cells, respectively. These were compared to cells processed under the same regime but transduced with a NEO-expressing lentivirus, SIN NEO, representing the conventional transgenic approach to confer G-418 resistance.

These data revealed a dose-dependent survival of selected cells with transduced P21-mR-NEO-8R (FIG. 5b). This survival was comparable to that conferred transgenically by SIN NEO integration (~3.6-fold better survival; p<0.05) when P21-mR-NEO-8R was delivered at high doses with lower G-418 doses (~3.3-fold better survival; p<0.05) (FIG. 5c-c). The highest-doses of G-418 could only be negated by SIN NEO transgenesis. Taken together, these experiments provide proof of principle that GET-delivered/HETD-delivered protein can provide sustained delivery of significant amounts of molecule and can promote the survival of mammalian cells under stringent antibiotic-selection.

GET-Delivery of NANOG Promotes Self-Renewal of Pluripotency

If this technology is to be adopted for clinical applications then it is important to demonstrate its use to alter cell-fate as well as control cell metabolism. A potentially important application of this technology would be in the driving of reprogramming, self-renewal and differentiation of stem cells. iPSC technology has been swiftly developed to allow genome non-integrating DNA {Yu, 2011 #91}, RNA {Warren, 2010 #4} and protein {Kim, 2009 #71; Zhou, 2009 #72} based technologies to supersede the original retroviral protocols {Takahashi, 2007 #82}. As PTD-delivery mediated reprogramming has already been demonstrated we sought to demonstrate that HETD-delivery was translatable to promote pluripotent cell fate {Kim, 2009 #71; Zhou, 2009 #72} (FIG. 6).

To test this hypothesis, CGR-8 mESCs were employed to determine if GET/HETD-mediated delivery can sustain their pluripotent self-renewing phenotype with the withdrawal of Leukemia inhibitory factor (LIF). GET/HETD NANOG-cargo were delivered in an assay {Dixon, 2010 #16} similar to that used to initially isolate the role Nanog in mESCs {Chambers, 2003 #70}. CGR-8 cells were plated onto gelatinized plastic and subjected to three consecutive days of transduction with a GET/HETD NANOG-cargo. P21-mR-NANOG-8R, passaged and an additional three passages (three days per passage) continuing daily transduction in conditions lacking LIF (FIG. 6a). These cultures were assessed at each passage for cell number and after the third LIF-deficient passage, were assessed for morphological change, alkaline phosphatase (AP) activity and by QPCR for pluripotency- and differentiation-associated gene expression (Oct4, Rex1 and Fgf3, respectively). These were compared to cells transduced with NANOG-expressing lentivirus, SIN NANOG, which we have previously shown to rescue the self-renewal of CGR-8 cells in the same assay {Dixon, 2010 #16}.

These data revealed that P21-mR-NANOG-8R rescued AP activity in significant numbers of CGR-8 even with relatively low doses (5-10 µg/ml) (FIG. 6b). AP activity in high-dose P21-mR-NANOG-8R samples was similar to that achieved by the SIN NANOG transgenic. Transgenics and high-dose P21-mR-NANOG-8R-transduced CGR-8 cells proliferated to a similar level in LIF-deficient cultures (~87.6-fold more; p<0.001) (FIG. 6c) and also retained Oct4 expression to a similar level (albeit lower than LIF-containing cultures) (both p<0.05) (FIG. 6d). As observed previously, rescued cells by both DNA and protein methods up-regulated Igf5 and down-regulated Rex1 expression, which indicates an ICM-to-epiblast transition phenotype {Dixon, 2010 #16}. These experiments provide a demonstration that GET/HETD-delivered protein can prevent differentiation and retain the pluripotent phenotype which may be later applied to iPSC technology.

GET-Delivery of MYOD Drives Myogenesis

To realize the promise of iPSC technology for regenerative medicine or disease modeling, it is imperative that the multi-lineage differentiation potential of pluripotent cells is harnessed {Robinton, 2012 #30}. Although progress has been made in directing the differentiation of these cells to various lineages by modulating the extracellular cytokine milieu, such protocols remain relatively inefficient. Given the high efficiency of functional PTD-mediated cargo delivery by P21-enhancement, it was reasoned that GET/HETD technology might also be utilized to redirect pluripotent cells toward differentiated cell-fates beyond that already described for transduction of transcription-factors {Do Kwon, 2005 #74; Hidema, 2012 #75; Liang, 2013 #73}.

For this the delivery of the efficacious MYOD myogenic factor {Bichsel, 2013 #92} was used to drive skeletal muscle specification (FIG. 7). To test this hypothesis, an in vitro differentiation protocol was devised in which HUES7 cells were plated onto gelatin and conventional media was withdrawn. Under these conditions, cells were then subjected to seven consecutive days of transduction with a GET/HETD MYOD-cargo, P21-mR-MYOD-8R, followed by an additional three days of culture in conditions with low concentrations of horse serum (FIG. 7a). These cultures were assessed for morphological change, immunostained for the myogenic marker MYOGENIN, assessed for myogenic-linked multinucleation by DAPI staining and by QPCR for myogenic gene expression (endogenous MYOD and ACTA1). These were compared to cells processed under the same regime but transduced with MYOD-expressing lentivirus, SIN MYOD.

These data revealed a high percentage of large multi-nucleated MYOGENIN-positive myotubes (62.1±8.9%; p<0.01) (FIG. 7b-f) which had elevated MYOD and ACTA1 expression (p<0.01 and <0.05, respectively) (FIG. 7c). This was comparable to the differentiation observed in the SIN MYOD transgenic when P21-mR-MYOD-8R was delivered at high doses. Taken together, these experiments provide proof of principle that GET/HETD-delivered protein can direct the fate of HUES7 cells to a terminally differentiated somatic cell type.

Discussion

By combining a protein-transduction domain (PTD) with a cell membrane binding peptide, such as a HS-GAG binding (HBD)-peptide, to improve cell membrane targeting, a technology has been developed that enables highly efficient delivery of functionally relevant proteins to direct a variety of cell behaviours, even in hard to transduce cell-types. It was demonstrated that the GET/HETD system can be harnessed to promote survival, self-renewal or direct the differentiation of pluripotent cells toward a desired lineage. This system is not technically complex, as for modified RNA systems {Warren, 2010 #4}, and offers several key advantages over established techniques to deliver the exogenous function of a gene or protein. Furthermore by obviating the stringent biological containment required for viral gene-therapy approaches, GET/HETD-driven protein transduction technology should make such approaches more accessible.

More fundamentally, because the technology is protein based, it completely eliminates the risk of genomic integration and insertional mutagenesis inherent to all DNA-based methodologies {Gump, 2007 #39}. Moreover if endosomal escape can be improved, our approach will allow protein stoichiometry to be tightly regulated within cultures. This will avoid stochastic variation in expression typical of integrating vectors, as well as the uncontrollable effects of viral silencing. GET/HETD technology may also be directly applied to reprogramming technologies. Given the stepwise character of the phenotypic changes observed during pluripotency induction {Chan, 2009 #63; Smith, 2009 #64} and for directed-differentiation protocols {Burridge, 2011 #81}, it seems likely that individual transcription factors play distinct, stage-specific roles. The unprecedented potential for temporal control over individual factor function afforded by GET/HETD technology should enable these variables to be tested to improve efficiency and kinetics of cell-fate control.

The transient and non-mutagenic character of protein-based transduction could also deliver important clinical benefits outside those investigated here. Indeed, the use of protein transduction to express cancer or pathogen antigens for immunotherapy {Rabinovich, 2009 #67} may benefit from the non-immunogenic properties of protein transduction.

The majority of delivered protein may be trapped in the inside of the endosome. The PTD field has focused on mechanistic aspects of TAT and other PTD interaction and escape from macropinocytomes with the goal of improving the release of cargo from vesicles {Heitz, 2009 #42}. The issue was approached from another angle with the aim to deliver proteins beyond that that may be achieved by PTDs and their avidity to the cell surface.

Previous studies delivering TAT-Cre suggested that the rate-limiting step for effective PTD-mediated delivery of a functional cargo is macropinosome escape, however this data suggests that even though this escape process will ultimately control whether PTDs are successfully used to treat disease {Sugita, 2007 #80}, that the PTD-transduction process itself is not the most efficient it could physiologically be. GET/HETD-mediated transduction described here improves present systems by up to three orders of magnitude for hard-to-transduce cells. Marrying vesicle escape with the GET/HETD system will be a significant development. As proof-of-concept this was demonstrated by the use of general endosomal disruptor, Chloroquine. By decreasing macropinocytome-integrity during GET/HETD-transduction functional delivery of proteins using pg/ml concentrations was shown (FIG. 17f).

The present understanding of PTD-mediated delivery consists of the hypothesis that a dense forest of GAGs provides the cell membrane with a ubiquitously negatively charge that PTDs bind to {Gump, 2007 #39}. Change in charge effect this binding but this is independent of the ability of PTDs to transduce cells or induce macropinocytotic uptake. GET/HETD has effectively created a more exaggerated version of this phenomenon with tagged-proteins more avidly binding cell membranes and promoting successful transduction mediated by a PTD. Alternative HBDs function in a similar manner to P21 with different efficacies and cell-type activities, depending on their source of isolation. Replacement of 8R has shown that other PTDs (TAT, 8K, 8RQ) can be employed in a successful GET/HETD (FIG. 11).

It is known that GAGs, such as HS-GAGs, have diverse biological functions and are widely involved in many physiological and pathological processes such as blood coagulation and inflammatory responses {Lortat-Jacob, 2002 #53; Varki, 2008 #52} via interactions with a variety of proteins including growth factors, cytokines and chemokines {Sasisekharan, 2006 #55; Gandhi, 2008 #54}. The interactions are dependent upon the disaccharide composition and patterns of GAGs, which play a significant role in regulating various biological processes. The heterogeneity of HS-GAGs is determined by the expression patterns of a variety of linked genes and multiple HS-GAGs-editing enzymes under different pathological conditions {Lindahl, 1998 #56; Nakato, 2002 #57; Sasisekharan, 2002 #60; Bengtsson, 2003 #59; Gesslbauer, 2007 #58}. Inflammatory processes and diseases such as mucopolysaccharidoses, osteoarthritis and myeloma cancer have been reported to correlate to the different disaccharide structures of GAGs. Therefore, evaluating the variations (i.e. presence and quantity) of GAGs has a great potential for diagnosis and prognosis of diseases.

The discovery that promoting GAG interaction significantly improves the efficiency of PTD-tagged biologically active, macromolecular cargo will open up new avenues for the treatment and experimental investigation of disease.

Experimental Procedures

Expression and Purification of Recombinant Proteins cDNA was obtained for mRFP1 (mR) as a kind gift from Prof. R. Y. Tsien (University of California, USA) {Campbell, 2002 #12}. 8R, TAT, 8K, 8RQ, P21, Cre, NANOG, MYOD and NEO cDNAs were synthesized de novo (Eurofins MWG Operon). cDNAs were cloned into the pGEX6-P1 expression vector (Novagen) to create in-frame fusions and expressed proteins in BL21 (DE21) pLysS *Escherichia coli* (Novagen). Exponentially growing LB cultures ($OD_{600}$=0.4) shaken at 220 rpm at 37° C. were induced using 1 mM IPTG for 24 hours at 25° C. Bacterial pellets were lysed and sonicated (7 amplitudes, 1 minute, 5 times) in 1×STE extraction buffer (50 mM Tris, pH 7.5, 150 mM NaCl, 1 mM EDTA containing 1 mM DTT, 0.2 mg/ml lysozyme, and 1× protease inhibitor cocktail).

Insoluble protein was retrieved using the Rapid GST inclusion body solubilisation and renaturation kit (AKR-110; Cell Biolabs, Inc., San Diego, Calif.). Recombinant proteins were purified by affinity chromatography using Glutathione-Sepharose resin (GE Healthcare). GST-tags were removed and eluted from resin by PreScission™ Protease cleavage (GE healthcare) in 1× cleavage buffer (50 mM Tris-HCl pH 7.0, 150 mM NaCl, 1 mM EDTA and 1 mM DTT). Protein concentration was determined using a BCA-based protein assay (BioRad) with absorbance measured at 595 nm using recombinant mR protein as a standard, Integrity and full-length protein expression was confirmed by SDS-PAGE. The fluorescence of recombinant proteins (excitation: 584 nm; emission: 607 nm) was determined with all preparations <10% intensity difference between samples (fluorescence/μg). Standards and samples were analysed using the TECAN infinite 200PRO multi-mode reader. Aliquots were stored at −80° C.

Cell Culture

NIH3T3 mouse fibroblast cells, [HEK293T human embryonic kidney cells, C2C12 mouse myoblast cells, iIMSC immortalised human mesenchymal stem cells (created as described {Okamoto, 2002 #8}) and MEF murine embryonic fibroblasts (harvested as described {Anderson, 2007 #9}) were maintained in DMEM with 10% (v/v) fetal calf serum (FCS; Sigma) media supplemented with 2 mM L-glutamine, 100 units/ml penicillin and 100 μg/ml streptomycin). CGR-8 mouse embryonic stem cells (mESCs) and EXT1-7-mESCs (a kind gift from Dr. D. E. Wells, University of Houston, USA; {Lin, 2000 #78}) were maintained in DMEM, 20% (v/v) FCS, 1000 units/ml leukaemia inhibitory factor (LIF), non-essential amino acids, 100 µM β-mecaptoethanol (Sigma) 2 mM L-glutamine, 100 units/ml penicillin and 100 µg/ml streptomycin). HL1 mouse cardiomyocyte cells were maintained as described {Claycomb, 1998 #7}. HUES7 human embryonic and IPS2 induced pluripotent stem cells were cultured as previously described {Dick, 2011 #10}. HUES7fib human fibroblasts derived from HUES7 cells were generated and cultured as previously described {Dick, 2011 #10}. All cells were cultured at 37° C. under 5% $CO_2$ Flow Cytometry and Microscopy For flow cytometry, cells were trypsinized (unless otherwise stated), fixed in 4% (w/v) PFA, resuspended in PBS (pH7.5) and analysed on a MoFlo™ DP (DAKO) Flow Cytometer using a 488 nm green laser. (50,000 cells; gated on live cells by forward/side scatter). Median fluorescence was used for statistical analyses with background from unlabelled/transduced cells subtracted and values taken as ratios to the experimental control. Data shown are three experiments of triplicate samples. For microscopy, cultures were rinsed twice with PBS and imaged with inverted fluorescence microscope (Nikon Eclipse TS100).

Fluorescence Delivery Assay

For testing multiple cell lines we plated $2=10^5$ cells/well (in 12-well plates) onto the surface relevant to the tested cell line, attached cells for 2 hours and transduced with recombinant proteins in cell-type specific growth media. After transduction cells were washed with PBS, trypsinized and fixed in 4% PFA for flow cytometry. For membrane localization, intracellular localisation or both we plated cells as above, but cultures pre-incubated in serum-free media for 1 hour before transduction. Membrane localization to assess cell interaction was achieved by a short transduction of 1 hour in serum-free media. Intracellular localization to assess transduction efficiency was achieved by a short transduction of 1 hour followed by 5 hour incubation in serum-free media only. Cell association (membrane and intracellular levels) were assessed by transducing cells for 6 hours in serum-free medium. For flow cytometry cells were trypsinized, washed and fixed in 4% PFA and for microscopy cells were imaged live after washing in PBS. For trypsin depletion of cell-surface proteins, cells were treated with trypsin/EDTA (Invitrogen) or EDTA-based cell dissociation solution (CDS) (Sigma) for 15 minutes at 37° C., followed by washes with PBS and 1× soybean trypsin inhibitor (10 mg/ml in PBS; Sigma). Cells were then treated with proteins for 1 hour at 37° C. in serum-free medium. For detergent depletion of cell membranes, cells were treated with PBS (pH7.5) containing 0.1% (v/v) Triton-X100 (Tx100) for 10 minutes at 37° C., followed by washes with PBS. Cells were then treated with proteins for 1 hour at 37° C. in serum-free medium. For GAG-treatment cells were pre-treated with GAGs in DMEM without serum before transduction and were included in the transduction media. This included heparin and chondroitin sulphate A, B and C (0-50 µg/ml).

Total Delivered Protein Analyses $5 \times 10^6$ NIH3t3 cells were plated (in T25 flasks), pre-incubated cells in serum-free DMEM for 1 hour, and transduced them with mR-8R or P21-mR-8R (0-200 µg/ml; 1 ml volume) in serum-free DMEM for 6 hours. NIH3t3 cells transduced with SIN-mR lentiviruses were used as a control for the levels achieved by transgenic systems {Dixon, 2011 #15; Dick, 2011 #10}. Cells were harvested by trypsinization, fixed in 4% PFA for flow cytometry or washed several times in cold PBS with soluble protein extracted in cold HKM buffer (20 mM HEPES, pH 7.5, 5 mM KCl, 0.5 mM $MgCl_2$ and 0.5 mM DTT with 1× complete EDTA-free protease inhibitor cocktail) for fluorometry {Medina, 2000 #14}. Extracts were sonicated, centrifuged and NaCl added to yield a final concentration of 100 mM prior to analyses. Fluorometry was used to compare soluble extracts with purified mRFP protein diluted in HKM buffer with 100 mM NaCl as standards. Flow cytometry was used to assess total delivered protein in intact cells.

Media Depletion Assessment $2 \times 10^6$ NIH13t3 cells or HUES7 HESCs were plated (in 6-well plates), pre-incubated cells in serum-free DMEM for 1 hour, and transduced with recombinant proteins (20 µg/ml; 1 ml volume) in serum-free DMEM for 12 hours. Media was harvested and fluorometry was used to compare the remaining fluorescence in media verses that before cell-incubation. Fluorescence of media pre-incubation was assigned as 100% fluorescence units and background of serum-free media subtracted.

Heparin-Binding Assay, Heparinase Treatment and Depletion of P21-Binding Molecules from Serum For Heparin binding activity we incubated 1 ml of recombinant proteins (20 µg/ml) in DMEM with 50 µl of PBS-washed Heparin-sepharose beads (Sigma) for 1 hour at 37° C. shaking at 100 rpm. Media pre- and post-incubation was compared by fluorometry. For Heparinase treatment, we plated NIH3t3 cells at $2 \times 10^5$/well (in 12-well plates) and were pre-incubated in serum-free media for 1 hour with Heparinase III (0-1 U/ml) or Heparin (0-50 µg/ml). Cells were then washed and transduced with mR or P21-mR-8R (20 µg/ml in serum-free media or media with different FCS concentrations) containing Heparinase III or Heparin for 12 hours. FCS was depleted of P21-binding material by affinity chromatography. This was achieved by incubating 50 ml FCS with 2 ml Glutathione-Sepharose resin (GE Healthcare) pre-absorbed with GST-P21 protein expressed in *Escherichia coli*.

Macropinocytosis Assessment

To measure the effects of protein transduction on general macropinocytosis, cells were incubated with 100 µg/ml FITC-70 kDa neutral dextran (Sigma), along with different recombinant proteins (0-10 µg/ml) for 1 hour at 4° C. or 37° C. Cells were trypsinized and washed in PBS before analyses by flow cytometry.

Cre Recombination Assay

To measure Cre Recombinase activity the NIH3t3: LSL-eGFP cell line was created using the pZ/EG plasmid transfection and G-418 selection {Novak, 2000 #6}. To confirm Cre activity efficiently led to recombination and eGFP activation cells were transduced with SIN-Cre lentiviruses (as described in Dixon et al. 2011) and >95% of cells were confirmed eGFP-positive 48 hours post-transduction. $2 \times 10^5$ cells/well were plated (in 12-well plates), pre-incubated them in DMEM without serum for 1 hour and treated with Cre proteins (0-500 µg/ml) in DMEM without serum. After the Cre incubation cells were trypsinized, replated into complete media and incubated for 2 days. Cells were pre-treated with drugs for the stated time-period in DMEM without serum, were included in Cre-transduction medium and were added after replating. Pre-treatments included: heparin (0-50 µg/ml), chondroitin sulphate A, B and C (0-50 µg/ml), chloroquine (0-100 µM), cytochalasin-D (0-10 µM), amiloride (0-5 mM), methyl-β-cyclodextrin (0-5 mM), and nystatin (0-50 µg/ml). After incubations cell were trypsinized, washed, fixed in 4% PFA and % recombined cells was determined by flow cytometry. For mR-Cre-8R and P21-mR-Cre-8R comparisons concentrations of 100

μg/ml and 10 μg/ml were used, respectively and data was expressed as % maximum recombination (i.e. the % relative to the maximum recombination achieved at the stared dose of Cre).

NEO Antibiotic-Resistance Assay

To measure NEO activity the survival and proliferation of NIH3t3 and MEF in the presence of G-418 antibiotic selection was assessed. Cell number, viability and live/dead ratios were measured. To confirm NEO activity efficiently leads to survival and proliferation under G-418 selection of NIH3t3 and MEF cells, the cells were transduced with SIN-NEO lentiviruses (as described in Dixon et al. 2009) and confirmed that NEO transduction prevents cell death and retains viability under stringent G-418 selection. This was used in comparisons with NEO protein transductions. We plated $3 \times 10^5$ MEF cells/well or $1 \times 10^5$ NIH3t3 cells/well (in 12-well plates) and cultured them in DMEM with 10% FCS containing P21-mR-NEO-8R (0-100 μg/ml) for 3 days. Cells were replated at $3 \times 10^5$ cells/well for MEF cells or $1 \times 10^5$ cells/well for NI-13t3 cells. Cells were cultured in DMEM with 10% FCS containing P21-mR-NEO-8R (0-100 μg/ml) and G-418 sulphate (0-300 μg/ml) for a further 3 days feeding daily to kill non-resistant cells. Cells were counted, assessed for viability using trypan blue exclusion or assayed using the LIVE/DEAD staining {Bayoussef, 2012 #13}.

NANOG Self-Renewal Assay

To measure NANOG activity we used LIF-withdrawal from CGR-8 mESCs and measured alkaline phosphatase (AP) activity, cell numbers and assessed gene expression changes by quantitative-PCR (QPCR). To confirm NANOG activity efficiently leads to rescue of self-renewal without LIF we transduced cells with SIN-NANOG lentiviruses (as described in Dixon et al. 2009) and confirmed that CGR-8 self-renewal was efficiently rescued and this was used in comparisons with NANOG protein transductions. $2 \times 10^5$ cells/well were plated (in 6-well plates), pre-incubated them in growth media with LIF for one passage/3 days containing P21-mR-NANOG-8R (0-50 μg/ml) feeding with fresh media daily. Cells were replated at $2 \times 10^5$ cells/well (in 6-well plates) in growth media without LIF (and with LIF as controls) containing P21-mR-NANOG-8R (0-50 μg/ml). Cells were fed daily with this media and every 3 days were counted and passaged replating one-tenth of the cells until 3 passages. After the third passage post-LIF withdrawal cells were stained for AP activity (86R-1 kit; based on Naphthol AS-BI and fast red violet LB; Sigma)) or processed for QPCR analyses. Relative expression levels ($\Delta\Delta$CT) were determined QPCR using TaqMan™ Gene Expression Master Mix and specific TaqMan™ Gene Expression Assays (Applied Biosystems).

MYOD Myogenesis Assay

To measure MYOD activity we used differentiation of HUES7 HESCs and assessed cell morphology, cell multinucleation, gene expression changes by quantitative-PCR (QPCR) and MYOGENIN protein expression. To confirm MYOD activity efficiently leads to myogenic differentiation of HESCs we transduced cells with SIN-MYOD lentiviruses (as described in Dixon et al. 2009) and confirmed that MYOD directs multinucleated myotube differentiation which was used in comparisons with MYOD protein transductions. $1 \times 10^6$ cells/well were plated into 0.1% gelatin-coated plates (in 6-well plates) and cultured them in DMEM with 10% FCS for 1 week with one passage using trypsin. Cells were replated at $1 \times 10^6$ cells/well into 0.1% gelatin-coated plates and cultured in DMEM with 10% FCS containing P21-mR-MYOD-8R (0-50 μg/ml). Cells were fed daily with this media for 7 days. The culture media was then switched to DMEM with 2% horse serum (HS) and cultures maintained for a further 7 days. Cells were then processed for QPCR or fixed in 4% PFA and immunostained {Bayoussef, 2012 #13}. Nuclei were labelled using DAPI as previously described (Dixon et al. 2009). The percentage of MYOGENIN-positive nuclei/total nuclei was quantified, with a minimum of 200 nuclei counted per condition. Relative expression levels (AACT) were determined QPCR using TaqMan® Gene Expression Master Mix and specific TaqMan™ Gene Expression Assays (Applied Biosystems).

Antibody, Nucleic Acid and Nanoparticle Delivery Biotinylated-Goat anti-Rabbit and FITC-Rabbit anti-mouse antibodies (Sigma), pSIN-GFP (Dixon et al. 2014), modified nucleotide RNA (modRNA) for GFP (Miltenyi Biotech) and FAM-labelled siRNA against GAPDH (Sigma), and nanomag-D (250 nm) (MircoMod) were complexed with GET-proteins or -peptides and added to cells. For antibodies complexes were allowed to form in growth media for 20 mins before cell addition. For nucleic acids a 2:1 peptide: nucleic acid charge ratio was used for complexation. GET- or LIPO2000 (lipofectamine 2000; Invitrogen) transfection used 10 μg or 1 μg nucleic acid per transfection of 100,000 hMSCs in 12 well plates. GET-peptide substituted LIPO2000 following the exact manufacturer's instructions. For MNPs, a final concentration of 25 M peptide was used in an EDAC/NHS reaction using 2 mg MNPs according to manufacturer's instructions. Prussian blue was carried out using potassium ferrocyanide (2.5% w/v) in 2.5% w/v HCl.

Statistical Analysis

Statistical comparisons were carried out using the GraphPad Prism software package. Comparisons were made using Tukey-Kramer analysis of variance (ANOVA). Results were considered significant if $p<0.05$.

Example Sequences
Example HS-GAG Binding Sequences
P21 amino acid sequence

```
P21 amino acid sequence
                                              (SEQ ID NO. 1)
KRKKKGKGLGKKRDPCLRKYK P21 nucleotide sequence (with a methione/ATG):
                                              (SEQ ID NO: 2)
aagcgcaagaagagggcaaaggcctgggcaagaagcgcgatccgtgcct
gcgcaagtataag PDGF (194-211) amino acid sequence:
                                              (SEQ ID NO. 3)
G R P R E S G K K R K R K R L K P T PDGF (194-211) nucleotide sequence:
                                              (SEQ ID NO: 4)
ggccgcccgcgcgaaagcggcaaaaaacgcaaacgcaaacgcctgaaacc
gacc FGF7B amino acid sequence:
                                              (SEQ ID NO. 5)
T Y A S A K W T H N G G E M F V A L N Q.

FGF7B nucleotide sequence:
                                              (SEQ ID NO: 6)
Acctatgcgagcgcgaaatggacccataacggcggcgaaatgtttgtggc
gctgaaccag FGF2 HBD B(247-262) amino acid sequence:
                                              (SEQ ID NO. 7)
T Y R S R K Y T S W Y V A L K R.

FGF2 HBD B(247-262) nucleotide sequence:
                                              (SEQ ID NO: 8)
acctatcgcagccgcaaatataccagctggtatgtggcgctgaaacgc
```

Nucleotides Encoding 8R Protein Transduction Domain Sequence:

(SEQ ID NO: 9)
CGA AGA CGC AGG AGA CGT CGA AGG

Example Delivery Molecule Nucleotide Sequence (P21-Cargo-8R):

(SEQ ID NO: 10)
aagcgcaagaagaagggcaaaggcctgggcaagaagcgcgatccgtgcct
gcgcaagtataagNcgaagacgcaggagacgtcgaagg N=cargo nucleic acid sequence of various length (i.e. the number of nucleotide residues may vary), or another molecular entity.

Two versions of each of the nanobody variants of the ScFv antibodies were made; one with identical sequence to the ScFv vHH domain (Frame domain1-CDR1-Frame domain 2-CDR2-Frame domain 3-CDR3-IgA Hinge domain/Frame domain 4) and one in which the CDR1, 2 and 3 domains were grafted into a generic vHH domain sequence. Both versions have comparable activity and the grafting version was created to prove that simply grafting the CDR domains onto a generic antibody also works.

Below are the sequences of the HS4C3, and AO4B08 ScFv vHH and grafted vHH:

HS4C3 ScFv vHH
(SEQ ID NO: 11)
EVQLVESGGGLVQPRGSLRLSCAASGFTVSSNEMSWIRQAPGKGLEWVSSISGGSTYYADSRKGRFTISRDNSKNTLYLQMNNLRAEGTAAYYCGRRLKDPSTPPTPSPSTPPTPSPS

CDR1
GFTVSSNE

CDR2
ISGGST

CDR3
GRRLKD

H54C3 ScFv vHH nucleotide sequence
(SEQ ID NO: 12)
gaagtgcagctggtggaaagcggcggcggcctggtgcagccgcgcggcag
cctgcgcctgagctgcgcggcgagcggctttaccgtgagcagcaacgaaa
tgagctggattcgccaggcgccgggcaaaggcctggaatgggtgagcagc
attagcggcggcagcacctattatgcggatagccgcaaaggccgctttac
cattagccgcgataacagcaaaaacaccctgtatctgcagatgaacaacc
tgcgcgcggaaggcaccgcggcgtattattgcggccgccgcctgaaagat
ccgagcaccccgccgaccccgagcccgagcaccccgccgaccccgagccc
gagc H54C3 grafted vHH
(SEQ ID NO: 13)
QVQLVESGGGSVQAGGSLRLSCTASGFTVSSNELGWFRQAPGQERWAVAAISGGSTYYADSVKGRFTISRDNAKNTVTLQMNNLKPEDTAIYYCGRRLKDWGQGTQVTVSSPSTPPTPSPSTPPTPSPS

CDR1
GFTVSSNE

CDR2
ISGGST

CDR3
GRRLKD

H54C3 grafted vHH nucleotide
(SEQ ID NO: 14)
caggtgcagctggtggaaagcggcggcggcagcgtgcaggcgggcggcag
cctgcgcctgagctgcaccgcgagcggctttaccgtgagcagcaacgaac
tgggctggtttcgccaggcgccgggccaggaacgctgggcggtggcggcg
attagcggcggcagcacctattatgcggatagcgtgaaaggccgctttac
cattagccgcgataacgcgaaaaacaccgtgaccctgcagatgaacaacc
tgaaaccggaagataccgcgatttattattgcggccgccgcctgaaagat
tggggccagggcacccaggtgaccgtgagcagcccgagcaccccgccgac
cccgagcccgagcaccccgccgaccccgagcccgagc A04B08 ScFv vHH
(SEQ ID NO: 15)
EDQLVESGGGLVQPGGSLRPSCAASGFAFSSYALHWVRRAPGKGLEWVSAIGTGGDTYYADSVMGRFTISRDNAKKSLYLHMNSLIAEDMAVYYCSLRMNGWRAHQPSTPPTPSPSTPPTPSPS

CDR1
(SEQ ID NO: 22)
GFAFSSYA

CDR2
(SEQ ID NO: 24)
IGTGGDT

CDR3
(SEQ ID NO: 26)
SLRMNGWRAHQ

A04B08 ScFv vHH nucleotide sequence
(SEQ ID NO: 16)
gaagatcagctggtggaaagcggcggcggcctggtgcagccgggcggcag
cctgcgcccgagctgcgcggcgagcggctttgcgtttagcagctatgcgc
tgcattgggtgcgccgcgcgccgggcaaaggcctggaatgggtgagcgcg
attggcaccggcggcgataccatatgcggatagcgtgatgggccgctt
taccattagccgcgataacgcgaaaaaaagcctgtatctgcatatgaaca
gcctgattgcggaagatatggcggtgtattattgcagcctgcgcatgaac
ggctggcgcgcgcatcagccgagcaccccgccgaccccgagcccgagcac
cccgccgaccccgagcccgagc A04B08 grafted vHH
(SEQ ID NO: 17)
QVQLVESGGGSVQAGGSLRLSCTASGFAFSSYALGWFRQAPGQERWAVAAIGTGGDTYYADSVKGRFTISRDNAKNTVTLQMNNLKPEDTAIYYCSLRMNGWRAHQWGQGTQVTVSSPSTPPTPSPSTPPTPSPS

CDR1
(SEQ ID NO: 22)
GFAFSSYA

CDR2
(SEQ ID NO: 24)
IGTGGDT

-continued

CDR3
(SEQ ID NO: 26)
SLRMNGWRAHQ

A04B08 grafted vHH nucleotide sequence
(SEQ ID NO: 18)
caggtgcagctggtggaaagcggcggcggcagcgtgcaggcgggcggcag cctgcgcctgagctgcaccgcgagcggctttgcgtttagcagctatgcgc tgggctggtttcgccaggcgccgggccaggaacgctgggcggtggcggcg attggcaccggcggcgatacctattatgcggatagcgtgaaaggccgctt taccattagccgcgataacgcgaaaaacaccgtgaccctgcagatgaaca acctgaaaccggaagataccgcgatttattattgcagcctgcgcatgaac ggctggcgcgcgcatcagtggggccagggcacccaggtgaccgtgagcag cccgagcacccogccgacccogagcccgagcacccogccgaccccgagcc cgagc

REFERENCES

1. Gump J M & Dowdy S F (2007) TAT transduction: the molecular mechanism and therapeutic prospects. *Trends in molecular medicine* 13(10):443-448.
2. El-Andaloussi 5, Holm T, & Langel U (2005) Cell-penetrating peptides: Mechanisms and applications. *Curr Pharm Design* 11(28):3597-3611.
3. Goun E A, Pillow T H, Jones L R, Rothbard J B, & Wender P A (2006) Molecular transporters: Synthesis of oligoguanidinium transporters and their application to drug delivery and real-time imaging. *Chembiochem* 7(10):1497-1515.
4. Meade B R & Dowdy S F (2007) Exogenous siRNA delivery using peptide transduction domains/cell penetrating peptides. *Adv Drug Deliver Rev* 59(2-3):134-140.
5. Fischer R, Fotin-Mleczek M, Hufnagel H, & Brock R (2005) Break on through to the other side—Biophysics and cell biology shed light on cell-penetrating peptides. *Chembiochem* 6(12):2126-2142.
6. Nakase I, Takeuchi T, Tanaka G, & Futaki S (2008) Methodological and cellular aspects that govern the internalization mechanisms of arginine-rich cell-penetrating peptides. *Adv Drug Deliver Rev* 60(4-5):598-607.
7. Heitz F, Morris M C, & Divita G (2009) Twenty years of cell-penetrating peptides: from molecular mechanisms to therapeutics. *Brit J Pharmacol* 157(2):195-206.
8. Gump J M, June R K, & Dowdy S F (2010) Revised Role of Glycosaminoglycans in TAT Protein Transduction Domain-mediated Cellular Transduction. *J Biol Chem* 285(2):1500-1507.
9. Norbury C C, Hewlett L J, Prescott A R, Shastri N, & Watts C (1995) Class I MHC presentation of exogenous soluble antigen via macropinocytosis in bone marrow macrophages. *Immunity* 3(6):783-791.
10. Meier 0, et al. (2002) Adenovirus triggers macropinocytosis and endosomal leakage together with its clathrin-mediated uptake. *J Cell Biol* 158(6):1119-1131.
11. Conner S D & Schmid S L (2003) Regulated portals of entry into the cell. *Nature* 422(6927):37-44.
12. Wadia J S, Stan R V, & Dowdy S F (2004) Transducible TAT-HA fusogenic peptide enhances escape of TAT-fusion proteins after lipid raft macropinocytosis. *Nat Med* 10(3):310-315.
13. Skehel J J, Cross K, Steinhauer D, & Wiley D C (2001) Influenza fusion peptides. *Biochem Soc T* 29:623-626.
14. Han X, Bushweller J H, Cafiso D S, & Tamm L K (2001) Membrane structure and fusion-triggering conformational change of the fusion domain from influenza hemagglutinin. *Nat Struct Biol* 8(8):715-720.
15. Sakuma T, Higashiyama S, Hosoe S, Hayashi S, & Taniguchi N (1997) CD9 antigen interacts with heparin-binding EGF-like growth factor through its heparin-binding domain. *Journal of biochemistry* 122(2):474-480.
16. Higashiyama S, Abraham J A, & Klagsbrun M (1993) Heparin-Binding Egf-Like Growth-Factor Stimulation of Smooth-Muscle Cell-Migration—Dependence on Interactions with Cell-Surface Heparan-Sulfate. *J Cell Biol* 122(4):933-940.
17. Thompson S A, et al. (1994) Characterization of Sequences within Heparin-Binding Egf-Like Growth-Factor That Mediate Interaction with Heparin. *J Biol Chem* 269(4):2541-2549.
18. Kaplan I M, Wadia J S, & Dowdy S F (2005) Cationic TAT peptide transduction domain enters cells by macropinocytosis (vol 102, pg 247, 2005). *J Control Release* 107(3):571-572.
19. Lawrence R, Lu H, Rosenberg R D, Esko J D, & Zhang L J (2008) Disaccharide structure code for the easy representation of constituent oligosaccharides from glycosaminoglycans. *Nat Methods* 5(4):291-292.
20. Lin X, et al. (2000) Disruption of gastrulation and heparan sulfate biosynthesis in EXT1-deficient mice. *Dev Biol* 224(2):299-311.
21. Dick E, Matsa E, Young L E, Darling D, & Denning C (2011) Faster generation of hiPSCs by coupling high-titer lentivirus and column-based positive selection. *Not Protoc* 6(6):701-714.
22. Anderson R G W (1998) The caveolae membrane system. *Annu Rev Biochem* 67:199-225.
23. Nichols B J & Lippincott-Schwartz J (2001) Endocytosis without clathrin coats.
*Trends Cell Biol* 11(10):406-412.
24. Liu N Q et al. (2002) Human immunodeficiency virus type 1 enters brain microvascular endothelia by macropinocytosis dependent on lipid rafts and the mitogen-activated protein kinase signaling pathway. *J Virol* 76(13): 6689-6700.
25. West M A, Bretscher M S, & Watts C (1989) Distinct Endocytotic Pathways in Epidermal Growth Factor-Stimulated Human Carcinoma A431 Cells. *J Cell Biol* 109(6):2731-2739.
26. Sampath P & Pollard T D (1991) Effects of Cytochalasin, Phalloidin, and Ph on the Elongation of Actin-Filaments. *Biochemistry-Us* 30(7):1973-1980.
27. Oliver J M, Berlin R D, & Davis B H (1984) Use of Horseradish-Peroxidase and Fluorescent Dextrans to Study Fluid Pinocytosis in Leukocytes. *Method Enzymol* 108:336-347.
28. Araki N, Johnson M T, & Swanson J A (1996) A role for phosphoinositide 3-kinase in the completion of macropinocytosis and phagocytosis by macrophages. *J Cell Biol* 135(5):1249-1260.
29. Seglen P O, Grinde B, & Solheim A E (1979) Inhibition of the Lysosomal Pathway of Protein-Degradation in Isolated Rat Hepatocytes by Ammonia, Methylamine, Chloroquine and Leupeptin. *Eur J Biochem* 95(2):215-225.
30. Eustice D C & Wilhelm J M (1984) Mechanisms of Action of Aminoglycoside Antibiotics in Eukaryotic Protein-Synthesis. *Antimicrob Agents Ch* 26(1):53-60.

31. Yu J Y, Chau K F, Vodyanik M A, Jiang J L, & Jiang Y (2011) Efficient Feeder-Free Episomal Reprogramming with Small Molecules. *Plos One* 6(3).
32. Warren L, et al. (2010) Highly Efficient Reprogramming to Pluripotency and Directed Differentiation of Human Cells with Synthetic Modified mRNA. *Cell Stem Cell* 7(5):618-630.
33. Kim D, et al. (2009) Generation of human induced pluripotent stem cells by direct delivery of reprogramming proteins. *Cell Stem Cell* 4(6):472-476.
34. Zhou H Y, et al. (2009) Generation of Induced Pluripotent Stem Cells Using Recombinant Proteins (vol 4, pg 381, 2009). *Cell Stem Cell* 4(6):581-581.
35. Takahashi K, et al. (2007) Induction of pluripotent stem cells from adult human fibroblasts by defined factors. *Cell* 131(5):861-872.
36. Dixon J E, et al. (2010) Axolotl Nanog activity in mouse embryonic stem cells demonstrates that ground state pluripotency is conserved from urodele amphibians to mammals. *Development* 137(18):2973-2980.
37. Chambers I, et al. (2003) Functional expression cloning of Nanog, a pluripotency sustaining factor in embryonic stem cells. *Cell* 113(5):643-655.
38. Robinton D A & Daley G Q (2012) The promise of induced pluripotent stem cells in research and therapy. *Nature* 481(7381):295-305.
39. Do Kwon Y, et al. (2005) Cellular manipulation of human embryonic stem cells by TAT-PDX1 protein transduction. *Mol Ther* 12(1):28-32.
40. Hidema S, Tonomura Y, Date S, & Nishimori K (2012) Effects of protein transduction with intact myogenic transcription factors tagged with HIV-1 Tat-PTD (T-PTD) on myogenic differentiation of mouse primary cells. *J Biosci Bioeng* 113(1):5-11.
41. Liang Q L, Mo Z Y, Li X F, Wang X X, & Li R M (2013) Pdx1 protein induces human embryonic stem cells into the pancreatic endocrine lineage. *Cell Biol Int* 37(1):2-10.
42. Bichsel C, et al. (2013) Direct Reprogramming of Fibroblasts to Myocytes via Bacterial Injection of MyoD Protein. *Cell Reprogram* 15(2):117-125.
43. Chan E M, et al. (2009) Live cell imaging distinguishes bona fide human P S cells from partially reprogrammed cells. *Nat Biotechnol* 27(11):1033-U1100.
44. Smith K P, Luong M X, & Stein G S (2009) Pluripotency: Toward a Gold Standard for Human E S and iPS Cells. *J Cell Physiol* 220(1):21-29.
45. Burridge P W, et al. (2011) A Universal System for Highly Efficient Cardiac Differentiation of Human Induced Pluripotent Stem Cells That Eliminates Interline Variability. *Plos One* 6(4).
46. Campbell R E, et al. (2002) A monomeric red fluorescent protein. *Proceedings of the National Academy of Sciences of the United States of America* 99(12):7877-7882.
47. Okamoto T, et al. (2002) Clonal heterogeneity in differentiation potential of immortalized human mesenchymal stem cells. *Biochem Bioph Res Co* 295(2):354-361.
48. Anderson D, et al. (2007) Transgenic enrichment of cardiomyocytes from human embryonic stem cells. *Mol Ther* 15(11):2027-2036.
49. Claycomb W C, et al. (1998) HL-1 cells: A cardiac muscle cell line that contracts and retains phenotypic characteristics of the adult cardiomyocyte. *Proceedings of the National Academy of Sciences of the United States of America* 95(6):2979-2984.
50. Dixon J E, Dick E, Rajamohan D, Shakesheff K M, & Denning C (2011) Directed differentiation of human embryonic stem cells to interrogate the cardiac gene regulatory network. *Mol Ther* 19(9):1695-1703.
51. Medina D, Moskowitz N, Khan S, Christopher S, & Germino J (2000) Rapid purification of protein complexes from mammalian cells. *Nucleic Acids Res* 28(12).
52. Novak A, Guo C Y, Yang W Y, Nagy A, & Lobe C G (2000) Z/E G, a double reporter mouse line that expresses enhanced green fluorescent protein upon Cre-mediated excision. *Genesis* 28(3-4):147-155.
53. Bayoussef Z, Dixon J E, Stolnik S, & Shakesheff K M (2012) Aggregation promotes cell viability, proliferation, and differentiation in an in vitro model of injection cell therapy. *J Tissue Eng Regen M* 6(10):e61-e73.

Improving the Efficiency of Iron Oxide Nanoparticle Uptake Using Cell Penetrating Peptides Background Superparamagnetic Iron Oxide nanoparticles (SPIONS) are small highly magnetised particles consisting of an iron oxide core and surface coating. SPIONS have been clinically approved for use in MRI contrast agents[1], and are currently being researched for use in targeted drug delivery[2], hyperthermia treatment and cell labelling[3]. SPIONS have been approved for uses in MRI contrast agents and commercially available products include Lumiren, Resivist and Feridex.[1]

Applications of SPIONS require an adequate concentration being internalised into cells and without the required targeting of nanoparticles it can lead to an inefficient outcome. The efficiency of cell internalisation can depend on the size, coating and additional ligands to name a few[4]. Literature shows that without the attachment of internalisation agents researchers are achieving a range of 15-30 μg of iron per cell[5,6]. The functional groups on nanoparticle coatings can be exploited to target increase cell internalisation by attaching monoclonal antibodies, cell penetrating peptides and small molecules as internalisation agents.[7]

A currently researched cell penetrating peptide is Arg-Gly-Asp (RGD). RGD was designed to target the avβ3 intergrin[8]. The intergrin can be found predominantly on cancer cells, so can also be used as a targeting peptide. Research found that the RGD peptide increased nanoparticle uptake by 50%.[9]

The following study focuses on a cell penetrating peptide of the invention herein, in particular P218R. The peptide has two domains, P21 binds to the heparan sulphate (HS) on the cell membrane and the 8R aids in the transduction. The aim of the study was to identify the efficiency of the P218R and to investigate its mechanism.

Materials and Methods

Nanoparticle Labelling

A 31 mM EDAC with 0.1 M NIS dissolved in 0.5M MES buffer was added to Nanomag-D (250 nm) particles in a 1:5 ratio respectively and mixed for 1 hour. The particles are then washed in a 0.1M MES buffer and 0.2 μg/μl of the required labelling agent dissolved in the same buffer was added to give a 1:1 ratio of labelling solution and nanoparticles, an aliquot of the labelling solution was kept for testing labelling efficiency. The solution is then continuously mixed at room temperature for 3 hours. Once the particles are labelled a 25 mM glycine solution is added to the particles then further incubated for 30 minutes. An aliquot of the labelling solution is kept for comparison with the earlier aliquot and the particles washed in 0.1% BSA in PBS. Particles are finally diluted in 0.1% BSA in PBS to give a 1 mg/ml solution. Both aliquots of labelling solution and some of the labelled nanoparticles were assessed for fluorescence.

Cell Culture

NIH 3t3 fibroblast cells were cultured in Dulbecco's modified Eagle's media (DMEM; Gibeco), supplemented with 10% (v/v) Fetal Calf Serum (FCS, Sigma), 2 mM L-glutamine and (PS) at 37° C. and 5% CO2. The cells were then cultured until confluent.

Cell Labelling

Confluent cells were split into 12 well plates at 200,000 cells/well and incubated for 24 hours at 37° C. After 24 hours 50 µg of Nanomag-D iron oxide nanoparticles (250 nm) and either 0, 0.01, 0.05, 0.1, 0.5, 2, 1, 5 and 10 µM of cell penetrating peptide were added to the cells with either 10% FCS DMEM or serum free DMEM media and left for 24 hours for iron nanoparticles to be internalised. After incubation cells were washed in PBS to remove excess nanoparticles then harvested for qualitative Prussian blue staining, quantitative colorimetric iron assay or fluorescence activated flow cytometry.

Prussian Blue Staining

Cells were labelled then fixed in 4% (w/v) PFA for 15-20 minutes at 4° C. A staining solution of 2.5% potassium ferrocyanide in 2.5% HCL was added to cells and incubated for an hour at room temperature. If nanoparticles were present a blue stain appeared which is proportional to the concentration of iron.

Quantitative Colorimetric Iron Assay Cells were labelled, trypsinised and pelleted then all media removed. 40 µl of 37% HCL was added to the cells and heated at 70° C. until dissolved, then neutralised with 50 µl of NaOH. Those samples containing a high concentration of iron were diluted 1:10 then 40 µl of Quantichrom working reagent was added and the instructions in the Quantichrom iron assay followed.

Flow Cytometry

Cells were labelled with 50 µg of Nanomag-D particles, 1 µM P218R and either 0, 0.1, 1 and 5 µg/ml of FitC-BSA. Cells were then fixed cells and run through a Coulter Altra flow cytometer to assess the green fluorescence. Findings were then statistically analysed by Wesal software.

Results

Nanoparticle and Cell Labelling

Nanomag-D (250 nm) particles were successfully labelled with mR, P21mR, 8RmR and P21mR8R as shown in FIG. 32. The graphs clearly show a reduction in fluorescence in the post labelling solution and an increased fluorescence on the particles hypothesising that the protein has reacted with carboxylic acid group and bonded to the surface of the Nanomag particles. The graphs show that not all of the protein has reacted with the particle surface but considering the proteins were added in excess this was not seen as an issue. Another feature of the graphs is that the P21 domain compared with the 8R has a higher affinity for binding to the particles as there is a more distinctive reduction in fluorescence post labelling and a more intense signal exhibited from the nanoparticles for the P21. Considering that the protein was added in excess of the particles binding capacity such a reduction was unexpected. The P21 domain's role is that it binds to the HS on a cell's membrane, it could also be concluded that the protein is binding to the dextran surface of the particles considering the similar structures of the two substances.

To further test the hypothesis of the P21 binding to the dextran surface both particles which have been pre-labelled with P21mR8R were added to cells and particles and P218R were separately added to cells. The results of the prussian blue stain is shown in FIG. 32. For the unlabelled particle control no blue staining was seen therefore concluding a limited number of particles must have been associated with cells. However for both variables the stain had reacted producing a blue colour even when the protein was not pre-bound. The protein must have bound to the particle at some point in order for particle uptake to occur. The most likely hypothesis is that the P21 is binding to the dextran surface.

Quantitative Assessment of Nanoparticle Uptake

Optimisation of Protein Concentration

As shown in FIG. 33, Prussian blue staining proves that the P218R is the most effective peptide for particle uptake compared to P21 and 8R alone. The iron assay results showed that when cells are incubated for 24 hours with 1 µM of P218R and 50 µg of Nanomag-D particles 100% of the particles become associated with the cells and 63 µg/cell. Therefore it was concluded that only 1 µM of P218R is needed for 100% uptake of particles.

Assessing the Time Taken for Nanoparticle Cell Association

All results indicated that optimum nanoparticle cell association is at 24 hours, as shown in FIG. 34. As at the 24 hour time point 100% of the particles are associated with the cells; this also fits with the results shown in FIG. 33. The graph is also clear evidence of the dramatic increase in particle uptake with the added peptide, from this information the percentage uptake increases from 7% without the added peptide to 96% with the added peptide after 24 hours.

Effect of Serum Free Media

Results in FIG. 35 show a 30% decrease in uptake as the percentage of serum increases to 20%. This decrease reduces to only 16% when 1 µM P218R is added. This decrease in uptake as the amount of serum increases has been attributed to the decrease in endocytosis, as serum free conditions induce endocytosis due to the decrease in nutrients. If the endocytosis decrease is reduced when the peptide is added then it could be assumed that it increases endocytosis. It was found that the addition of the peptide increased endocytosis as the amount of Fitc-BSA taken up by cells increases, whereas the nanoparticles did not affect the uptake, these results are shown in FIG. 35. The increase in uptake of FitC-BSA could be correlated to an increase in endocytosis leading to an increase in particle uptake. There is a less distinctive difference when cells are in serum free conditions as the serum free alone increases endocytosis.

Competing Factors for P21 Binding

It has been proven that the P21 binds to HS on cell membranes, therefore it can be hypothesised that if heparin is added to the media it will competitively inhibit the binding and therefore nanoparticle uptake. Results are shown in FIG. 35. The graph proves that heparin is an inhibitor for the binding and the extent of the inhibition proves that the P21 has a higher affinity for the heparin than the HS on the cell membrane, and therefore proving that the P21 binding is essential to the uptake mechanism of the nanoparticles. P21 may also be binding to the dextran on the surface of the nanoparticles therefore increasing concentrations of dextran was added to media. The results are shown in FIG. 35. There is a decrease in nanoparticle uptake of 18% as the dextran concentration increases. The dextran will be acting as a competitive inhibitor for particle binding and due to the limited reduction in inhibition the P21 has a higher affinity for the cell membrane.

Discussion

The results show that the addition of a small amount of P218R leads to 100% uptake of iron oxide nanoparticles. Microscopy and the trypsinisation of the cells indicate that the particles are being internalised. Experiments were also conducted using mesenchymal stem cells showing a 90% association of particles. The mechanism behind the uptake is dependent on the symbiotic action of the two domains of the peptide, The hypothesis is that the P21 can bind to both the HS on the cell membrane and the dextran in the coating of the nanoparticles, the peptide either has multiple binding points by which both nanoparticle and cell can both be attached to the same P21. Therefore the pre bound protein to the particle can also bind to the membrane keeping the particle in close proximity to the cell. The 8R can then aid in the transduction of the nanoparticle by endocytosis. Or the other mechanism could involve the peptide pre binding to the nanoparticle then when in close proximity to a cell membrane the HS has a higher binding efficiency so the P21 then binds to the cell. This may then lead to the particle being internalised. The advantages of using the P218R peptide is its efficiency in serum media which is more relatable to the in vivo environment and that the system does not require the use of the functional group on the nanoparticles surface coating. The free functional group means that targeting molecules or drugs can be covalently attached to the particle.

Conclusion

The peptide P218R has been found to cause 100% cell association of nanoparticles. This has been found to be due to a dextran binding mechanism which can be utilised for many applications for example targeting of nanoparticles for specific tissues by attaching antibodies, or drug delivery.

REFERENCES

1. Singh, A & Sahoo, S, (2013), Magnetic Nanoparticles: a novel platform for theranostics, Drug Disc Today,
2. Arruebo, M et al, (2007) Magnetic Nanoparticles for drug delivery, Nanotoday, 3, 22
3. Wang, Z and Cuschieri A, (2013) Tumor cell labelling by magnetic nanoparticles with determination of intracellular iron content and spatial distribution of the intracellular iron, Int. J. Mol. Sci, 14, 9111
4. Sun, C. Lee, J and Zhang, M, (2008), Magnetic Nanoparticles in MR Imaging and drug delivery, Adv Drug Deli Rev, 60, 1253
5. Schlorf, T et al, (2011), Biological properties of iron oxide nanoparticles for cellular and molecular magnetic resonance imaging, Int. J. Mol. Sci. 12, 12
6. Markides, I I et al. (2013) Whole body tracking of superparamagnetic iron oxide nanoparticle labelled cells—a rheumatoid arthritis mouse model, Stem cell Res & ther, 4, 126
7. Peng et al, (2008), targeted magnetic iron oxide nanoparticles for tumour imaging and therapy, Int. J. of Nanomed. 3, 311
8. Zhang, C et al, (2007), Specific Targeting of Tumor Angiogenesis by RGD-Conjugated Ultrasmall Superparamagnetic Iron Oxide Particles Using a Clinical 1.5-T Magnetic Resonance Scanner, Can. Res. 67, 1555
9. Ji, S et al. (2012), RGD-conjugated albumin nanoparticles as a novel delivery vehicle in pancreatic cancer therapy, Cancer Biology & Therapy 13:4, 206.

Modified CPPs for Efficient Cell Type Specific Delivery of Therapeutic Molecules Via GET (Glycosaminoglycan (GAG)-Binding Enhanced Transduction)

Introduction

The first aim of this study was to investigate whether the GET-mediated synergistic increase in delivery of mRFP into cells with P21 8R could be observed when P21 was replaced by growth factor derived HS-GAG binding domains. The second aim of this study was to show cell type specific delivery in a heterogeneous population of cells by targeting a specific cell surface HS-epitope. Merry et al have demonstrated the utility of a HS-epitope binding antibody in targeting a subpopulation of cells during mesodermal differentiation [13]. The variable region of this antibody was conjugated to 8R to show an example of cell type specific delivery. The third aim of this study was to demonstrate the GET-mediated delivery of therapeutic biomolecules. The transfection of reporter gene (pSIN GFP) was optimized with P21 LK15 8R peptide and compared to a 'gold standard' commercial lipid based transfection reagent Lipofectamine2000.

Cell Type Specific Delivery Via GET

Experimental Procedures

Preparation of Peptides Peptides, mRFP, mRFP 8R, P21 mRFP 8R, FGF1A mRFP, FGF1A mRFP 8R, FGF2A mRFP, FGF2A mRFP 8R, FGF4A mRFP, FGF4A mRFP 8R, FGF7A mRFP, FGF7A mRFP 8R, FGF1B mRFP, FGF1B mRFP 8R, FGF2B mRFP, FGF2B mRFP 8R, FGF4B mRFP, FGF4B mRFP 8R, FGF7B mRFP, FGF7B mRFP 8R, FGF1C mRFP, FGF1C mRFP 8R, FGF2C mRFP, FGF2C mRFP 8R, FGF4C mRFP. FGF4C mRFP 8R, FGF7C mRFP, FGF7C mRFP 8R, ATIII mRFP, ATIII mRFP 8R. PDGF mRFP, PDGF mRFP 8R, VEGF mRFP, VEGF mRFP 8R. HS4C3 mRFP and HS4C3 mRFP 8R, were cloned as cDNAs into pGEX6-PI vector (Novagen), expressed in 13121 (DE21) pLysS Escherichia coli (Novagen) and purified as previously described [12]. Integrity and full length peptide expression was confirmed by SDS-PAGE. Fluorescence of the recombinant peptides was confirmed using the TECAN infinite 200PRO multimode reader, the difference in fluorescence intensity measurements between samples was <10%.

Peptide Assay

Bradford assay was used to quantify protein concentration [14]. Absorbance was measured at 595 nm using recombinant mRFP protein as a standard [12]. Samples were analysed using the TECAN infinite 200PRO multimode reader.

Cell Culture of NIH3T3, CGR-8 and HUES7 Cells

NIH3T3, CGR-8 and HUES7 cells were grown and maintained as previously described [12]. NIH3T3 mouse fibroblast cells were maintained in Dulbecco's modified Eagle's medium (DMEM) with 10% (v/v) fetal calf serum (FCS) supplemented with 2 mM L-glutamine and 100 ug/ml streptomycin. CGR-8 mouse embryonic stem cells were maintained in DMEM with 20% (v/v) FCS supplemented with 1000 units/ml leukaemia inhibitory factor (LIF), 100 µM β-mecaptoethanol, 2 mM L-glutamine and 100 ug/ml streptomycin. HUES7 human embryonic stem cells were cultured on gelatin coated tissue culture flask. The cells were maintained in DMEM with 20% (v/v) FCS supplemented with 1000 units/ml LIF, 100 µM β-mecaptoethanol, 2 mM L-glutamine and 100 ug/ml streptomycin. All cells were incubated at 37° C. under humidified 5% $CO_2$ conditions.

Peptide Delivery to Cells

Cells were seeded at $2 \times 10^5$ cells/well in 12-well plates and incubated for 2 h in 1 mL of relevant growth media (GM) at 37° C. in a 5% $CO_2$ humidified incubator. The peptide was diluted to 20 ug/ml in 500 ul of GM. Each well of cells was aspirated, washed with phosphate buffered saline (PBS) and replaced with 500 ul of peptide solution. The cells were incubated with the peptide at 37° C. in a 5% $CO_2$ humidified atmosphere for 20 h. Following incubation, each well of cells was washed with PBS, trypsinized and fixed with 3.7% paraformaldehyde (PFA) in preparation for flow cytometry. Each experiment was done in duplicate and repeated 3 times, n=3.

Maintenance and Differentiation of Bry-GFP ES Cells, Generation of EBs

Bry-GFP murine embryonic stem cell line was maintained and differentiated as previously described [13]. Bry-GFP cells were maintained on feeders in DMEM-ES (DMEM with 15% FCS supplemented with $1.5 \times 10^5$ M monothioglycerol (MTG), 10 ng/ml LIF and 2 mM L-glutamine).

Bry-GFP cells were differentiated as EBs. Prior to differentiation the cells were passaged twice, first onto a gelatin coated flask in DMEM-ES and second into a flask in Iscove's modified Dulbecco's medium (IMDM)-ES (IMDM with 15% FCS supplemented with $1.5 \times 10^4$ M monothioglycerol (MTG), 10 ng/ml LIF and 2 mM L-glutamine). Cells were then differentiated as EBs for 2.8 days in IMDM with 15% FCS supplemented with $4 \times 10^4$ M MTG, 300 ug/ml transferrin, 25 ug/ml ascorbic acid and 2 mM L-glutamine in Petri-grade dishes. 3 h before dissociation, EBs were treated with 50 ug/ml of HS4C3 mRFP or HS4C3 mRFP 8R. Following differentiation EBs were separated into single cells by 10 min incubation and agitation in cell dissociation buffer and fixed in PFA.

Flow Cytometry Analysis

Cells were analysed on a MoFlo™ DP (DAKO) Flow Cytometer using a 488 nm green laser and/or 633 nm red laser. (40,000 cells; gated on live cells by forward/side scatter). Median fluorescence was used for statistical analyses.

Results and Discussion

CPPs Modified to Include GET

In this study the HS-GAG binding domains of fibroblast growth factor (FGF)-1, FGF-2, FGF-4, FGF-7, platelet derived growth factor (PDGF) and antithrombin-III (ATIII) were coupled to 8R. These growth factors play important biological roles in embryonic development and angiogenesis. They have also been shown to interact with cell surface HS-GAGs, similarly to P21. NIH 3T3 murine fibroblasts, CGR8 murine embryonic stem cells and HUES-7 human embryonic stem cells were treated with these modified CPPs to investigate whether any of the peptides demonstrated a GET-mediated increase in delivery of mRFP (FIG. 37). It was also important to explore whether any of the modified peptides would preferentially target HS epitopes that were more abundantly expressed in any of the different cell types.

A panel of four modified CPPs that showed GET-mediated enhanced transduction into cells have been identified. P21 8R, FGF2B 8R, FGF7B 8R and PDGF 8R have demonstrated 30-100 fold increase in transduction of mRFP into cells over using an 8R alone (FIGS. 38 and 39). P21 8R, FGF7B 8R and PDGF 8R showed preferential transduction into HUES-7 embryonic stem cells. This demonstrates preferential transduction of CPPs into a cell-type that is considered difficult to transduce in to. FGF2B 8R showed pluripotency specific transduction into CGR8 and HUES7 embryonic stem cells. The diverse delivery profiles of the modified CPPs into the three cell types suggests the HS-GAG binding domains of different growth factors target and bind different cell surface HS-epitopes. Targeting HS-epitopes that are expressed more abundantly by specific cell types can be utilized for the selection of CPPs that are more suitable for their application.

GET Mediated Delivery of Plasmid DNA

Experimental Procedures

Preparation of Peptides

P21-LK15-8R peptide was synthesised using solid phase t-Boc chemistry (Novabiochem (Beeston, Nottinghamshire, UK)).

Cell Culture

NIH3T3 mouse fibroblast cells were maintained in DMEM with 10% (v/v) fetal calf serum (FCS) media supplemented with 2 mM L-glutamine and 100 ug/ml streptomyocin. The cells were incubated at 37° C. under humidified 5% $CO_2$ conditions.

Preparation of Plasmid DNA

DNA (pSIN GFP) was amplified in E. coli. The DNA was extracted and purified using a QIAGEN Plasmid Maxi kit (Qiagen). DNA was precipitated in 100% ethanol and rehydrated in $dH_2O$. Plasmid purity was confirmed using the nanodrop.

Peptide-DNA Complexation Assay 10 ug DNA was diluted in 60 ul 4-(2-hydroxyethyl)-1-piperazineethanesulfonic acid (HEPES)-buffered saline (10 mM HEPES, 150 mM sodium chloride (NaCl) solution. pH 7.4). 1 mM YO-PRO-1 stock solution was diluted to 0.1 mM in dimethyl sulfoxide (DMSO). 2.7 ul of the diluted YO-PRO-1 solution was made up to 60 ul in HEPES-buffered saline and added dropwise to the diluted DNA. The DNA/YO-PRO-1 solution was mixed, wrapped in foil and incubated for 5 h at room temperature. After 5 h, the DNA/YO-PRO-1 solution was made up to 1 ml in HEPES-buffered saline and 100 ul aliquots were pipetted into eppindorf tubes per treatment condition. Peptide amounts corresponding to the desired (+/−) charge ratios were added to each eppindorf (Appendix 1). Peptide/DNA/YO-PRO-1 solutions were mixed and incubated at room temperature for 10 min. Fluorescence measurements were then analysed using the TECAN infinite 200PRO multimode reader. Similarly, a no DNA control was made by diluting 2.7 ul of the diluted YO-PRO-1 solution in 120 ul HEPES-buffered saline and following the procedure above.

Design and Optimization of Transfection Experiment

Cells were seeded at 80,000 cells per well on 12-well plates and incubated overnight in 1 mL of 10% GM at 37° C. in a 5% $CO_2$ humidified incubator. For each well of cells to be transfected. DNA was diluted in 100 ul Opti-MEMR and mixed. The peptide was added directly to the diluted DNA at the optimal (~+/−) charge ratio. The solution was then mixed and incubated for 25 min at room temperature. The cells were aspirated, washed with PBS and replaced with 400 ul Opti-MEM®. Each well of cells was treated with 100 ul of Peptide/DNA complex and incubated 37° C. in a 5% $CO_2$ humidified atmosphere. Appendix 2 shows the different treatment conditions used for each well. Following incubation, the cells were washed with PBS and replaced with 1 ml GM. After 48 h, each well of cells was washed with PBS, trypsinized and fixed with 3.7% PFA. Experiments were repeated 3 times.

Lipofectamine2000 transfection optimization was carried out as described in the manufacturers guide (Invitrogen). Cells were seeded at 80,000 cells per well on 12-well plates and incubated overnight in 1 mL of GM at 37° C. in a 5% $CO_2$ humidified incubator. For each well of cells to be transfected, DNA was diluted in 100 ul Opti-MEM® and mixed. 1.5 ul of Lipofectamine2000 was added directly to the diluted DNA. The mixture was then mixed and incubated for 25 mins at room temperature. The cells were aspirated, washed with PBS and replaced with 400 ul Opti-MEM®. Each well of cells was treated with 100 ul of Lipofectamine2000/DNA complex and incubated 37° C. in a 5% $CO_2$ humidified atmosphere. After 6 h, the cells was washed with PBS, trypsinized and fixed with 3.7% PFA. This was repeated with varying volumes of Lipofectamine2000 (3 ul and 4.5 ul) to find the optimal ratio of Lipofectamine2000 to DNA. Experiments were repeated 3 times.

Flow Cytometry Analysis

Cells were analysed on a MoFlo™ DP (DAKO) Flow Cytometer using a 633 nm red laser. (40.000 cells: gated on live cells by forward/side scatter). Median fluorescence was used for statistical analyses.

Results and Discussion

Peptide to DNA Binding

YO-PRO-1 assay can be used to investigate the DNA condensation ability of a DNA binding peptide. YO-PRO-1 is a cyanine dye that binds DNA to form a fluorescent DNA/dye complex. Different (+/−) charge ratios of peptide can be added to the fluorescent DNA/dye complex. As the peptide out competes the dye by binding the DNA a reduction in fluorescence intensity is observed. In this study, LK15 was fused to P21 8R transduction protein to improve the DNA binding ability of the modified cell penetrating peptide. Fusion of LK15 peptide to TAT has been shown to significantly improve transfection of pDNA into HT29 and HT1080 cultured cells [19]. Enhanced transduction efficiency of Tat-LK15 over Tat is thought to be due to the improved condensation ability of the peptide and DNA, and better transduction of the DNA across the cell membrane [20].

A graph of (+/−) charge ratio was plotted against % fluorescence to investigate the optimum ratio of P21 LK15 8R to pSIN GFP (FIG. 40). Results showed that the optimal (+/−) charge ratio of P21 LK15 8R to pSIN GFP was 2:1, respectively. This ratio was used in the transfection experiments.

Transfection of pDNA Reporter Gene Via P21 LK15 8R

The phospholipid bilayer of the cell membrane acts as an impenetrable barrier to nucleic acids and thus pDNA will be conjugated to a modified CPP to facilitate its transport into the cell [2]. In this study the GET-mediated transfection of the reporter gene pSIN GFP into NIII 3T3 murine fibroblast cells was optimized in terms of transfection time (3, 6 or 24 h), transfection media (with or without serum) and amount of DNA (1, 4 or 10 ug). The reporter gene pSIN GFP was transfected into cells using P21 LK15 8R where P21 targets and binds cell surface HS-GAGs, LK15 complexes pSIN GFP and 8R transduces pSIN GFP across the cell membrane. The transfection efficiency of pSIN GFP with P21 LK15 8R was compared to the transfection efficiency of commercially used lipid-based transfection reagent lipofectamine2000. Cells were fixed at 48 h following transfection to allow time for the transient expression of GFP to be captured and transfection efficiencies were quantified by flow cytometry (FIG. 41).

Gene carrier systems must be serum resistant for efficacious in-vivo applications, however most gene carries, including lipofectamine2000, have demonstrated steep decreases in transfection efficiency in serum containing media [21]. This is believed to be because serum molecules competitively bind the gene carrier, therefore decreasing free gene carriers available to bind the DNA [22]. The transfection efficiency of P21 LK15 8R was characterised in serum and serum free transfection media. The optimal transfection conditions were when cells were transfected with 10 ug DNA for 24 h in serum conditions where transfection efficiency reached 17.9±4.8%. (FIG. 42). This is 3 fold lower than the optimized transfection efficiency observed for lipofectamine2000 in serum free conditions (54.7±10.3%, Appendix 3) however, the serum-resistance of P21 LK15 8R transfection is advantageous for any sort of clinical/in-vivo delivery of therapeutic biomolecules. In addition, it is well documented that endosomal escape strategies greatly increase the efficiencies of CPP-mediated transfections.

Conclusions

A panel of CPPs that have been modified to include growth factor derived cell surface HS-GAG binding domains have shown 30-100 fold increase in transduction into cells, compared to unmodified CPPs. The hypothesis is that the GET-mediated delivery of these peptides is due to the dual functionality of the peptide in i) increasing interaction with the cell membrane via the HS-GAG binding domain, and ii) transducing protein across cell membrane via 8R. The modified CPPs showed preferential delivery profiles of mRFP into different cell types, this is due the HS-GAG binding domains targeting specific HS-epitopes that are more abundantly expressed in different cell types. Future work is to modify CPPs to include specific antibody-derived HS-epitope binding domains. HS-epitope binding libraries of antibodies can be utilized for the cell type specific delivery of therapeutic molecules via GET.

To demonstrate the utility of these peptides for the delivery of therapeutic molecules P21 LK15 8R was used to deliver the reporter gene pSIN GFP into cells. Results showed GET-mediated transfection efficiencies of up to 17.9±4.8% in serum conditions, without any endosomal escape strategy. CPPs modified to include HS-GAG binding domains show great promise as alternatives to using viral and lipid based delivery vehicles for the in-vivo delivery of therapeutic biomolecules.

REFERENCES

[1] Bechara C, Sagan S. Cell-penetrating peptides: 20 years later, where do we stand?Febs Letters 2013; 587:1693-702.

[2] Tanaka K, Kanazawa T, Ogawa T, Suda Y, Takashima Y, Fukuda T, et al. A Novel, Bio-Reducible Gene Vector Containing Arginine and Histidine Enhances Gene Transfection and Expression of Plasmid DNA. Chemical & Pharmaceutical Bulletin 2011; 59:202-7.

[3] Mitchell D J, Kim D T, Steinman L, Fathman C G, Rothbard J B. Polyarginine enters cells more efficiently than other polycationic homopolymers. Journal of Peptide Research 2000:56:318-25.

[4] Nakase I L Niwa M, Takeuchi T, Sonomura K, Kawabata N, Koike Y, et al. Cellular uptake of arginine-rich peptides: Roles for macropinocytosis and actin rearrangement. Molecular Therapy 2004:10:1011-22.

[5] Ma D X. Shi N Q, Qi X R. Distinct transduction modes of arginine-rich cell-penetrating peptides for cargo delivery into tumor cells. International Journal of Pharmaceutics 2011:419:200-8.

[6] El-Sayed A, Futaki S, Hlarashima 11. Delivery of Macromolecules Using Arginine-Rich Cell-Penetrating Peptides: Ways to Overcome Endosomal Entrapment. Aaps Journal 2009:11:13-22.

[7] Shiraishi T, Nielsen P E. Enhanced delivery of cell-penetrating peptide-peptide nucleic acid conjugates by endosomal disruption. Nature Protocols 2006; 1:633-6.

[8] Matsubara Y, Chiba T, Kashimada K, Morio T, Takada S, Mizutani S, et al.

Transcription activator-like effector nuclease-mediated transduction of exogenous gene into IL2R G locus. Scientific Reports 2014; 4.

[9] Parelkar S S, Letteri R, Chan-Seng D, Zolochevska O, Ellis J, Figueiredo M, et al. Polymer-Peptide Delivery Platforms: Effect of Oligopeptide Orientation on Polymer-Based DNA Delivery. Biomacromolecules 2014; 15:1328-36.
[10] Yang H Y, Vonk L A, Licht R, van Boxtel A M G, Bekkers J E J, Kragten A H M, et al. Cell type and transfection reagent-dependent effects on viability, cell content, cell cycle and inflammation of RNAi in human primary mesenchymal cells. European Journal of Pharmaceutical Sciences 2014:53:35-44.
[11] Ma Y, Gong C, Ma Y L, Fan F K, Luo M J, Yang F, et al. Direct cytosolic delivery of cargoes in vivo by a chimera consisting of D- and L-arginine residues. Journal of Controlled Release 2012:162:286-94.
[12] James E. Dixon G M, Nina Lane, Chris Denning and Kevin M. Shakesheff Highly Efficient Delivery of Functional Proteins by the Synergistic Effect of GAG Binding Motifs and Cell-Penetrating Peptides. Unpublished 2014.
[13] Baldwin R J, ten Dam G B, van Kuppevelt T H, Lacaud G, Gallagher J T, Kouskoff V, et al. A Developmentally Regulated Heparan Sulfate Epitope Defines a Subpopulation with Increased Blood Potential During Mesodermal Differentiation. Stem Cells 2008:26:3108-18.
[14] Bradford M M. RAPID AND SENSITIVE METHOD FOR QUANTITATION O F MICROGRAM QUANTITIES O F PROTEIN UTILIZING PRINCIPLE O F PROTEIN-DYE BINDING. Analytical Biochemistry 1976:72:248-54.
[15] Schamhart D H J, Kurth K H. Role of proteoglycans in cell adhesion of prostate cancer cells: From review to experiment. Urological Research 1997; 25:S89-S96.
[16] Delehedde M, Deudon E, Boilly B, Hondermarck H. Proteoglycans in breast cancer.
Pathologic Biologic 1997; 45:305-11.
[17] Shao C, Shi X F, Phillips J J, Zaia J. Mass Spectral Profiling of Glycosaminoglycans from Histological Tissue Surfaces. Analytical Chemistry 2013; 85:10984-91.
[18] Thompson K E, Bashor C J, Lim W A, Keating A E. SYNZIP Protein Interaction Toolbox: in Vitro and in Vivo Specifications of Heterospecific Coiled-Coil Interaction Domains. Acs Synthetic Biology 2012; 1:118-29.
[19] Saleh A F, Aojula H. Arthanari Y, Offerman S, Alkotaji M, Pluen A. Improved Tat-mediated plasmid DNA transfer by fusion to LK15 peptide. Journal of Controlled Release 2010; 143:233-42.
[20] Dufourcq J, Neri W, Henry-Toulme N. Molecular assembling of DNA with amphipathic peptides. Febs Letters 1998; 421:7-11.
[21] Zhang X, Hu H M, Liu T B, Yang Y Y, Peng Y F, Cai Q Q, et al. Multi-armed poly(L-glutamic acid)-graft-polypropyleneinime as effective and serum resistant gene delivery vectors. International Journal of Pharmaceutics 2014; 465:444-54.
[22] Wu H M, Pan S R, Chen M W, Wu Y, Wang C. Wen Y T, et al. A serum-resistant polyamidoamine-based polypeptide dendrimer for gene transfection. Biomaterials 2011; 32:1619-34.

APPENDIX 1

Table showing amounts of P21 LK15 8R added to 1 ug of pSIN GFP at different (+/−) charge ratios

| Peptide/DNA (+/−) Charge Ratio | Concentration of peptide (uM) | Volume of peptide (ul) |
|---|---|---|
| 1:5 | 0.49 | 0.05 |
| 1:3 | 0.82 | 0.07 |
| 1:2 | 1.23 | 0.12 |
| 1:1 | 2.47 | 0.24 |
| 2:1 | 4.94 | 0.49 |
| 3:1 | 7.41 | 0.74 |
| 5:1 | 12.35 | 1.23 |
| 10:1 | 24.7 | 2.46 |

APPENDIX 2

Table showing the different treatment conditions for the optimization of the transfection of pSIN GFP into NIH 3T3 cells by P21 LK15 8R.

| Well | Amount of DNA (ug) | Transfection Media (Optimem, OptiMEM + 10% Serum) | Transfection Time (h) |
|---|---|---|---|
| 1 | 1 | Opti-MEM ® | 3 h |
| 2 | 1 | Opti-MEM ® + 10% serum | 3 h |
| 3 | 1 | Opti-MEM ® | 6 h |
| 4 | 1 | Opti-MEM ® + 10% serum | 6 h |
| 5 | 1 | Opti-MEM ® | 24 h |
| 6 | 1 | Opti-MEM ® + 10% serum | 24 h |
| 7 | 4 | Opti-MEM ® | 3 h |
| 8 | 4 | Opti-MEM ® + 10% serum | 3 h |
| 9 | 4 | Opti-MEM ® | 6 h |
| 10 | 4 | Opti-MEM ® + 10% serum | 6 h |
| 11 | 4 | Opti-MEM ® | 24 h |
| 12 | 4 | Opti-MEM ® + 10% serum | 24 h |
| 13 | 10 | Opti-MEM ® | 3 h |
| 14 | 10 | Opti-MEM ® + 10% serum | 3 h |
| 15 | 10 | Opti-MEM ® | 6 h |
| 16 | 10 | Opti-MEM ® + 10% serum | 6 h |
| 17 | 10 | Opti-MEM ® | 24 h |
| 18 | 10 | Opti-MEM ® + 10% serum | 24 h |

The invention claimed is:

1. A delivery molecule for transduction of a cargo into a cell comprising:
   a cargo, or a cargo-binding molecule for binding to a cargo, and optionally wherein the cargo is bound to the cargo-binding molecule;
   a glycosaminoglycan (GAG) binding element comprising:
   P21 of Heparin-binding EGF-like growth factor (HB-EGF); or
   a GAG binding antibody, which is capable of binding to GAG on the surface of the cell; and
   a protein transduction domain (PTD) wherein the PTD is not a heparin binding domain.

2. The delivery molecule according to claim 1, wherein the GAG binding element comprises P21 of HB-EGF.

3. The delivery molecule according to claim 1, wherein the GAG binding element comprises a GAG binding antibody.

4. The delivery molecule according to claim 3, wherein the GAG binding antibody comprises a single-domain antibody.

5. The delivery molecule according to claim 1, wherein the protein transduction domain is hydrophilic or amphiphilic.

6. The delivery molecule according to claim 1, wherein the protein transduction domain comprises a majority of hydrophilic amino acid residues.

7. The delivery molecule according to claim 1, wherein the protein transduction domain comprises a majority of arginine and/or lysine amino acid residues.

8. The delivery molecule according to claim 1, wherein the protein transduction domain is selected from any of the group comprising:

Penetratin or Antenapedia PTD
(SEQ ID NO: 37)
RQIKWFQNRRMKWKK;

HIV transactivator protein (TAT)
(SEQ ID NO: 38)
YGRKKRRQRRR;

Synembryn B (SynB)1
(SEQ ID NO: 39)
RGGRLSYSRRRFSTSTGR;

SynB3
(SEQ ID NO: 40)
RRLSYSRRRF;

PTD-4
(SEQ ID NO: 41)
PIRRRKKLRRLK;

PTD-5
(SEQ ID NO: 42)
RRQRRTSKLMKR;

Flock house virus (FHV) Coat-(35-49)
(SEQ ID NO: 43)
RRRRNRTRRNRRRVR;

Brome mosaic virus (BMV) Gag-(7-25)
(SEQ ID NO: 44)
KMTRAQRRAAARRNRWTAR;

Human T-cell lymphotrophic virus (HTLV)-II Rex-(4-16)
(SEQ ID NO: 45)
TRRQRTRRARRNR;

D-Tat
(SEQ ID NO: 46)
GRKKRRQRRRPPQ;

R9-Tat
(SEQ ID NO: 47)
GRRRRRRRRRPPQ;

Transportan
(SEQ ID NO: 48)
GWTLNSAGYLLGKINLKALAALAKKIL chimera;

Microtubule-associated protein (MAP)
(SEQ ID NO: 49)
KLALKLALKLALALKLA;

Streptavidin-binding Peptide (SBP)
(SEQ ID NO: 50)
MGLGLHLLVLAAALQGAWSQPKKKRKV;

Folate-binding protein (FBP)
(SEQ ID NO: 51)
GALFLGWLGAAGSTMGAWSQPKKKRKV;

Human 3-methyladenine-DNA glycosylase (MPG)
(SEQ ID NO: 52)
ac-GALFLGFLGAAGSTMGAWSQPKKKRKV-cya;

MPG-nuclear localisation sequence (NLS)
(SEQ ID NO: 53)
ac-GALFLGFLGAAGSTMGAWSQPKSKRKV-cya;

Pep-1
(SEQ ID NO: 54)
ac-KETWWETWWTEWSQPKKKRKV-cya;
and

-continued

```
Pep-2
                                          (SEQ ID NO: 55)
ac-KETWFETWFTEWSQPKKKRKV-cya;
or polyarginines, polylysines, (RAca)6R, (RAbu)6R,
(RG)6R, (RM)6R, (RT)6R. (RS)6R, R10, (RA)6R, R7,
and R8.
```

9. The delivery molecule according to claim 1, wherein the protein transduction domain comprises about 8 arginine residues.

10. The delivery molecule according to claim 1, wherein the cargo is selected from any of the group comprising a peptide, a protein, a nucleic acid, and a nanoparticle.

11. The delivery molecule according to claim 1, wherein the cargo is selected from any of the group comprising a therapeutic molecule; a drug; and a pro-drug; a functional protein or peptide.

12. The delivery molecule according to claim 1, wherein the cargo is between about 20 and about 30,000 amino acids in length.

13. The delivery molecule according to claim 1, wherein the cargo-binding molecule comprises any of a peptide, a protein, streptavidin, a nucleic acid-binding molecule, an antibody, or fragment thereof, an antibody mimetic, a chemical linker molecule, an affinity tag, or an affinity tagged molecule.

14. A cell comprising or encoding the delivery molecule in accordance with claim 1.

15. A nucleic acid encoding the delivery molecule according to claim 1.

* * * * *

SEQUENCE LISTING

<160> NUMBER OF SEQ ID NOS: 57

<210> SEQ ID NO 1
<211> LENGTH: 21
<212> TYPE: PRT
<213> ORGANISM: Homo sapiens

<400> SEQUENCE: 1

Lys Arg Lys Lys Lys Gly Lys Gly Leu Gly Lys Lys Arg Asp Pro Cys
1               5                   10                  15

Leu Arg Lys Tyr Lys
            20

<210> SEQ ID NO 2
<211> LENGTH: 63
<212> TYPE: DNA
<213> ORGANISM: Homo sapiens

<400> SEQUENCE: 2
aagcgcaaga agaagggcaa aggcctgggc aagaagcgcg atccgtgcct gcgcaagtat    60
aag                                                                  63

<210> SEQ ID NO 3
<211> LENGTH: 18
<212> TYPE: PRT
<213> ORGANISM: Homo sapiens

<400> SEQUENCE: 3

Gly Arg Pro Arg Glu Ser Gly Lys Lys Arg Lys Arg Lys Arg Leu Lys
1               5                   10                  15

Pro Thr

<210> SEQ ID NO 4
<211> LENGTH: 54
<212> TYPE: DNA
<213> ORGANISM: Homo sapiens

<400> SEQUENCE: 4
ggccgcccgc gcgaaagcgg caaaaaacgc aaacgcaaac gcctgaaacc gacc          54

<210> SEQ ID NO 5
<211> LENGTH: 20
<212> TYPE: PRT
<213> ORGANISM: Homo sapiens

<400> SEQUENCE: 5

Thr Tyr Ala Ser Ala Lys Trp Thr His Asn Gly Gly Glu Met Phe Val
1               5                   10                  15

Ala Leu Asn Gln
            20

<210> SEQ ID NO 6
<211> LENGTH: 60
<212> TYPE: DNA
<213> ORGANISM: Homo sapiens

<400> SEQUENCE: 6
acctatgcga gcgcgaaatg gacccataac ggcggcgaaa tgtttgtggc gctgaaccag    60

<210> SEQ ID NO 7
<211> LENGTH: 16
<212> TYPE: PRT
<213> ORGANISM: Homo sapiens

<400> SEQUENCE: 7

Thr Tyr Arg Ser Arg Lys Tyr Thr Ser Trp Tyr Val Ala Leu Lys Arg
1               5                   10                  15

```
<210> SEQ ID NO 8
<211> LENGTH: 48
<212> TYPE: DNA
<213> ORGANISM: Homo sapiens

<400> SEQUENCE: 8
acctatcgca gccgcaaata taccagctgg tatgtggcgc tgaaacgc                    48

<210> SEQ ID NO 9
<211> LENGTH: 24
<212> TYPE: DNA
<213> ORGANISM: Artificial Sequence
<220> FEATURE:
<223> OTHER INFORMATION: Transduction domain sequence

<400> SEQUENCE: 9
cgaagacgca ggagacgtcg aagg                                              24

<210> SEQ ID NO 10
<211> LENGTH: 88
<212> TYPE: DNA
<213> ORGANISM: Artificial Sequence
<220> FEATURE:
<223> OTHER INFORMATION: Delivery molecule sequence
<220> FEATURE:
<221> NAME/KEY: misc_feature
<222> LOCATION: (64)..(64)
<223> OTHER INFORMATION: n is a, c, g, or t

<400> SEQUENCE: 10
aagcgcaaga agaagggcaa aggcctgggc aagaagcgcg atccgtgcct gcgcaagtat       60
aagncgaaga cgcaggagac gtcgaagg                                          88

<210> SEQ ID NO 11
<211> LENGTH: 118
<212> TYPE: PRT
<213> ORGANISM: Artificial Sequence
<220> FEATURE:
<223> OTHER INFORMATION: Binding molecule

<400> SEQUENCE: 11

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Gly Thr Ala Ala Tyr Tyr Cys Gly Arg
                85                  90                  95

Arg Leu Lys Asp Pro Ser Thr Pro Pro Thr Pro Ser Pro Ser Thr Pro
            100                 105                 110

Pro Thr Pro Ser Pro Ser
        115

<210> SEQ ID NO 12
<211> LENGTH: 354
<212> TYPE: DNA
<213> ORGANISM: Artificial Sequence
<220> FEATURE:
```

<223> OTHER INFORMATION: Binding molecule

<400> SEQUENCE: 12

| | |
|---|---|
| gaagtgcagc tggtggaaag cggcggcggc tggtgcagc cgcgcggcag cctgcgcctg | 60 |
| agctgcgcgg cgagcggctt taccgtgagc agcaacgaaa tgagctggat tcgccaggcg | 120 |
| ccgggcaaag gcctggaatg ggtgagcagc attagcggcg gcagcaccta ttatgcggat | 180 |
| agccgcaaag gccgctttac cattagccgc gataacagca aaaacaccct gtatctgcag | 240 |
| atgaacaacc tgcgcgcgga aggcaccgcg gcgtattatt gcggccgccg cctgaaagat | 300 |
| ccgagcaccc cgccgacccc gagcccgagc accccgccga ccccgagccc gagc | 354 |

<210> SEQ ID NO 13
<211> LENGTH: 129
<212> TYPE: PRT
<213> ORGANISM: Artificial Sequence
<220> FEATURE:
<223> OTHER INFORMATION: Binding molecule

<400> SEQUENCE: 13

```
Gln Val Gln Leu Val Glu Ser Gly Gly Gly Ser Val Gln Ala Gly Gly
1               5                   10                  15
Ser Leu Arg Leu Ser Cys Thr Ala Ser Gly Phe Thr Val Ser Ser Asn
            20                  25                  30
Glu Leu Gly Trp Phe Arg Gln Ala Pro Gly Gln Glu Arg Trp Ala Val
        35                  40                  45
Ala Ala Ile Ser Gly Gly Ser Thr Tyr Tyr Ala Asp Ser Val Lys Gly
    50                  55                  60
Arg Phe Thr Ile Ser Arg Asp Asn Ala Lys Asn Thr Val Thr Leu Gln
65                  70                  75                  80
Met Asn Asn Leu Lys Pro Glu Asp Thr Ala Ile Tyr Tyr Cys Gly Arg
                85                  90                  95
Arg Leu Lys Asp Trp Gly Gln Gly Thr Gln Val Thr Val Ser Ser Pro
            100                 105                 110
Ser Thr Pro Pro Thr Pro Ser Pro Ser Thr Pro Pro Thr Pro Ser Pro
        115                 120                 125
Ser
```

<210> SEQ ID NO 14
<211> LENGTH: 387
<212> TYPE: DNA
<213> ORGANISM: Artificial Sequence
<220> FEATURE:
<223> OTHER INFORMATION: Binding molecule

<400> SEQUENCE: 14

| | |
|---|---|
| caggtgcagc tggtggaaag cggcggcggc agcgtgcagg cgggcggcag cctgcgcctg | 60 |
| agctgcaccg cgagcggctt taccgtgagc agcaacgaac tgggctggtt tcgccaggcg | 120 |
| ccgggccagg aacgctgggc ggtggcggcg attagcggcg gcagcaccta ttatgcggat | 180 |
| agcgtgaaag gccgctttac cattagccgc gataacgcga aaacaccgt gaccctgcag | 240 |
| atgaacaacc tgaaaccgga agataccgcg atttattatt gcggccgccg cctgaaagat | 300 |
| tggggccagg gcacccaggt gaccgtgagc agcccgagca ccccgccgac cccgagcccg | 360 |
| agcaccccgc cgaccccgag cccgagc | 387 |

<210> SEQ ID NO 15
<211> LENGTH: 124

```
<212> TYPE: PRT
<213> ORGANISM: Artificial Sequence
<220> FEATURE:
<223> OTHER INFORMATION: Binding molecule

<400> SEQUENCE: 15

Glu Asp Gln Leu Val Glu Ser Gly Gly Gly Leu Val Gln Pro Gly Gly
1               5                   10                  15

Ser Leu Arg Pro Ser Cys Ala Ala Ser Gly Phe Ala Phe Ser Ser Tyr
            20                  25                  30

Ala Leu His Trp Val Arg Arg Ala Pro Gly Lys Gly Leu Glu Trp Val
        35                  40                  45

Ser Ala Ile Gly Thr Gly Gly Asp Thr Tyr Tyr Ala Asp Ser Val Met
    50                  55                  60

Gly Arg Phe Thr Ile Ser Arg Asp Asn Ala Lys Lys Ser Leu Tyr Leu
65                  70                  75                  80

His Met Asn Ser Leu Ile Ala Glu Asp Met Ala Val Tyr Tyr Cys Ser
                85                  90                  95

Leu Arg Met Asn Gly Trp Arg Ala His Gln Pro Ser Thr Pro Pro Thr
            100                 105                 110

Pro Ser Pro Ser Thr Pro Thr Pro Ser Pro Ser
        115                 120

<210> SEQ ID NO 16
<211> LENGTH: 372
<212> TYPE: DNA
<213> ORGANISM: Artificial Sequence
<220> FEATURE:
<223> OTHER INFORMATION: Binding molecule

<400> SEQUENCE: 16
gaagatcagc tggtggaaag cggcggcggc ctggtgcagc cgggcggcag cctgcgcccg     60
agctgcgcgg cgagcggctt tgcgtttagc agctatgcgc tgcattgggt gcgccgcgcg    120
ccgggcaaag gcctggaatg ggtgagcgcg attggcaccg gcggcgatac ctattatgcg    180
gatagcgtga tgggccgctt taccattagc cgcgataacg cgaaaaaaag cctgtatctg    240
catatgaaca gcctgattgc ggaagatatg gcggtgtatt attgcagcct gcgcatgaac    300
ggctggcgcg cgcatcagcc gagcaccccg ccgaccccga gccgagcac ccgccgacc    360 ccgagcccga gc                                                        372

<210> SEQ ID NO 17
<211> LENGTH: 135
<212> TYPE: PRT
<213> ORGANISM: Artificial Sequence
<220> FEATURE:
<223> OTHER INFORMATION: Binding molecule

<400> SEQUENCE: 17

Gln Val Gln Leu Val Glu Ser Gly Gly Gly Ser Val Gln Ala Gly Gly
1               5                   10                  15

Ser Leu Arg Leu Ser Cys Thr Ala Ser Gly Phe Ala Phe Ser Ser Tyr
            20                  25                  30

Ala Leu Gly Trp Phe Arg Gln Ala Pro Gly Gln Glu Arg Trp Ala Val
        35                  40                  45

Ala Ala Ile Gly Thr Gly Gly Asp Thr Tyr Tyr Ala Asp Ser Val Lys
    50                  55                  60

Gly Arg Phe Thr Ile Ser Arg Asp Asn Ala Lys Asn Thr Val Thr Leu
65                  70                  75                  80
```

```
Gln Met Asn Asn Leu Lys Pro Glu Asp Thr Ala Ile Tyr Tyr Cys Ser
                85                  90                  95

Leu Arg Met Asn Gly Trp Arg Ala His Gln Trp Gly Gln Gly Thr Gln
            100                 105                 110

Val Thr Val Ser Ser Pro Ser Thr Pro Pro Thr Pro Ser Pro Ser Thr
        115                 120                 125

Pro Pro Thr Pro Ser Pro Ser
    130             135

<210> SEQ ID NO 18
<211> LENGTH: 405
<212> TYPE: DNA
<213> ORGANISM: Artificial Sequence
<220> FEATURE:
<223> OTHER INFORMATION: Binding molecule

<400> SEQUENCE: 18
caggtgcagc tggtggaaag cggcggcggc agcgtgcagg cgggcggcag cctgcgcctg      60
agctgcaccg cgagcggctt tgcgtttagc agctatgcgc tgggctggtt tcgccaggcg     120
ccgggccagg aacgctgggc ggtggcggcg attggcaccg cggcgatac ctattatgcg      180 gatagcgtga aggccgcttt accattagc cgcgataacg cgaaaaacac cgtgaccctg      240
cagatgaaca acctgaaacc ggaagatacc gcgatttatt attgcagcct gcgcatgaac     300
ggctggcgcg cgcatcagtg gggccagggc acccaggtga ccgtgagcag cccgagcacc     360
ccgccgaccc cgagcccgag caccccgccg accccgagcc cgagc                    405

<210> SEQ ID NO 19
<211> LENGTH: 8
<212> TYPE: PRT
<213> ORGANISM: Artificial Sequence
<220> FEATURE:
<223> OTHER INFORMATION: Transduction domain

<400> SEQUENCE: 19

Arg Arg Arg Arg Arg Arg Arg Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Transduction domain

<400> SEQUENCE: 20

Arg Lys Lys Arg Arg Gln Arg Arg Arg
1               5

<210> SEQ ID NO 21
<211> LENGTH: 8
<212> TYPE: PRT
<213> ORGANISM: Artificial Sequence
<220> FEATURE:
<223> OTHER INFORMATION: CDR

<400> SEQUENCE: 21

Gly Phe Thr Val Ser Ser Asn Glu
1               5

<210> SEQ ID NO 22
<211> LENGTH: 8
```

```
<212> TYPE: PRT
<213> ORGANISM: Artificial Sequence
<220> FEATURE:
<223> OTHER INFORMATION: CDR

<400> SEQUENCE: 22

Gly Phe Ala Phe Ser Ser Tyr Ala
1               5

<210> SEQ ID NO 23
<211> LENGTH: 6
<212> TYPE: PRT
<213> ORGANISM: Artificial Sequence
<220> FEATURE:
<223> OTHER INFORMATION: CDR

<400> SEQUENCE: 23

Ile Ser Gly Gly Ser Thr
1               5

<210> SEQ ID NO 24
<211> LENGTH: 7
<212> TYPE: PRT
<213> ORGANISM: Artificial Sequence
<220> FEATURE:
<223> OTHER INFORMATION: CDR

<400> SEQUENCE: 24

Ile Gly Thr Gly Gly Asp Thr
1               5

<210> SEQ ID NO 25
<211> LENGTH: 6
<212> TYPE: PRT
<213> ORGANISM: Artificial Sequence
<220> FEATURE:
<223> OTHER INFORMATION: CDR

<400> SEQUENCE: 25

Gly Arg Arg Leu Lys Asp
1               5

<210> SEQ ID NO 26
<211> LENGTH: 11
<212> TYPE: PRT
<213> ORGANISM: Artificial Sequence
<220> FEATURE:
<223> OTHER INFORMATION: CDR

<400> SEQUENCE: 26

Ser Leu Arg Met Asn Gly Trp Arg Ala His Gln
1               5                   10

<210> SEQ ID NO 27
<211> LENGTH: 6
<212> TYPE: PRT
<213> ORGANISM: Artificial Sequence
<220> FEATURE:
<223> OTHER INFORMATION: CDR

<400> SEQUENCE: 27

Gly Met Arg Pro Arg Leu
1               5

<210> SEQ ID NO 28
<211> LENGTH: 11
<212> TYPE: PRT
```

```
<213> ORGANISM: Artificial Sequence
<220> FEATURE:
<223> OTHER INFORMATION: CDR

<400> SEQUENCE: 28

His Ala Pro Leu Arg Asn Thr Arg Thr Asn Thr
1               5                   10

<210> SEQ ID NO 29
<211> LENGTH: 6
<212> TYPE: PRT
<213> ORGANISM: Artificial Sequence
<220> FEATURE:
<223> OTHER INFORMATION: CDR

<400> SEQUENCE: 29

Gly Ser Arg Ser Ser Arg
1               5

<210> SEQ ID NO 30
<211> LENGTH: 7
<212> TYPE: PRT
<213> ORGANISM: Artificial Sequence
<220> FEATURE:
<223> OTHER INFORMATION: CDR

<400> SEQUENCE: 30

Gly Arg Thr Val Gly Arg Asn
1               5

<210> SEQ ID NO 31
<211> LENGTH: 7
<212> TYPE: PRT
<213> ORGANISM: Artificial Sequence
<220> FEATURE:
<223> OTHER INFORMATION: CDR

<400> SEQUENCE: 31

Gly Lys Val Lys Leu Pro Asn
1               5

<210> SEQ ID NO 32
<211> LENGTH: 8
<212> TYPE: PRT
<213> ORGANISM: Artificial Sequence
<220> FEATURE:
<223> OTHER INFORMATION: CDR

<400> SEQUENCE: 32

Ser Gly Arg Lys Gly Arg Met Arg
1               5

<210> SEQ ID NO 33
<211> LENGTH: 7
<212> TYPE: PRT
<213> ORGANISM: Artificial Sequence
<220> FEATURE:
<223> OTHER INFORMATION: CDR

<400> SEQUENCE: 33

Arg Arg Tyr Ala Leu Asp Tyr
1               5

<210> SEQ ID NO 34
<211> LENGTH: 7
<212> TYPE: PRT
<213> ORGANISM: Artificial Sequence
```

-continued

```
<220> FEATURE:
<223> OTHER INFORMATION: CDR

<400> SEQUENCE: 34

Leu Lys Gln Gln Gly Ile Ser
1               5

<210> SEQ ID NO 35
<211> LENGTH: 12
<212> TYPE: PRT
<213> ORGANISM: Artificial Sequence
<220> FEATURE:
<223> OTHER INFORMATION: CDR

<400> SEQUENCE: 35

Ala Met Thr Gln Lys Lys Pro Arg Lys Leu Ser Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: CDR

<400> SEQUENCE: 36

Ser Gly Arg Lys Tyr Phe Arg Ala Arg Asp Met Asn
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Transduction domain

<400> SEQUENCE: 37

Arg Gln Ile Lys Trp Phe Gln Asn Arg Arg Met Lys Trp Lys Lys
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Transduction domain

<400> SEQUENCE: 38

Tyr Gly Arg Lys Lys Arg Arg Gln Arg Arg Arg
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Transduction domain

<400> SEQUENCE: 39

Arg Gly Gly Arg Leu Ser Tyr Ser Arg Arg Arg Phe Ser Thr Ser Thr
1               5                   10                  15

Gly Arg

<210> SEQ ID NO 40
<211> LENGTH: 10
<212> TYPE: PRT
```

<213> ORGANISM: Artificial Sequence
<220> FEATURE:
<223> OTHER INFORMATION: Transduction domain

<400> SEQUENCE: 40

Arg Arg Leu Ser Tyr Ser Arg Arg Arg Phe
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Transduction domain

<400> SEQUENCE: 41

Pro Ile Arg Arg Arg Lys Lys Leu Arg Arg Leu Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Transduction domain

<400> SEQUENCE: 42

Arg Arg Gln Arg Arg Thr Ser Lys Leu Met Lys Arg
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Transduction domain

<400> SEQUENCE: 43

Arg Arg Arg Arg Asn Arg Thr Arg Arg Asn Arg Arg Arg Val Arg
1               5                   10                  15

<210> SEQ ID NO 44
<211> LENGTH: 19
<212> TYPE: PRT
<213> ORGANISM: Artificial Sequence
<220> FEATURE:
<223> OTHER INFORMATION: Transduction domain

<400> SEQUENCE: 44

Lys Met Thr Arg Ala Gln Arg Arg Ala Ala Ala Arg Arg Asn Arg Trp
1               5                   10                  15

Thr Ala Arg

<210> SEQ ID NO 45
<211> LENGTH: 13
<212> TYPE: PRT
<213> ORGANISM: Artificial Sequence
<220> FEATURE:
<223> OTHER INFORMATION: Transduction domain

<400> SEQUENCE: 45

Thr Arg Arg Gln Arg Thr Arg Arg Ala Arg Arg Asn Arg
1               5                   10

<210> SEQ ID NO 46
<211> LENGTH: 13

```
<212> TYPE: PRT
<213> ORGANISM: Artificial Sequence
<220> FEATURE:
<223> OTHER INFORMATION: Transduction domain

<400> SEQUENCE: 46

Gly Arg Lys Lys Arg Arg Gln Arg Arg Pro Pro Gln
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Transduction domain

<400> SEQUENCE: 47

Gly Arg Arg Arg Arg Arg Arg Arg Arg Pro Pro Gln
1               5                   10

<210> SEQ ID NO 48
<211> LENGTH: 27
<212> TYPE: PRT
<213> ORGANISM: Artificial Sequence
<220> FEATURE:
<223> OTHER INFORMATION: Transdcution domain

<400> SEQUENCE: 48

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 49
<211> LENGTH: 17
<212> TYPE: PRT
<213> ORGANISM: Artificial Sequence
<220> FEATURE:
<223> OTHER INFORMATION: Transduction domain

<400> SEQUENCE: 49

Lys Leu Ala Leu Lys Leu Ala Leu Lys Leu Ala Leu Ala Leu Lys Leu
1               5                   10                  15

Ala

<210> SEQ ID NO 50
<211> LENGTH: 27
<212> TYPE: PRT
<213> ORGANISM: Artificial Sequence
<220> FEATURE:
<223> OTHER INFORMATION: Transduction domain

<400> SEQUENCE: 50

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 51
<211> LENGTH: 27
<212> TYPE: PRT
<213> ORGANISM: Artificial Sequence
<220> FEATURE:
<223> OTHER INFORMATION: Transduction domain

<400> SEQUENCE: 51
```

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 52
<211> LENGTH: 27
<212> TYPE: PRT
<213> ORGANISM: Artificial Sequence
<220> FEATURE:
<223> OTHER INFORMATION: Transduction domain

<400> SEQUENCE: 52

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 53
<211> LENGTH: 27
<212> TYPE: PRT
<213> ORGANISM: Artificial Sequence
<220> FEATURE:
<223> OTHER INFORMATION: Transduction domain

<400> SEQUENCE: 53

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 54
<211> LENGTH: 21
<212> TYPE: PRT
<213> ORGANISM: Artificial Sequence
<220> FEATURE:
<223> OTHER INFORMATION: Transduction domain

<400> SEQUENCE: 54

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 55
<211> LENGTH: 21
<212> TYPE: PRT
<213> ORGANISM: Artificial Sequence
<220> FEATURE:
<223> OTHER INFORMATION: Transduction domain

<400> SEQUENCE: 55

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 56
<211> LENGTH: 8
<212> TYPE: PRT
<213> ORGANISM: Artificial Sequence
<220> FEATURE:
<223> OTHER INFORMATION: Transduction domain

```
<400> SEQUENCE: 56

Lys Lys Lys Lys Lys Lys Lys
1               5

<210> SEQ ID NO 57
<211> LENGTH: 8
<212> TYPE: PRT
<213> ORGANISM: Artificial Sequence
<220> FEATURE:
<223> OTHER INFORMATION: Transduction domain

<400> SEQUENCE: 57

Arg Gln Arg Gln Arg Gln Arg Gln
1               5
```